US009326934B2

(12) United States Patent
Gravett et al.

(10) Patent No.: US 9,326,934 B2
(45) Date of Patent: May 3, 2016

(54) DRUG DELIVERY FROM RAPID GELLING POLYMER COMPOSITION

(75) Inventors: David M. Gravett, Mountain View, CA (US); Aniko Takacs-Cox, North Vancouver (CA); Philip M. Toleikis, Vancouver (CA); Arpita Maiti, Vancouver (CA); Leanne Embree, Squamish (CA)

(73) Assignee: Angiotech International AG

( * ) Notice: Subject to any disclaimer, the term of this patent is extended or adjusted under 35 U.S.C. 154(b) by 0 days.

(21) Appl. No.: 13/461,424

(22) Filed: May 1, 2012

(65) Prior Publication Data
US 2012/0252905 A1 Oct. 4, 2012

Related U.S. Application Data

(63) Continuation of application No. 12/259,916, filed on Oct. 28, 2008, now abandoned, which is a continuation of application No. 10/749,117, filed on Dec. 30, 2003, now abandoned.

(60) Provisional application No. 60/437,471, filed on Dec. 30, 2002, provisional application No. 60/440,875, filed on Jan. 17, 2003.

(51) Int. Cl.
| *A61K 9/14* | (2006.01) |
| *A61K 9/00* | (2006.01) |
| *A61K 9/06* | (2006.01) |
| *A61K 9/16* | (2006.01) |
| *A61K 31/337* | (2006.01) |
| *A61K 31/365* | (2006.01) |
| *A61K 31/54* | (2006.01) |
| *A61K 47/34* | (2006.01) |
| *A61L 31/04* | (2006.01) |
| *A61L 31/14* | (2006.01) |
| *A61L 31/16* | (2006.01) |
| *A61K 47/48* | (2006.01) |
| *A61K 51/12* | (2006.01) |

(52) U.S. Cl.
CPC ............ *A61K 9/0024* (2013.01); *A61K 9/06* (2013.01); *A61K 9/1647* (2013.01); *A61K 31/337* (2013.01); *A61K 31/365* (2013.01); *A61K 31/54* (2013.01); *A61K 47/34* (2013.01); *A61L 31/041* (2013.01); *A61L 31/145* (2013.01); *A61L 31/16* (2013.01); *A61K 47/48784* (2013.01); *A61K 51/1213* (2013.01); *A61L 2300/434* (2013.01)

(58) Field of Classification Search
None
See application file for complete search history.

(56) References Cited

U.S. PATENT DOCUMENTS

| 3,619,371 A | 11/1971 | Crook et al. |
| 3,742,955 A | 7/1973 | Battista et al. |
| 3,788,948 A | 1/1974 | Kegadal et al. |
| 3,810,473 A | 5/1974 | Cruz, Jr. et al. |
| 3,876,501 A | 4/1975 | Hanushewsky |
| 3,949,073 A | 4/1976 | Daniels et al. |
| 3,960,830 A | 6/1976 | Bayer et al. |
| 4,002,531 A | 1/1977 | Royer |
| 4,055,635 A | 10/1977 | Green et al. |
| 4,088,538 A | 5/1978 | Schneider |
| 4,101,380 A | 7/1978 | Rubinstein et al. |
| 4,164,559 A | 8/1979 | Miyata et al. |
| 4,179,337 A | 12/1979 | Davis et al. |
| 4,192,021 A | 3/1980 | Deibig et al. |
| 4,238,480 A | 12/1980 | Sawyer |
| 4,261,973 A | 4/1981 | Lee et al. |
| 4,279,812 A | 7/1981 | Cioca |
| 4,301,144 A | 11/1981 | Iwashita et al. |
| 4,314,380 A | 2/1982 | Miyata |
| 4,320,201 A | 3/1982 | Berg et al. |
| 4,357,274 A | 11/1982 | Werner |
| 4,390,519 A | 6/1983 | Sawyer |
| 4,404,970 A | 9/1983 | Sawyer |
| 4,412,947 A | 11/1983 | Cioca |
| 4,412,989 A | 11/1983 | Iwashita |
| 4,414,147 A | 11/1983 | Klibanov et al. |
| 4,415,628 A | 11/1983 | Cioca et al. |
| 4,415,665 A | 11/1983 | Mosbach et al. |

(Continued)

FOREIGN PATENT DOCUMENTS

| EP | 0 650 512 B1 | 10/2001 | |
| WO | WO 90/05755 | 5/1990 | |
| WO | WO 92/06678 | 4/1992 | |
| WO | WO 94/01483 | 1/1994 | |
| WO | WO 96/29370 | 9/1996 | |
| WO | WO 98/12243 | 3/1998 | |
| WO | WO 00/09087 | 2/2000 | |
| WO | WO 00/33764 | 6/2000 | |
| WO | WO 00/62827 | 10/2000 | |
| WO | WO 01/05379 A1 * | 1/2001 | ............... A61K 9/50 |

(Continued)

OTHER PUBLICATIONS

Zhang et al. "An investigation of the antitumour activity and biodistribution of polymeric micellar paclitaxel", Cancer Chemother Pharmacol (1997) 40: 81-86.*

(Continued)

*Primary Examiner* — James Rogers

(57) ABSTRACT

Compositions are disclosed that afford drug delivery from two-part polymer compositions that rapidly form covalent linkages when mixed together. Such compositions are particularly well suited for use in a variety of tissue related applications when rapid adhesion to the tissue and gel formation is desired along with drug delivery. For example, the compositions are useful as tissue sealants, in promoting hemostasis, in effecting tissue adhesion, in providing tissue augmentation, and in the prevention of surgical adhesions.

11 Claims, 8 Drawing Sheets

(56) References Cited

U.S. PATENT DOCUMENTS

| | | |
|---|---|---|
| 4,424,208 A | 1/1984 | Wallace et al. |
| 4,451,568 A | 5/1984 | Schneider et al. |
| 4,488,911 A | 12/1984 | Luck et al. |
| 4,495,285 A | 1/1985 | Shimizu et al. |
| 4,496,689 A | 1/1985 | Mitra |
| 4,515,637 A | 5/1985 | Cioca |
| 4,544,516 A | 10/1985 | Hughes et al. |
| 4,553,974 A | 11/1985 | Dewanjee |
| 4,557,764 A | 12/1985 | Chu, II |
| 4,563,350 A | 1/1986 | Nathan et al. |
| 4,563,351 A | 1/1986 | Caslavsky et al. |
| 4,563,490 A | 1/1986 | Stol et al. |
| 4,578,067 A | 3/1986 | Cruz, Jr. |
| 4,582,640 A | 4/1986 | Smestad et al. |
| 4,592,864 A | 6/1986 | Miyata et al. |
| 4,600,533 A | 7/1986 | Chu |
| 4,642,117 A | 2/1987 | Nguyen |
| 4,655,980 A | 4/1987 | Chu |
| 4,670,417 A | 6/1987 | Iwasaki et al. |
| 4,678,468 A | 7/1987 | Hiroyoshi |
| 4,687,820 A | 8/1987 | Hou et al. |
| 4,689,399 A | 8/1987 | Chu |
| 4,703,108 A | 10/1987 | Silver et al. |
| 4,704,131 A | 11/1987 | Noishiki et al. |
| 4,725,671 A | 2/1988 | Chu et al. |
| 4,732,863 A | 3/1988 | Tomasi |
| 4,737,544 A | 4/1988 | McCain et al. |
| 4,745,180 A | 5/1988 | Moreland et al. |
| 4,766,106 A | 8/1988 | Katre |
| 4,774,227 A | 9/1988 | Piez et al. |
| 4,789,663 A | 12/1988 | Wallace et al. |
| 4,795,467 A | 1/1989 | Piez et al. |
| 4,828,563 A | 5/1989 | Muller-Lierheim |
| 4,847,325 A | 7/1989 | Shadle et al. |
| 4,851,513 A | 7/1989 | Devore et al. |
| 4,935,465 A | 6/1990 | Garman |
| 4,950,483 A | 8/1990 | Ksander |
| 4,950,699 A | 8/1990 | Holman |
| 4,973,493 A | 11/1990 | Guire |
| 4,979,959 A | 12/1990 | Guire |
| 4,980,403 A | 12/1990 | Bateman et al. |
| 4,983,580 A | 1/1991 | Gibson |
| 5,024,742 A | 6/1991 | Nesburn et al. |
| 5,104,957 A | 4/1992 | Kelman et al. |
| 5,122,614 A | 6/1992 | Zalipsky |
| 5,141,747 A | 8/1992 | Scholz |
| 5,156,613 A | 10/1992 | Sawyer |
| 5,162,430 A | 11/1992 | Rhee et al. |
| 5,167,960 A | 12/1992 | Ito et al. |
| 5,169,754 A | 12/1992 | Siiman et al. |
| 5,192,316 A | 3/1993 | Ting |
| 5,198,493 A | 3/1993 | Holmberg et al. |
| 5,201,764 A | 4/1993 | Kelman et al. |
| 5,209,776 A | 5/1993 | Bass et al. |
| 5,219,564 A | 6/1993 | Zalipsky et al. |
| 5,219,895 A | 6/1993 | Kelman et al. |
| 5,264,214 A | 11/1993 | Rhee et al. |
| 5,290,552 A | 3/1994 | Sierra et al. |
| 5,292,802 A | 3/1994 | Rhee et al. |
| 5,298,643 A | 3/1994 | Greenwald |
| 5,304,595 A | 4/1994 | Rhee et al. |
| 5,306,500 A | 4/1994 | Rhee et al. |
| 5,308,889 A | 5/1994 | Rhee et al. |
| 5,321,095 A | 6/1994 | Greenwald |
| 5,324,775 A | 6/1994 | Rhee et al. |
| 5,324,844 A | 6/1994 | Zalipsky |
| 5,328,955 A | 7/1994 | Rhee et al. |
| 5,349,001 A | 9/1994 | Greenwald et al. |
| 5,354,336 A | 10/1994 | Kelman et al. |
| 5,364,622 A | 11/1994 | Frnz et al. |
| 5,405,877 A | 4/1995 | Greenwald et al. |
| 5,410,016 A | 4/1995 | Hubbell et al. |
| 5,455,027 A | 10/1995 | Zalipsky et al. |
| 5,475,052 A | 12/1995 | Rhee et al. |
| 5,514,379 A | 5/1996 | Weissleder et al. |
| 5,549,904 A | 8/1996 | Juergensen et al. |
| 5,567,422 A | 10/1996 | Greenwald |
| 5,583,114 A | 12/1996 | Barrows et al. |
| 5,605,976 A | 2/1997 | Martinez et al. |
| 5,612,460 A | 3/1997 | Zalipsky |
| 5,614,549 A | 3/1997 | Greenwald et al. |
| 5,614,587 A | 3/1997 | Rhee et al. |
| 5,626,863 A | 5/1997 | Hubbell et al. |
| 5,637,749 A | 6/1997 | Greenwald |
| 5,643,575 A | 7/1997 | Martinez et al. |
| 5,700,848 A | 12/1997 | Soon-Shiong et al. |
| 5,752,974 A | 5/1998 | Rhee et al. |
| 5,786,421 A | 7/1998 | Rhee et al. |
| 5,854,382 A * | 12/1998 | Loomis .................. 528/354 |
| 5,874,500 A | 2/1999 | Rhee et al. |
| 5,900,245 A | 5/1999 | Sawhney et al. |
| 5,936,035 A | 8/1999 | Rhee et al. |
| 6,051,248 A | 4/2000 | Sawhney et al. |
| 6,051,648 A | 4/2000 | Rhee et al. |
| 6,165,489 A | 12/2000 | Berg et al. |
| 6,166,130 A | 12/2000 | Rhee et al. |
| 6,217,894 B1 | 4/2001 | Sawhney et al. |
| 6,287,588 B1 | 9/2001 | Shih et al. |
| 6,312,725 B1* | 11/2001 | Wallace et al. ............. 424/484 |
| 6,323,278 B2 | 11/2001 | Rhee et al. |
| 6,352,710 B2 | 3/2002 | Sawhney et al. |
| 6,458,889 B1 | 10/2002 | Trollsas et al. |
| 6,534,591 B2 | 3/2003 | Rhee et al. |
| 6,624,245 B2* | 9/2003 | Wallace et al. ............ 525/54.1 |
| 2001/0029264 A1* | 10/2001 | McChesney-Harris ....... 514/449 |
| 2002/0165337 A1 | 11/2002 | Wallace et al. |
| 2003/0012818 A1* | 1/2003 | Schense et al. ............. 424/486 |

FOREIGN PATENT DOCUMENTS

| | | |
|---|---|---|
| WO | WO 01/60335 | 8/2001 |
| WO | WO 02/072150 | 9/2002 |
| WO | WO 2004/044223 | 5/2004 |
| WO | WO 2004/060346 | 7/2004 |

OTHER PUBLICATIONS

Abuchowski, A. et al., "Alteration of Immunological Properties of Bovine Serum Albumin by Covalent Attachment of Polyethylene Glycol," *The Journal of Biological Chemistry* 252(11): 3578-3581, Jun. 10, 1977.

Abuchowski, A. et al., "Cancer therapy with Chemically modified enzymes. I. Antitumor properties of polyethylene glycol-asparaginase conjugates," *Cancer Biochem. Biophys.* 7(2):175-186, 1984.

Abuchowski, A. et al., "Effect of Covalent Attachment of Polyethylene Glycol on Immunogenicity and Circulating Life of Bovine Liver Catalase," *The Journal of Biological Chemistry* 252(11): 3582-3586, Jun. 1977.

Anderson, GW. Et al., "The Use of Esters of N-Hydroxysuccinimide in Peptide Synthesis," *Journal of the American Chemical Society* 86(9): 1839-1842, May 5, 1964.

Beauchamp, C.O. et al., "A New Procedure for the Synthesis of Polyethylene Glycol-Protein Adducts; Effects on Function, Receptor Recognition, and Clearance of Superoxide Dismutase, Lactoferrin, and ** Macroglobulin," *Analytical Biochemistry* 131(1):25-33, May 1983.

Bendich, A. et al., "Immunological effects of native and polyethylene glycol-modified asparaginases from *Vibrio succinogenes* and *Escherichia coli* in normal and tumour-bearing mice," *Clin. Exp. Immunol.* 48(1):273-278, Apr. 1982.

Chen, R.H.L. et al., "properties of two urate oxidases modified by the covalent attachment of poly(ethylene glycole)," *Biochimica et Biophysica Acta 660*: 293-298, 1981.

Chvapil, M. et al., "some Chemical and Biological Characteristics of a New Collagen-Polymer Compound Material," *Journal of Biomedical Materials Research* 3(1): 315-332, Mar. 1969.

Davis, S. et al., "Hypouricaemic Effect of Polyethyleneglycol Modified Urate Oxidase," *The Lancet 2*: 281-283, Aug. 8, 1981.

(56) References Cited

OTHER PUBLICATIONS

Doillon, C.J. et al., "Collagen-based wound dressings: Control of the pore structure and morphology," Journal of Biomedical Materials Research 20(8): 1219-1228, Oct. 1986.
Ferruti, P. et al., "Succinic Half-esters of Poly(ethylene glycol)s and Their Benzotriazole and Imidazole Derivatives as Oligomeric Drug-binding Matrices," *Makromol. Chem. 182*(8): 2183-2192, Aug. 1981.
Fleischer, N. et al., "Regeneration of Lost Attachment Apparatus in the Dog using Polygalactin-910," *Journal of Dental Research 86*(Special Issue): 281, Abstract No. 1393, 1987.
Gander, B. et al., "Crosslinked poly(alkylene oxides) for the preparation of controlled release micromatrices," *Journal of Controlled Release 5*:271-283, 1988.
Gnanou, Y. et al., "Hydrophilic Polyurethane Networks Based on Poly(ethylene oxide): Synthesis, Characterization, and Properties. Potential Applications as Biomaterials," *Macromolecules 17*: 945-952, 1984.
Gomel, V. et al., "Infertility surgery: microsurgery," *Current Opinion in Obstetrics and Gynecology 4*: 390-399, 1992.
Inada, Y. et al., "Ester synthesis catalyzed by polyethylene glycol-modified lipase in benzene,"*Biochemical and Biophysical Research Communications 122*(2): 8445-850, Jul. 31, 1984.
Katre, N. V. et al., "Chemical modification of recombinant interleukin 2 by polyethylene glycol increases its potency in the murine Meth A sarcoma model," *Proc. Natl. Acad. Sci. USA 84*: 1487-1491, Mar. 1987.
McPherson, J.M. et al., The Influence of Heparin on the Wound Healing Response to Collagen Implants in vivo, *Collagen Rel. Res. 1*: 83-100, 1988.
Nishida, Y. et al., "Hypouricaemic effect after oral administration in chickens of Polyethylene glycol-modified uricase entrapped in liposomes," *J Pharm. Pharmacol. 36*(5): 354-355, May 1984.
Pados, G.A. et al., "Adhesions," *Current Opinion in Obstetrics and Gynecology 4*: 412-418, 1992.
Pagidas, K. et al., "Effects of Ringer's lactate, Interceed(TC7) and Gore-Tex Surgical Membrane on postsurgical adhesion formation," *Fertility and Sterility 57*(1): 199-201, Jan. 1992.
Pyatak, P.S. eta l., "Preparation of a polyethylene glycol: Superoxide dismutase adduct, and an examination of its blood circulating life and anti-inflammatory activity," Research *Communications in Chemical Pathology and Pharmacology 29*(1): 113-127, Jul. 1980.
Ramshaw, J.A.M. et al., "Precipitation of Collagens by Polyethylene Glycols," *Analytical Biochemistry 141*(2): 361-365, Sep. 1984.
Savoca, K.V. et al., "Preparation of a Non-Immunogenic Arginase by the Covalent Attachment of Polyethylene Glycol," *Biochimic et Biophysica Acta 578*: 47-53, 1979.
Sawhney, A.S. et al., "Optimization of photopolymerized bioerodible hydrogel properties for adhesion prevention," *Journal of Biomedical Materials Research 28*:831-838, 1994.
Sierra, D., "Fibrin Sealant Adhesive Systems: A Review of Their Chemistry, Material Properties and Clinical Applications, "*Journal of Biomaterials Applications*, 7:309-351, Jan. 1993.
Steinleitner, A. et al., "Poloxamer 407 as an Intraperitoneal Barrier Material for the Prevention of Postsurgical Adhesion Formation and Reformation in Rodent Models for Reproductive Surgery," *Obstet. Gynecol. 77*: 48-52, 1991.
Takahashi, K. et al., "A Chemical Modification to make horseradish peroxidase soluble and active in benzene," *Biochemical and Biophysical Research Communications 121*(1): 262-265, May 31, 1984.
Tulandi, T., "Effects of fibrin sealant on tubal anastomosis and adhesion formation," *Fertility and Sterility 56*(1): 136-138, Jul. 1991.
Ulbrich, K. et al., "Poly(ethylene glycol)s containing enzymatically degradable bonds,"*Makromol. Chem.* 187: 1131-1144, May 1986.
Urman, B. et al., "Effect of hyaluronic acid on postoperative intraperitoneal adhesion formation and reformation in the rat model, "*Fertility and Sterility 56*(3): 568-570. Sep. 1991.
Viau, A.T. et al., "Safety evaluation of free radical scavengers PEG-catalase and PEG-superoxide dismutase," *Journal of Free Radicals in Biology & Medicine 2*(4): 283-288, 1986.
Viau, A.T. et al., "Toxicologic studies of a conjugate of asparaginase and polyethylene glycol in mice, rats, and dogs,"*Am. J. Vet. Res. 47*(6): 1398-1401, Jun. 1986.
Wallace, D. G. et al., "A Tissue Sealant Based on Reactive Multifunctional Polyethylene Glycol," *Journal of Biomedical Materials Research*, 58(5):545-555,2001.
West, J.L. et al., "Comparison of covalently and physically cross-linked polyethylene glycol-based hydrogels for the prevention of postoperative adhesions in a rat model," *Biomaterials 16*(15): 1153-1156, Oct. 1995.
Wieder, K. J. et al., "Some Properties of Polyethylene Glycol: Phenylalanine Ammonia-Lyase Adducts," *The Journal of Biological Chemistry 254*(24): 12579-12587, Dec. 25, 1979.
Zhou, X. and Harris, J.M., "Novel Degradable Poly(ethylene glycol) Hydrogels for Controlled Release of Protein," Journal of Pharmaceutical Sciences, 87(11):1450-1458, Nov. 1, 1998.

\* cited by examiner

DRUG DELIVERY FROM RAPID GELLING POLYMER COMPOSITION

CROSS REFERENCE TO RELATED APPLICATIONS

This application is a continuation of U.S. patent application Ser. No. 12/259,916, filed Oct. 28, 2008, which is a continuation of U.S. patent application Ser. No. 10/749,117, filed Dec. 30, 2003, now abandoned; which claims the benefit under 35 U.S.C. §119(e) of U.S. Provisional Patent Application No. 60/437,471, filed Dec. 30, 2002, and U.S. Provisional Patent Application No. 60/440,875, filed Jan. 17, 2003, which applications are included herein by reference in their entirety.

BACKGROUND OF THE INVENTION

1. Field of the Invention

This invention relates generally to compositions that afford drug delivery from two-part polymer compositions that rapidly form covalent linkages when mixed together. Such compositions are particularly well suited for use in a variety of tissue related applications when rapid adhesion to the tissue and gel formation is desired along with drug delivery. For example, the compositions are useful as tissue sealants, in promoting hemostasis, in effecting tissue adhesion, in providing tissue augmentation, and in the prevention of surgical adhesions.

2. Description of the Related Art

The use of polymer compositions in tissue engineering is now widely recognized, particularly those consisting of synthetic polymers. In contrast to many naturally derived compositions, synthetic polymer compositions can be formulated to exhibit predetermined physical characteristics such as gel strength, as well as biological characteristics such as degradability.

In a variety of tissue engineering applications, it is desirable to use compositions that can be administered as liquids, but subsequently form hydrogels at the site of administration. Such in situ hydrogel forming compositions are more convenient to use since they can be administered as liquids from a variety of different devices, and are more adaptable for administration to any site, since they are not preformed. Many different mechanisms have been described that can be used to promote hydrogel formation in situ. For example, photoactivatable mixtures of water-soluble co-polyester prepolymers and polyethylene glycol have been described to create hydrogel barriers, as well as drug release matrices. In another approach, block copolymers of polyalkylene oxide polymers (e.g., PLURONIC compounds from BASF Corporation, Mount Olive, N.J.) and poloxamers have been designed that are soluble in cold water, but form insoluble hydrogels that adhere to tissues at body temperature (Leach, et al., Am. J. Obstet. Gynecol. 162:1317-1319 (1990)). Polymerizable cyanoacrylates have also been described for use as tissue adhesives (Ellis, et al., J. Otolaryngol. 19:68-72 (1990)). In yet another approach, two-part synthetic polymer compositions have been described that, when mixed together, form covalent bonds with one another, as well as with exposed tissue surfaces. (PCT WO 97/22371, which corresponds to U.S. application Ser. No. 08/769,806 U.S. Pat. No. 5,874,500.) In a similar approach involving a two-part composition, a mixture of protein and a bifunctional crosslinking agent has been described for use as a tissue adhesive (U.S. Pat. No. 5,583,114.)

One difficulty encountered when designing in situ hydrogel forming compositions is that optimizing the composition to enhance gel formation may worsen tissue inflammation at the site of administration. A possible explanation for this effect is that highly reactive composition components that are capable of rapid gel formation may adversely affect tissue surfaces.

The compositions of the present invention have been formulated to provide for rapid gelation, and also cause less tissue inflammation at the site of administration than previously described compositions.

BRIEF SUMMARY OF THE INVENTION

Briefly stated, the present invention provides compositions and methods for drug delivery, including precursors to said compositions.

For example, in one aspect, the present invention provides a biocompatible gel-forming drug-delivering composition for in vivo administration, comprising:

a drug;

a first component comprising at least one sulfhydryl group-containing compound in a liquid medium having an alkaline pH, wherein said sulfhydryl group-containing compound is given by the formula $Compound_1\text{-}(SH)_m$, wherein $m \geq 2$; and a second component comprising at least one sulfhydryl reactive group-containing compound in either a liquid medium having a neutral or acidic pH or in powder form, wherein said sulfhydryl reactive group-containing compound is given by the formula $Compound_2\text{-}Y_n$, wherein Y is a sulfhydryl reactive group and wherein $n \geq 2$;

wherein at least one of the first or second components is a polyalkylene oxide and wherein the sulfhydryl groups and the sulfhydryl reactive groups react with one another to form covalent bonds therebetween when said components are mixed together. Preferably, the covalent bonds form a gel in less than one minute after mixing.

The invention also provides a method for treating tissues, comprising the steps of:

administering to a tissue site a first component comprising at least one sulfhydryl group-containing compound in liquid medium having an alkaline pH, wherein said sulfhydryl group-containing compound is given by the formula $Compound_1\text{-}(SH)_m$, wherein $m \geq 2$; and simultaneously or subsequently administering to the tissue site a second component comprising at least one sulfhydryl reactive group-containing compound either a liquid medium having a neutral or acidic pH or in powder form, wherein said sulfhydryl reactive group-containing compound is given by the formula $Compound_2\text{-}Y_n$, wherein Y is a sulfhydryl reactive group and wherein $n \geq 2$, and wherein at least one of the first or second components is a polyalkylene oxide; and simultaneously or subsequently administering to the tissue site a drug; and allowing the sulfhydryl groups and the sulfhydryl reactive groups to react with one another to form covalent bonds therebetween to form a gel in less than one minute.

In another aspect, the invention provides a biocompatible gel-forming drug-delivering composition for in vivo administration with a gel time of less than one minute, comprising:

polyalkylene oxide-$(SH)_4$ and drug in a liquid medium having a pH of between 8 and 10.5; and polyalkylene oxide-$Y_4$, wherein Y is succinimidyl, in a liquid medium having an acidic pH.

In another aspect, the invention provides a biocompatible gel-forming drug-delivering composition for in vivo administration with a gel time of less than one minute, comprising:

polyalkylene oxide-$(SH)_{12}$ and drug in a liquid medium having an alkaline pH; and polyalkylene oxide-$Y_{12}$ in a liquid medium having an acidic pH, wherein Y is a succinimidyl or maleimidyl group.

In another aspect, the invention provides a biocompatible gel-forming composition for in vivo administration, comprising:

a sulfhydryl group-containing polyalkylene oxide in a liquid medium having an acidic pH, wherein said sulfhydryl group-containing polyalkylene oxide is given by the formula Core-$(SH)_m$, wherein $m \geq 2$;

a buffer solution with an alkaline pH; and drug in admixture with the polyalkylene oxide and/or the buffer solution;

wherein the sulfhydryl groups react with one another to form covalent bonds therebetween when said components are mixed together to form a gel in less than one minute.

In another aspect, the present invention provides a biocompatible gel-forming drug-delivering composition for in vivo administration, comprising:

at least one sulfhydryl group-containing compound in a liquid medium having an alkaline pH, wherein said sulfhydryl group-containing compound is given by the formula Compound$_1$-$(SH)_m$, wherein $m \geq 2$;

at least one sulfhydryl reactive group-containing compound either a liquid medium having a neutral or acidic pH or in powder form, wherein said sulfhydryl reactive group-containing compound is given by the formula Compound$_2$-$Y_n$, wherein Y is a sulfhydryl reactive group and wherein $n \geq 2$;

at least one drug in admixture with either or both of the at least one sulfhydryl group-containing compound and the at least one sulfhydryl reactive group-containing compound; and collagen;

wherein at least one of either the sulfhydryl group-containing compound or the sulfhydryl reactive group-containing compound is a polyalkylene oxide, and wherein the sulfhydryl groups and the sulfhydryl reactive groups are capable of reacting with one another to form covalent bonds therebetween.

In another aspect, the present invention provides a biocompatible gel-forming drug-delivering composition for in vivo administration, comprising:

(a) a first component in a liquid medium having an acidic pH comprising:

(i) at least one sulfhydryl group-containing compound given by the formula Compound$_1$-$(SH)_m$, wherein $m \geq 2$;

(ii) at least one sulfhydryl reactive group-containing compound given by the formula Compound$_2$-$Y_n$, wherein Y is a sulfhydryl reactive group and wherein $n \geq 2$; and (iii) collagen; and (b) a second component comprising a buffer having a pH of between 8 and 10.5;

wherein a drug is present in admixture with either or both of the first component or the second component; and wherein at least one of either the sulfhydryl group containing compound or the sulfhydryl reactive group containing compound is a polyalkylene oxide.

Optionally, in each of these and other aspects of the invention as disclosed herein, the drug is a hydrophobic drug in admixture with a secondary carrier to provide drug/carrier, the drug/carrier being in admixture with either or both of the at least one sulfhydryl group-containing compound and the at least one sulfhydryl reactive group-containing compound.

Furthermore, the present invention provides various methods that are useful in preparing drug-containing delivery vehicles. For example, in one aspect the invention provides a method for forming a drug delivery composition, comprising a) selecting a first component, a second component and a drug, wherein the first component comprises at least one sulfhydryl group-containing compound in a liquid medium having an alkaline pH, wherein said sulfhydryl group-containing compound is given by the formula Compound$_1$-$(SH)_m$, wherein $m \geq 2$; and the second component comprises at least one sulfhydryl reactive group-containing compound in either a liquid medium having a neutral or acidic pH or in powder form, wherein said sulfhydryl reactive group-containing compound is given by the formula Compound$_2$-$Y_n$, wherein Y is a sulfhydryl reactive group and wherein $n \geq 2$;

at least one of the first or second components is a polyalkylene oxide;

the sulfhydryl groups and the sulfhydryl reactive groups react with one another to form covalent bonds therebetween when said components are mixed together to form a gel in less than one minute;

b) combining the first and second components in the presence of the drug, under conditions where the first component reacts with the second component. The invention also provides a product produced by this method.

In another aspect, the invention provides a method for forming a drug delivery composition, comprising a) forming an admixture of polyalkylene oxide-$(SH)_4$ and drug in a liquid medium having a pH of between 8 and 10.5; and b) forming an admixture of polyalkylene oxide-$Y_4$, wherein Y is succinimidyl and liquid medium, the admixture having an acidic pH. The invention may further include the step of combining the admixtures of steps a) and b), and in addition the invention provides the product produced by this method.

In another aspect, the invention provides a method for forming a biocompatible gel-forming drug-delivering composition for in vivo administration, preferably having a gel time of less than one minute, comprising:

a) preparing an admixture of polyalkylene oxide-$(SH)_{12}$ and drug in a liquid medium having an alkaline pH; and b) preparing polyalkylene oxide-$Y_{12}$ in a liquid medium having an acidic pH, wherein Y is a succinimidyl or maleimidyl group. In one aspect, this method further includes the step of combining a) and b), while in a related aspect the invention provides the product produced by this method.

In another aspect, the present invention provides a method for forming a biocompatible gel-forming composition for in vivo administration, the method comprising:

a) preparing a sulfhydryl group-containing polyalkylene oxide in a liquid medium having an acidic pH, wherein said sulfhydryl group-containing polyalkylene oxide is given by the formula Core-$(SH)_m$, wherein $m \geq 2$;

b) providing a buffer solution with an alkaline pH; and c) adding drug to either or both of a) and b);

wherein the sulfhydryl groups react with one another to form covalent bonds therebetween when said components are mixed together to form a gel in less than one minute. Optionally, the method includes combining a) and b), while in a related aspect the invention provides the product produced by this method.

In another aspect, the present invention provides a method for forming a biocompatible gel-forming drug-delivering composition for in vivo administration, comprising:

a) providing an at least one sulfhydryl group-containing compound in a liquid medium having an alkaline pH, wherein said sulfhydryl group-containing compound is given by the formula Compound$_1$-(SH)$_m$, wherein m≥2;

b) providing an at least one sulfhydryl reactive group-containing compound either in a liquid medium having a neutral or acidic pH or in powder form, wherein said sulfhydryl reactive group-containing compound is given by the formula Compound$_2$-Y$_n$, wherein Y is a sulfhydryl reactive group and wherein n≥2;

c) combining a drug with either or both of the at least one sulfhydryl group-containing compound and the at least one sulfhydryl reactive group-containing compound; and d) providing collagen;

wherein at least one of either the sulfhydryl group-containing compound or the sulfhydryl reactive group-containing compound is a polyalkylene oxide; and wherein the sulfhydryl groups and the sulfhydryl reactive groups are capable of reacting with one another to form covalent bonds therebetween. Optionally, the method includes the step of combining a), b) and d), and in a related aspect the invention provides the product produced by this method.

A variety of drugs may be included in the compositions of the present invention, and used in the methods of the present invention. These drugs are set forth in detail below. The following are specific aspects of the present invention, which are exemplary only: in one aspect, the compositions and methods of the invention employ (i.e., include in a composition, or use in a method) a cell cycle inhibitor; in one aspect, the compositions and methods of the invention employ paclitaxel; in one aspect, the compositions and methods of the invention employ doxorubicin; in one aspect, the compositions and methods of the invention employ mitoxantrone; in one aspect, the compositions and methods of the invention employ podophyllotoxin (e.g., etoposide); in one aspect, the compositions and methods of the invention employ an immunomodulatory agents; in one aspect, the compositions and methods of the invention employ rapamycin; in one aspect, the compositions and methods of the invention employ everolimus; in one aspect, the compositions and methods of the invention employ tacrolimus; in one aspect, the compositions and methods of the invention employ biolimus; in one aspect, the compositions and methods of the invention employ a heat shock protein 90 antagonist; in one aspect, the compositions and methods of the invention employ geldanamycin; in one aspect, the compositions and methods of the invention employ a HMG CoA Reductase inhibitor; in one aspect, the compositions and methods of the invention employ simvastatin; in one aspect, the compositions and methods of the invention employ an IMPDH Inhibitor; in one aspect, the compositions and methods of the invention employ mycophenolic acid; in one aspect, the compositions and methods of the invention employ 1-alpha-25 dihydroxy vitamin D3; in one aspect, the compositions and methods of the invention employ an antimycotic agent; in one aspect, the compositions and methods of the invention employ sulconizole; in one aspect, the compositions and methods of the invention employ a P38 MAP kinase inhibitor; in one aspect, the compositions and methods of the invention employ SB220025; in one aspect, the compositions and method of the invention employ talcum powder; in one aspect, the compositions and method of the invention employ metallic beryllium and oxides thereof; in one aspect, the compositions and method of the invention employ copper; in one aspect, the compositions and method of the invention employ silk; in one aspect, the compositions and method of the invention employ silica; in one aspect, the compositions and method of the invention employ crystalline silicates; in one aspect, the compositions and method of the invention employ talc; in one aspect, the compositions and method of the invention employ quartz dust; in one aspect, the compositions and method of the invention employ ethanol; in one aspect, the compositions and method of the invention employ a component of extracellular matrix; in one aspect, the compositions and method of the invention employ fibronectin; in one aspect, the compositions and method of the invention employ collagen; in one aspect, the compositions and method of the invention employ fibrin; in one aspect, the compositions and method of the invention employ fibrinogen; in one aspect, the compositions and method of the invention employ polylysine; in one aspect, the compositions and method of the invention employ poly(ethylene-co-vinylacetate); in one aspect, the compositions and method of the invention employ chitosan; in one aspect, the compositions and method of the invention employ N-carboxybutylchitosan; in one aspect, the compositions and method of the invention employ a RGD protein; in one aspect, the compositions and method of the invention employ vinyl chloride; in one aspect, the compositions and method of the invention employ a polymer formed from vinyl chloride; in one aspect, the compositions and method of the invention employ a cyanoacrylate adhesive; in one aspect, the compositions and method of the invention employ an adhesive comprising crosslinked poly(ethylene glycol) derived material and methylated collagen; in one aspect, the compositions and method of the invention employ an inflammatory cytokine; in one aspect, the compositions and method of the invention employ an inflammatory cytokine selected from the group consisting of TGFb, PDGF, VEGF, bFGF, TNFa, NGF, GM-CSF, IGF-a, IL-1, IL-8, IL-6, and growth hormone; in one aspect, the compositions and method of the invention employ a connective tissue growth factor (CTGF); in one aspect, the compositions and method of the invention employ a bone morphogenic protein (BMP); in one aspect, the compositions and method of the invention employ a BMP selected from BMP-2, BMP-3, BMP-4, BMP-5, BMP-6, or BMP-7; in one aspect, the compositions and method of the invention employ bleomycin; in one aspect, the compositions and method of the invention employ an analogue or derivative of bleomycin; in one aspect, the compositions and method of the invention employ a proliferative agent that stimulates cellular proliferation; in one aspect, the compositions and method of the invention employ dexamethasone and analogues and derivatives thereof; in one aspect, the compositions and method of the invention employ isotretinoin and analogues and derivatives thereof; in one aspect, the compositions and method of the invention employ 17-β-estradiol and analogues and derivatives thereof; in one aspect, the compositions and method of the invention employ estradiol and analogues and derivatives thereof; in one aspect, the compositions and method of the invention employ diethylstibesterol and analogues and derivatives thereof; in one aspect, the compositions and method of the invention employ cyclosporine A and analogues and derivatives thereof; in one aspect, the compositions and method of the invention employ All-trans retinoic acid (ATRA) and analogues and derivatives thereof. Additional drugs that may be employed in the present invention are set forth below.

These and other aspects of the present invention will become evident upon reference to the following detailed description. In addition, various references are set forth herein. Each of these references is incorporated herein by reference in its entirety as if each were individually noted for incorporation.

BRIEF DESCRIPTION OF THE SEVERAL VIEWS OF THE DRAWING(S)

DETAILED DESCRIPTION OF THE INVENTION

Figure 1:
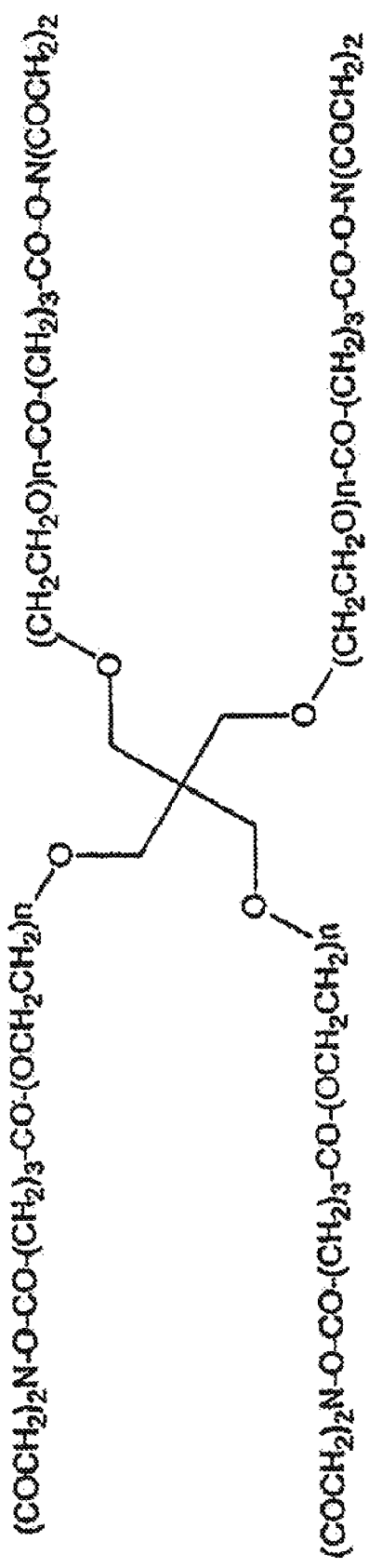
FIG. 1 is a tetrafunctionally activated PEG succinimidyl glutarate (ester linkage) (SG-PEG).
Figure 1:
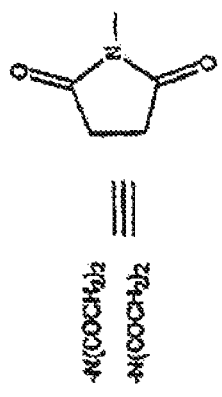

The present invention relates to drug delivery via a two-part polymer composition that forms a matrix when mixed together. Each component of the composition is generally administered separately to the tissue site, and the drug may be delivered with either component, or may be delivered separately. Then, within a very short time after being mixed together at the site of administration, the composition forms a gel with sufficient adhesive and cohesive strength to become anchored in place, and allow delivery of the drug to this location.

The components can be mixed prior to application to the tissue with the drug being mixed with the components prior to gellation or added after gellation has occurred.

DEFINITIONS

The following definitions are provided to further describe various aspects of the preferred embodiments of the present invention.

The term "gel" refers to the state of matter between liquid and solid. As such, a "gel" has some of the properties of a liquid (i.e., the shape is resilient and deformable) and some of the properties of a solid (i.e., the shape is discrete enough to maintain three dimensions on a two dimensional surface.) Accordingly, "gelation time", also referred to herein as "gel time", refers to the time it takes for a composition to become non-flowable under modest stress. This is generally exhibited as achieving a gel strength, G', of greater than or equal to $10^2$ dynes/cm$^2$ in less than 1 minute.

The term "cohesive strength" refers to the ability of the compositions of the present invention to remain intact, i.e., not rupture, tear or crack, when subjected to physical stresses or environmental conditions. Cohesive strength is sometimes measured as a function of "burst strength".

The term "adhesive strength" refers to the ability of the compositions of the present invention to be able to remain attached to the tissues at the site of administration when subjected to physical stresses or environmental conditions.

The term "polymer" refers to a molecule consisting of individual chemical moieties, which may be the same or different, but are preferably the same, that are joined together.

As used herein, the term "polymer" refers to individual chemical moieties that are joined end-to-end to form a linear molecule, as well as individual chemical moieties joined together in the form of a branched (e.g., a "multi-arm" or "star-shaped") structure.

The term "biocompatible" refers to the ability of the compositions of the present invention to be applied to tissues without eliciting significant inflammation and fibrosis or other adverse tissue responses.

The term "synthetic polymer" refers to polymers that are not naturally occurring and that are produced by chemical or recombinant synthesis. As such, naturally occurring proteins such as collagen and naturally occurring polysaccharides such as hyaluronic acid are specifically excluded. Proteins such as synthetic collagen, and carbohydrates such as synthetic hyaluronic acid, and their derivatives, are included.

The term "activated synthetic polymers" refers to synthetic polymers that have or have been chemically modified to have at least one functional group (e.g., a sulfhydryl group) that is capable of reacting with a corresponding reaction partner (e.g., a sulfhydryl-reactive group) to form a covalent bond. The term "multifunctionally activated" refers to synthetic polymers having two or more nucleophilic or electrophilic groups. Types of multifunctionally activated synthetic polymers include di-functionally activated, tri-functionally activated, tetra-functionally activated, and star-shaped activated polymers (that have four or more functional groups).

"Fibrosis" or "Scarring" refers to the formation of fibrous tissue in response to injury or medical intervention. Fibrosis or scarring is defined to involve biological processes which include an increase in one or more of the following: inflammation including production and release of cytokines and/or chemokines, angiogenesis, cellular proliferation (typically fibroblasts and/or smooth muscle cells), cell migration, ECM (extracellular matrix) production, tissue remodeling and cell adhesion.

Therapeutic agents which inhibit fibrosis or scarring can do so through one or more mechanisms including: inhibiting inflammatory processes such as production of cytokines and chemokines, inhibiting angiogenesis, inhibiting migration or proliferation of connective tissue cells (such as fibroblasts, and smooth muscle cells), reducing ECM production and/or inhibiting tissue remodeling. In addition, numerous therapeutic agents described in this invention will have the additional benefit of also reducing tissue regeneration (the replacement of injured cells by cells of the same type) when appropriate. An agent that modulates any of these events is referred to herein as an anti-scarring or a fibrosis-inhibiting agent.

Therapeutic agents which increase fibrosis or scarring can do so through an increase in one or more of the following processes: inflammation including production and release of cytokines and/or chemokines, angiogenesis, cellular proliferation (typically fibroblasts and/or smooth muscle cells), cell migration, ECM (extracellular matrix) production, tissue remodeling, cell adhesion and/or free radical production and release. Numerous therapeutic agents described in this invention are capable of inducing fibrosis or scarring and are referred to herein as fibrosing or scarring agents.

Composition Components

The compositions of the present invention comprise two or more different compounds, and at least one of which is a polymer, that react with one another to form a covalently crosslinked gel matrix. Depending on the reactivity of the compounds towards each other, the different compounds can be in separate parts of the starting compositions, or they can be in the same part of the starting composition. As such, they can easily be administered separately or simultaneously, and rapidly form gels at the site of administration. The compositions can also be formed into gels prior to application to the desired site. The compositions also include a drug that will be contained with the gel and delivered to the tissue at the site of gel administration.

In one aspect of the compositions of the present invention, each component is present in one of the two separate parts, or "components", of the composition, along with other optional ingredients as described elsewhere herein. In total, at least three components are delivered, namely, two reactive components that together form a gel, and a drug.

In another aspect of the compositions of the present invention, the components are mixed together under conditions such that they do not form a gel immediately. There components can be mixed with an activating solution (e.g., buffer, peroxide, etc.) such that a gel is rapidly formed.

The two reactive compounds and the gel matrix that forms when they are mixed together can be represented by Formula I as follows:

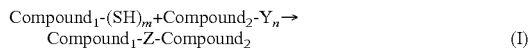

Compound$_1$ has multiple (m≥2) sulfhydryl groups (SH) that react with Compound$_2$, which has multiple (n≥2) sulfhydryl-reactive groups (Y). It should be understood that sulfhydryl groups are also "sulfhydryl reactive groups", since it is well known that sulfhydryl groups will react with one another under certain conditions. When mixed together, the two compounds become interconnected via a covalent bond (Z). However, when m+n≥5, and appropriate ratios of the two components are utilized as described elsewhere herein, Compound$_1$ and/or Compound$_2$ can form multiple attachments to Compound$_1$ and/or Compound$_2$, resulting in an interconnected three-dimensional matrix. Preferably, both compounds contain four or more functional groups, since such multifunctionality results in a gel matrix with greater overall cohesive strength. In a particularly preferred embodiment, each of the compounds is tetrafunctionally activated.

In another preferred embodiment, the compounds each have 12 functional groups. Such compounds are formed from reacting a first tetrafunctionally activated polymer with a second tetrafunctionally activated polymer, wherein the functional groups of each of the two compounds are a reaction pair, and react together to form "12-arm" functionally activated polymers. An example of such a "12-arm" compound is dodeca-sulfhydryl-PEG, 50,000 mol. wt., which is constructed from a core tetra-functional succinimide ester PEG coupled to four (exterior) tetra-functional sulfhydryl-PEG molecules. Such polymers range in size from over 10,000 mol. wt. to greater than 100,000 mol. wt. depending on the molecular weight of the tetra-functionally activated polymer starting materials.

Other types of multifunctional polymers can easily be synthesized using routine synthesis. However, care should be taken to produce multi-arm products with consistent arm lengths to avoid steric hindrance of the reactive groups.

Accordingly, activated polymers that are suitable for use in the present invention may have a variety of geometric shapes and configurations. Exemplary polymers according to the present invention, as well as methods of their manufacture and use, are described in U.S. Pat. Nos. 5,874,500; 6,051,648; 6,166,130; 6,312,725; 6,323,278; and 6,458,889.

Compound Core

As described above, each of the compounds has multiple functional groups, either sulfhydryl groups or sulfhydryl-reactive groups. The non-reactive remainder of the compound is considered to be its "core". At least one of the two compounds must have a polymer core in order to form an efficient gel matrix. When one of the compounds contains a polymer core, the other compound can be a small organic molecule with multiple sulfhydryl-reactive groups. However, for most applications, it is preferred for both compounds to have the same or a different polymer core.

The polymer core may be a synthetic polyamino acid, a polysaccharide, or a synthetic polymer. A preferred polymer core material is a synthetic hydrophilic polymer. Suitable synthetic hydrophilic polymers include, inter alia, polyalkylene oxide, such as polyethylene oxide (($CH_2CH_2O)_n$), polypropylene oxide (($CH(CH_3)CH_2O)_n$) or a polyethylene/polypropylene oxide mixture (($CH_2CH_2O)_n$—($CH(CH_3)CH_2O)_n$). A particularly preferred synthetic hydrophilic polymer is a polyethylene glycol (PEG) having a molecular weight within the range of about 100 to about 100,000 mol. wt., more preferably about 1,000 to about 20,000 mol. wt. More preferably still, when the polymer core is polyethylene glycol, it generally has a molecular weight within the range of about 7,500 to about 20,000 mol. wt. Most preferably, the polyethylene glycol has a molecular weight of approximately 10,000 mol. wt.

Multifunctionally activated polyalkylene oxides, such as polyethylene glycol, are commercially available, and are also easily prepared using known methods. For example, see Chapter 22 of Poly(ethylene Glycol) Chemistry: Biotechnical and Biomedical Applications, J. Milton Harris, ed., Plenum Press, NY (1992); and Shearwater Polymers, Inc. Catalog, Polyethylene Glycol Derivatives, Huntsville, Ala. (1997-1998). For use as a tissue sealant, the preferred combination of activated polymers is as follows: the sulfhydry-reactive group-containing compound is the tetrafunctional PEG, pentaerythritol poly(ethylene glycol)ether tetra-succinimidyl glutarate (10,000 mol. wt.); and the sulfhydryl group-containing compound is the tetrafunctional PEG, pentaerythritol poly(ethylene glycol)ether tetra-sulfhydryl (10,000 mol. wt.). In both cases, these "four-arm" PEGs are formed by ethoxylation of pentaerythritol, where each of the four chains is approximately 2,500 mol. wt., and then derivatized to introduce the functional groups onto each of the four arms. Also preferred are analogous poly(ethylene glycol)-like compounds polymerized from di-glycerol instead of pentaerythritol.

When only one of the reactive compounds comprises a polymer core, the other reactive compound is a multifunctionally active small organic molecule. Such compounds include the di-functional di-succinimidyl esters and di-maleimidyl compounds, as well as other well known commercially available compounds (Pierce Chemical Co., Rockford, Ill.). In addition, one of skill in the art could easily synthesize a low molecular weight multi-functional reactive compound using routine organic chemistry techniques. On such compound is shown in FIG. 1, which is a penta-erythritol coupled to four glutarates, with each arm capped with N-hydroxy-succinimidyl esters (NHS). Analogous compounds can be synthesized from inositol (radiating 6 arm), lactitol (9 arm) or sorbitol (linear 6-arm). The end-capped reactive group can just as easily be sulfhydryl, maleimidyl, vinyl-sulfone, vinyl, acrylate, acrylamide, etc., instead of NHS. The polymer or the small molecule can carry either reactive end group as long as there are reactive pairs in the composition such as NHS and SH, maleimidyl and SH, etc.

Reactive Groups and Matrix Linkages

In the present invention, the linkage, Z, comprises a covalent bond between the sulfur atom in the sulfhydryl group-containing compound and, the carbon or sulfur atom in the sulfhydryl-reactive group-containing compound. Accordingly, the linkage may be a thioester, a thioether, a disulfide, or the like. A wide variety of sulfhydryl-reactive groups and the types of linkages they form when reacted with sulfhydryl groups are well known in the scientific literature. For example, see Bodanszky, M., Principles of Peptide Synthesis, 2nd ed., pages 21 to 37, Springer-Verlog, Berlin (1993); and Lundbland, R. L., Chemical Reagents for Protein Modification, 2nd ed., Chapter 6, CRC Press, Boca Raton, Fla. (1991).

Figure 2:
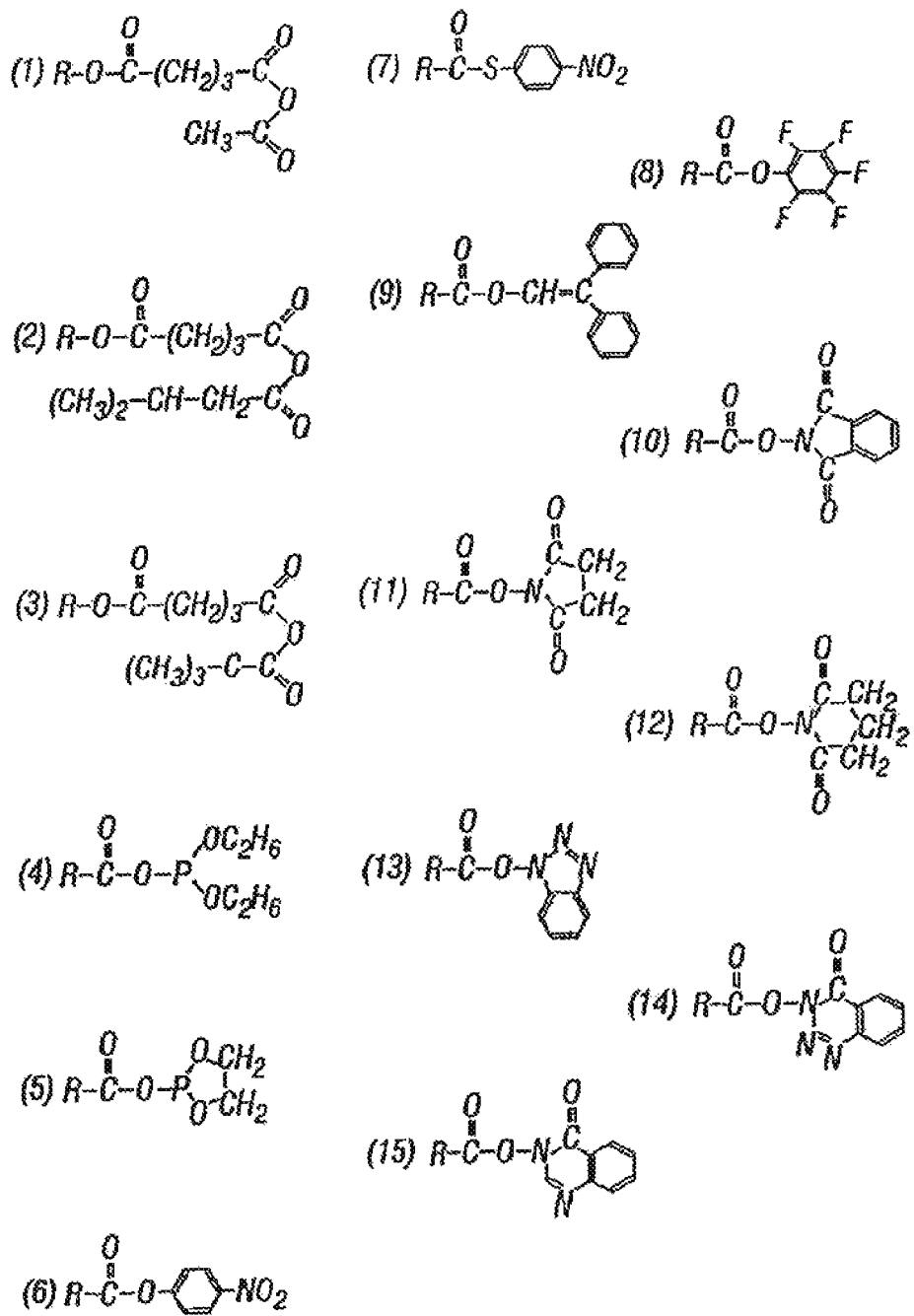
FIG. 2 depicts the structure of various sulfhydryl-reactive groups, with "R" representing the chemical structure to which the reactive group is attached.

For most applications, sulfhydryl reactive groups that react with sulfhydryl groups to form thioester linkages are preferred. Such compounds are depicted in FIG. 2 and include, inter alia, the following compounds, with the numbers in parentheses corresponding to the structures shown in FIG. 2: mixed anhydrides, such as PEG-glutaryl-acetyl-anhydride (1), PEG-glutaryl-isovaleryl-anhydride (2), PEG-glutaryl-pivalyl-anhydride (3) and related compounds as presented in Bodanszky, p. 23; Ester derivatives of phosphorus, such as structures (4) and (5); ester derivatives of p-nitrophenol (6) of p-nitrothiophenol (7), of pentafluorophenol (8), of structure (9) and related active esters as presented by Bodanszky, pp. 31-32, and Table 2; esters of substituted hydroxylamines, such as those of N-hydroxy-phthalimide (10), N-hydroxy-succinimide (11), and N-hydroxy-glutarimide (12), as well as related structures in Bodanszky; Table 3; esters of 1-hydroxy-benzotriazole (13), 3-hydroxy-3,4-dihydro-benzotriazine-4-one (14) and 3-hydroxy-3,4-dihydro-quinazoline-4-one; derivatives of carbonylimidazole; and isocyanates. With these compounds, auxiliary reagents can also be used to facilitate bond formation. For example, reagents such as 1-ethyl-3-[3-dimethylaminopropyl]carbodiimide] can be used to facilitate coupling of carboxyl groups glutarate and succinate) with sulfhydryl groups.

In addition to the sulfhydryl reactive compounds that form thioester linkages, various other compounds can be utilized that form other types of linkages. For example, compounds that contain methyl imidate derivatives form imido-thioester linkages with sulfhydryl groups. Alternatively, sulfhydryl reactive groups can be employed that form disulfide bonds with sulfhydryl groups, such as ortho pyridyl disulfide, 3-nitro-2-pyridenesulfenyl, 2-nitro-5-thiocyanobenzoic acid, 5,5'-dithio-bis(2-nitrobenzoic acid), derivatives of methane-thiosulfate, and 2,4-dinitrophenyl cysteinyl disulfides. In such instances, auxiliary reagents, such as the hydrogen peroxide or di-tert-butyl ester of azodicarboxylic acid, can be used to facilitate disulfide bond formation.

Other classes of sulfhydryl reactive groups that form thioether bonds with sulfhydryl groups include, inter alia, iodoacetamide, N-ethylmaleimide and other maleimides, including dextran maleimides, mono-bromo-bimane and related compounds, vinylsulfones, epoxides, derivatives of O-methyl-isourea, ethyleneimines, aziridines, vinyl derivatives, acrylate derivatives, acrylamide derivatives and 4-(aminosulfonyl-)-7-fluoro-2,1,3-benzoxadiazole.

Chain Extenders

Functional groups may be directly attached to the compound core, or they may be indirectly attached through a chain extender. Such chain extenders are well known in the art. See, for example, PCT WO 97/22371, which describes "linking groups" that would be suitable for use as chain extenders in the compositions of the present invention. Chain extenders are useful to avoid steric hindrance problems that are sometimes associated with the formation of direct linkages between molecules. Alternatively, chain extenders may be used to link several multifunctionally activated compounds together to make larger molecules. In a particularly preferred embodiment, the chain extender can also be used to alter the degradative properties of the compositions after administration and resultant gel formation. For example, chain extenders can be incorporated into one or both of the multifunctionally activated polymers to promote hydrolysis, to discourage hydrolysis, or to provide a site for enzymatic degradation. Chain extenders can also activate or suppress activity of sulfhydryl and sulfhydryl-reactive groups. For example, electron-withdrawing groups within one or two carbons of the sulfhydryl group would be expected to diminish its effectiveness in coupling, due to a lowering of nucleophilicity. Double-bond carbon and carbonyl carbon would be anticipated to have this effect. Bulky nearby groups for either partner are anticipated to diminish coupling rates, due to steric hindrance. Electron-withdrawing groups adjacent to the reactive carbonyl of glutaryl-N-hydroxysuccinimidyl would be anticipated to make this carbonyl carbon even more reactive with the sulfhydryl partner.

Chain extenders may provide sites for degradation, i.e., hydrolysable sites. Examples of hydrolysable chain extenders include, inter alia, alpha-hydroxy acids such as lactic acid and glycolic acid; poly(lactones) such as caprolactone, valerolactone, gamma butyl lactone and p-dioxanone; poly(amino acids); poly(anhydrides) such as glutarate and succinate; poly(orthoesters); poly(orthocarbonates) such as trimethylene carbonate; poly(phosphoesters), as well as polymers and copolymers comprising one or more of the units of the monomers lactic acid, glycolic acid, D-lactide, L-lactide, D,L-lactide, glycolide, ε-caprolactone, trimethylene carbonate, 1,4-dioxane-2-one or 1,5-dioxepan-2one. Examples of non-degradable chain extenders include, inter alia, succinimide, propionic acid and carboxymethylate. See, for example, PCT WO 99/07417. Examples of enzymatically degradable chain extenders include Leu-Gly-Pro-Ala, which is degraded by collagenase; and Gly-Pro-Lys, which is degraded by plasmin.

Gel Strength and Gel Time

The compositions of the present invention are formulated to exhibit adequate strength and rapid gel time. The elastic modulus, G', is the preferred measure of gel strength. Preferred compositions for use as tissue sealants can achieve a gel strength of about $10^3$ to $10^8$ dynes/cm$^2$, and more preferably $10^4$ to $10^7$ dynes/cm$^2$. Preferred compositions for use as hemostatic agents or for adhesion prevention have a gel strength of at least $10^2$ to $10^4$ dynes/cm$^2$ if a soft gel is desired, or $10^5$ to $10^8$ dynes/cm$^2$ if a harder matrix is desired.

The gel time of preferred formulations is less than 60 seconds, more preferably less than 30 seconds, and most preferably less than 15 seconds. The fast gel time ensures maximum material at the site to be treated and sufficient mechanical properties.

Drug

In addition to the reactive compounds described above, the compositions of the present invention include a drug. As used herein, the term "drug" refers to an organic molecule that exerts biological effects in vivo. In one aspect, the drug is in combination with Compound$_1$. In another aspect, the drug is in combination with Compound$_2$. Suitable drugs are described below. In one aspect, the drug is hydrophobic. In another aspect, the drug is hydrophyllic. One aspect of the invention involves pharmacological alteration of cellular and/or non-cellular processes involved in the development and/or maintenance of surgical adhesions. Another aspect of this invention involves pharmacological alteration of cellular and/or non-cellular processes involved in the development and/or maintenance of restenosis. Thus, pharmacological agents (i.e., drugs) within the scope of this invention include but are not limited to those which inhibit one or a combination of processes including but not limited to cell division, cell secretion, cell migration, cell adhesion, cytokine, chemokine (or other inflammatory activator) production and/or release, angiogenesis, and/or free radical formation and/or release. Drugs within the scope of this invention may inhibit or affect other processes involved in the scarring process.

In addition, an aspect of this invention involves pharmacological alteration of cellular and/or non-cellular processes which increase the development of fibrosis. Thus, pharmacological agents (i.e., drugs) within the scope of this invention include but are not limited to those which increase one or a combination of processes including but not limited to cell division, cell secretion, cell migration, cell adhesion, cytokine, chemokine (or other inflammatory activator) production and/or release, angiogenesis, and/or free radical formation and/or release. Drugs within the scope of this invention may increase or affect other processes involved in the scarring process.

Thus, while the non-drug loaded formulation can act as a sealant and/or hemostatic agent and/or adhesion prevention agent, the addition of a drug can effect an increase or decrease in fibrosis, and/or result in tissue augmentation and/or increase or reduction in surgical adhesions depending on the drug mechanism. For example, a drug which decreases fibrosis will be expected to reduce surgical adhesions. Furthermore, the drug-loaded formulation may increase the sealant and/or hemostatic properties of the formulation, especially when the agent acts to increase fibrosis.

One aspect of the invention involves pharmacological alteration of cellular and/or non-cellular processes involved in the development and/or maintenance of surgical adhesions or restenosis or in more general terms inhibit one or more processes involved in fibrosis. Thus, pharmacological agents within the scope of this invention include but are not limited to those which inhibit one or a combination of processes such as cell division, cell secretion, cell migration, cell adhesion, extracellular matrix production, cytokine (e.g., TNF alpha, IL-1, IL-6), or other inflammatory activator, e.g., chemokines (e.g., MCP-1 or IL-8)) production and/or release, angiogenesis, and/or free radical formation and/or release.

Suitable fibrosis, adhesion or stenosis-inhibiting agents may be readily determined based upon the in vitro and in vivo (animal) models such as those provided in Examples 29-33. Numerous fibrosis, adhesion and/or stenosis-inhibiting therapeutic compounds have been identified that are of utility in the invention including:

1. Angiogenesis Inhibitors

In one embodiment, the pharmacologically active compound is an angiogenesis inhibitor (e.g., 2-ME (NSC-659853), PI-88 (D-Mannose, 0-6-O-phosphono-Alpha-D-mannopyranosyl-(1-3)-O-Alpha-D-mannopyranosyl-(1-3)-O-Alpha-D-mannopyranosyl-(1-3)-O-Alpha-D-mannopyranosyl-(1-2)-hydrogen sulphate [CAS]), thalidomide (1H-Isoindole-1,3(2H)-dione, 2-(2,6-dioxo-3-piperidinyl)-[CAS]), CDC-394, CC-5079, ENMD-0995 (S-3-amino-phthalidoglutarimide), AVE-8062A, Vatalanib, SH-268, Halofuginone hydrobromide)) or an analogue or derivative thereof.

2. 5-Lipoxygenase Inhibitors & Antagonists

In another embodiment, the pharmacologically active compound is a 5-lipoxygenase inhibitor or antagonist (e.g., licofelone (ML3000), 2-uredo thiophene/2 amino thiophene, 15-deoxy-Prostaglandin J2, Wy-50295 (2-Naphthaleneacetic acid, Alpha-methyl-6-(2-quinolinylmethoxy)-, (S)-[CAS]), ONO-LP-269 (2,11,14-Eicosatrienamide, N-[4-hydroxy-2-(1H-tetrazol-5-yl)-8-quinolinyl]-, (E,Z,Z)-[CAS]), licofelone (1H-Pyrrolizine-5-acetic acid, 6-(4-chlorophenyl)-2,3-dihydro-2,2-dimethyl-7-phenyl-[CAS]), CMI-568 (Urea, N-butyl-N-hydroxy-N'-[4-[3-(methylsulfonyl)-2-propoxy-5-[tetrahydro-5-(3,4,5-trimethoxyphenyl)-2-furanyl]phenoxy]butyl]-,trans-[CAS]), IP-751 ((3R,4R)-(delta6)-THC-DMH-11-oic acid), PF-5901 (Benzenemethanol, Alpha-pentyl-3-(2-quinolinylmethoxy)-[CAS]), LY-293111 (Benzoic acid, 2-[3-[3-[(5-ethyl-4'-fluoro-2-hydroxy[1,1'-biphenyl]-4-yl)oxy]propoxy]-2-propylphenoxy]-[CAS]), RG-5901-A (Benzenemethanol, Alpha-pentyl-3-(2-quinolinylmethoxy)-, hydrochloride [CAS]), rilopirox (2(1H)-Pyridinone, 6-[[4-(4-chlorophenoxy)phenoxy]methyl]-1-hydroxy-4-methyl-[CAS]), L-674636 (Acetic acid, ((4-(4-chlorophenyl)-1-(4-(2-quinolinylmethoxy)phenyl)butyl)thio)-ASD, 7-[[3-(4-methoxy-tetrahydro-2H-pyran-4-yl)phenyl]methoxy]-4-phenylnaphtho[2,3-c]furan-1(3H)-one, MK-886 (1H-Indole-2-propanoic acid, 1-[(4-chlorophenyl)methyl]-3-[(1,1-dimethylethyl)thio]-Alpha,Alpha-dimethyl-5-(1-methylethyl)-[CAS]), quiflapon (1H-Indole-2-propanoic acid, 1-[(4-chlorophenyl)methyl]-3-[(1,1-dimethylethyl)thio]-Alpha,Alpha-dimethyl-5-(2-quinolinylmethoxy)-[CAS]), quiflapon (1H-Indole-2-propanoic acid, 1-[(4-chlorophenyl)methyl]-3-[(1,1-dimethylethyl)thio]-Alpha,Alpha-dimethyl-5-(2-quinolinylmethoxy)-[CAS]), docebenone (2,5-Cyclohexadiene-1,4-dione, 2-(12-hydroxy-5,10-dodecadiynyl)-3,5,6-trimethyl-[CAS]), zileuton (Urea, N-(1-benzo[b]thien-2-ylethyl)-N-hydroxy-[CAS])) or an analogue or derivative thereof.

3. Chemokine Receptor Antagonists CCR (1, 3, & 5)

In another embodiment, the pharmacologically active compound is a chemokine receptor antagonist (e.g., AMD-3100 (Anormed), ONO-4128 (1,4,9-Triazaspiro(5.5)undecane-2,5-dione, 1-butyl-3-(cyclohexylmethyl)-9-(2,3-dihydro-1,4-benzodioxin-6-yl)methyl-[CAS]), L-381, CT-112 (L-Arginine, L-threonyl-L-threonyl-L-seryl-L-glutaminyl-L-valyl-L-arginyl-L-prolyl-[CAS]), AS-900004, SCH-C, ZK-811752, PD-172084, UK-427857, SB-380732, vMIP II, SB-265610, DPC-168, TAK-779 (N,N-Dimethyl-N-[4-[2-(4-methylphenyl)-6,7-dihydro-5H-benzocyclohepten-8-yl-carboxamido]benzyl]tetrahydro-2H-pyran-4-aminium chloride), TAK-220, KRH-1120) or an analogue or derivative thereof.

4. Cell Cycle Inhibitors

In another embodiment, the pharmacologically active compound is a cell cycle inhibitor or an analogue or derivative thereof. In related embodiments, the cell-cycle inhibitor is a taxane (e.g., paclitaxel, or an analogue or derivative thereof), an antimetabolite, an alkylating agent, or a vinca alkaloid. In another embodiment, the cell-cycle inhibitor is camptothecin or an analogue or derivative thereof. Other suitable compounds include mitoxantrone, etoposide, 5-fluorouracil, doxorubicin, methotrexate, Peloruside A—a microtubule stabilizing agent, Mitomycin-C, and CDK-2 inhibitors.

Figure 3:
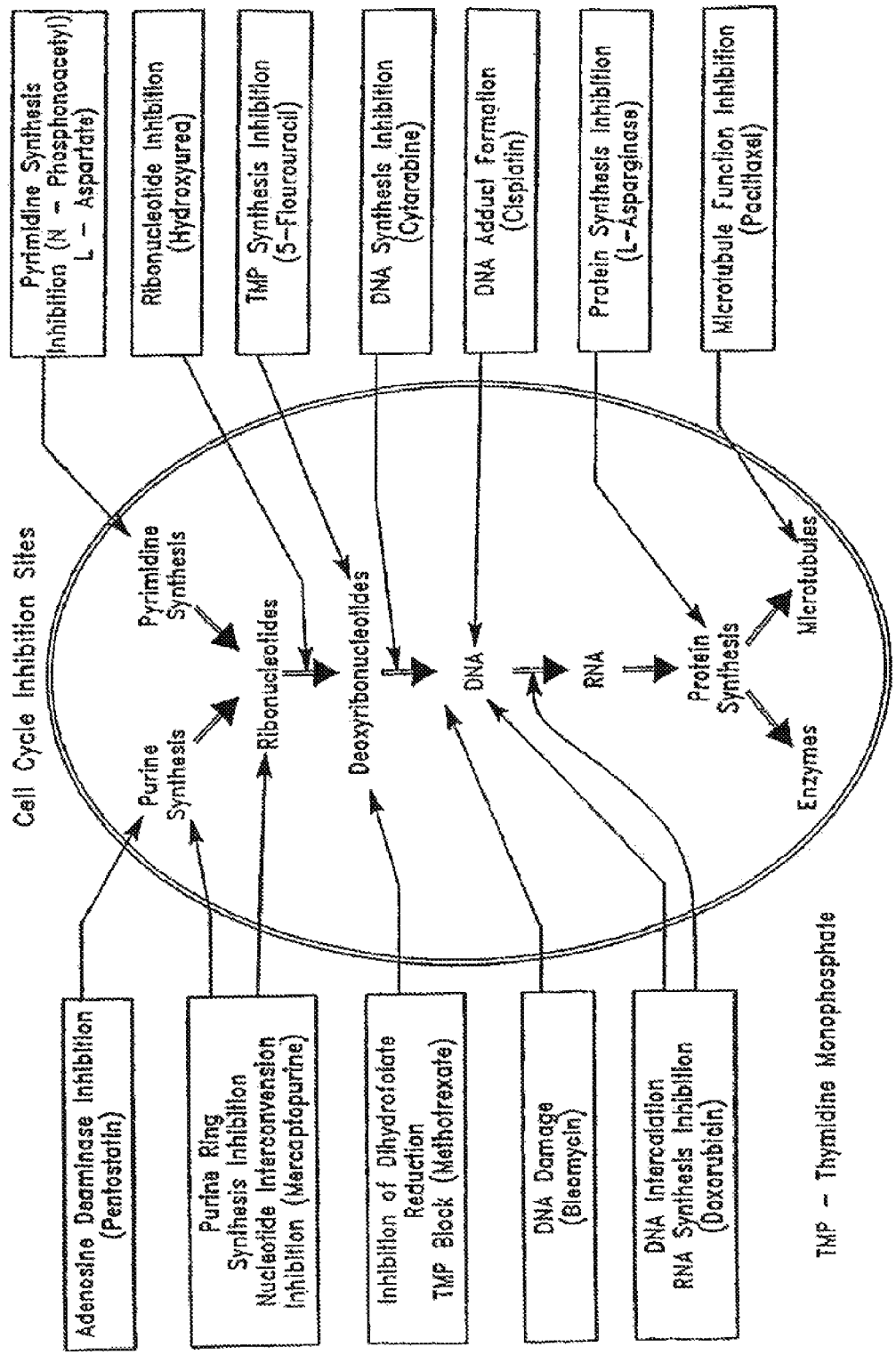
FIG. 3 is a schematic illustration showing sites of action within a biological pathway where Cell Cycle Inhibitors may act to inhibit the cell cycle.

"Cell Cycle Inhibitor" as used herein refers to any protein, peptide, chemical or other molecule which delays or impairs a dividing cell's ability to progress through the cell cycle and replicate. A wide variety of methods may be utilized to determine the ability of a compound to inhibit the cell cycle including univariate analysis of cellular DNA content and multiparameter analysis. A Cell Cycle Inhibitor may act to inhibit the cell cycle at any of the steps of the biological pathways shown in FIG. 3, as well as at other possible steps in other biological pathways. In addition, it should be understood that while a single cell cycle agent is often referred to, that this in fact should be understood to include two or more cell cycle agents, as more than one cell cycle agent may be utilized within the compositions, methods and/or devices described herein (e.g., two cell-cycle inhibitors may be selected that act on different steps shown in FIG. 3.

A wide variety of cell cycle inhibitory agents can be utilized, either with or without a carrier (e.g., a polymer or ointment or vector), within the context of the present invention. Representative examples of such agents include taxanes (e.g., paclitaxel (discussed in more detail below) and docetaxel) (Schiff et al., *Nature* 277:665-667, 1979; Long and Fairchild, *Cancer Research* 54:4355-4361, 1994; Ringel and Horwitz, J. *Nat'l Cancer Inst.* 83(4):288-291, 1991; Pazdur et al., *Cancer Treat. Rev.* 19(40):351-386, 1993), Etanidazole, Nimorazole (B. A. Chabner and D. L. Longo. Cancer Chemotherapy and Biotherapy—Principles and Practice. Lippincott-Raven Publishers, New York, 1996, p. 554), perfluorochemicals with hyperbaric oxygen, transfusion, erythropoietin, BW12C, nicotinamide, hydralazine, BSO, WR-2721, IudR, DUdR, etanidazole, WR-2721, BSO, monosubstituted keto-aldehyde compounds (L. G. Egyud. Keto-aldehyde-amine addition products and method of making same. U.S. Pat. No. 4,066,650, Jan. 3, 1978), nitroimidazole (K. C. Agrawal and M. Sakaguchi. Nitroimidazole radiosensitizers for Hypoxic tumor cells and compositions thereof. U.S. Pat. No. 4,462,992, Jul. 31, 1984), 5-substituted-4-nitroimidazoles (Adams et al., *Int. J. Radiat. Biol. Relat. Stud. Phys., Chem. Med.* 40(2):153-61, 1981), SR-2508 (Brown et al., *Int. J. Radiat. Oncol., Biol. Phys.* 7(6):695-703, 1981), 2H-isoindolediones (J. A. Myers, 2H-Isoindolediones, their synthesis and use as radiosensitizers. U.S. Pat. No. 4,494,547, Jan. 22, 1985), chiral [[(2-bromoethyl)-amino]methyl]-nitro-1H-imidazole-1-ethanol (V. G. Beylin, et al., Process for preparing chiral [[(2-bromoethyl)-amino]methyl]-nitro-1H-imidazole-1-ethanol and related compounds. U.S. Pat. No. 5,543,527, Aug. 6, 1996; U.S. Pat. No. 4,797,397; Jan. 10, 1989; U.S. Pat. No. 5,342,959, Aug. 30, 1994), nitroaniline derivatives (W. A. Denny, et al. Nitroaniline derivatives and their use as anti-tumor agents. U.S. Pat. No. 5,571,845, Nov. 5, 1996), DNA-affinic hypoxia selective cytotoxins (M. V. Papadopoulou-Rosenzweig. DNA-affinic hypoxia selective cytotoxins. U.S. Pat. No. 5,602,142, Feb. 11, 1997), halogenated DNA ligand (R. F. Martin. Halogenated DNA ligand radiosensitizers for cancer therapy. U.S. Pat. No. 5,641,764, Jun. 24, 1997), 1,2,4 benzotriazine oxides (W. W. Lee et al. 1,2,4-benzotriazine oxides as radiosensitizers and selective cytotoxic agents. U.S. Pat. No. 5,616,584, Apr. 1, 1997; U.S. Pat. No. 5,624,925, Apr. 29, 1997; Process for Preparing 1,2,4 Benzotriazine oxides. U.S. Pat. No. 5,175,287, Dec. 29, 1992), nitric oxide (J. B. Mitchell et al., Use of Nitric oxide releasing compounds as hypoxic cell radiation sensitizers. U.S. Pat. No. 5,650,442, Jul. 22, 1997), 2-nitroimidazole derivatives (M. J. Suto et al. 2-Nitroimidazole derivatives useful as radiosensitizers for hypoxic tumor cells. U.S. Pat. No. 4,797,397, Jan. 10, 1989; T. Suzuki. 2-Nitroimidazole derivative, production thereof, and radiosensitizer containing the same as active ingredient. U.S. Pat. No. 5,270,330, Dec. 14, 1993; T. Suzuki et al. 2-Nitroimidazole derivative, production thereof, and radiosensitizer containing the same as active ingredient. U.S. Pat. No. 5,270,330, Dec. 14, 1993; T. Suzuki. 2-Nitroimidazole derivative, production thereof and radiosensitizer containing the same as active ingredient; Patent No. EP 0 513 351 B1, Jan. 24, 1991), fluorine-containing nitroazole derivatives (T. Kagiya. Fluorine-containing nitroazole derivatives and radiosensitizer comprising the same. U.S. Pat. No. 4,927,941, May 22, 1990), copper (M. J. Abrams. Copper Radiosensitizers. U.S. Pat. No. 5,100,885, Mar. 31, 1992), combination modality cancer therapy (D. H. Picker et al. Combination modality cancer therapy. U.S. Pat. No. 4,681,091, Jul. 21, 1987). 5-CldC or (d)H$_4$U or 5-halo-2'-halo-2'-deoxy-cytidine or -uridine derivatives (S. B. Greer. Method and Materials for sensitizing neoplastic tissue to radiation. U.S. Pat. No. 4,894,364 Jan. 16, 1990), platinum complexes (K. A. Skov. Platinum Complexes with one radiosensitizing ligand. U.S. Pat. No. 4,921,963. May 1, 1990; K. A. Skov. Platinum Complexes with one radiosensitizing ligand. Patent No. EP 0 287 317 A3), fluorine-containing nitroazole (T. Kagiya, et al. Fluorine-containing nitroazole derivatives and radiosensitizer comprising the same. U.S. Pat. No. 4,927,941. May 22, 1990), benzamide (W. W. Lee. Substituted Benzamide Radiosensitizers. U.S. Pat. No. 5,032,617, Jul. 16, 1991), autobiotics (L. G. Egyud. Autobiotics and their use in eliminating nonself cells in vivo. U.S. Pat. No. 5,147,652. Sep. 15, 1992), benzamide and nicotinamide (W. W. Lee et al. Benzamide and Nictoinamide Radiosensitizers. U.S. Pat. No. 5,215,738, Jun. 1, 1993), acridine-intercalator (M. Papadopoulou-Rosenzweig. Acridine Intercalator based hypoxia selective cytotoxins. U.S. Pat. No. 5,294,715, Mar. 15, 1994), fluorine-containing nitroimidazole (T. Kagiya et al. Fluorine containing nitroimidazole compounds. U.S. Pat. No. 5,304,654, Apr. 19, 1994), hydroxylated texaphyrins (J. L. Sessler et al. Hydroxylated texaphrins. U.S. Pat. No. 5,457, 183, Oct. 10, 1995), hydroxylated compound derivative (T. Suzuki et al. Heterocyclic compound derivative, production thereof and radiosensitizer and antiviral agent containing said derivative as active ingredient. Publication Number 011106775 A (Japan), Oct. 22, 1987; T. Suzuki et al. Heterocyclic compound derivative, production thereof and radiosensitizer, antiviral agent and anti cancer agent containing said derivative as active ingredient. Publication Number 01139596 A (Japan), Nov. 25, 1987; S. Sakaguchi et al. Heterocyclic compound derivative, its production and radiosensitizer containing said derivative as active ingredient; Publication Number 63170375 A (Japan), Jan. 7, 1987), fluorine containing 3-nitro-1,2,4-triazole (T. Kagitani et al. Novel fluorine-containing 3-nitro-1,2,4-triazole and radiosensitizer containing same compound. Publication Number 02076861 A (Japan), Mar. 31, 1988), 5-thiotretrazole derivative or its salt (E. Kano et al. Radiosensitizer for Hypoxic cell. Publication Number 61010511 A (Japan), Jun. 26, 1984), Nitrothiazole (T. Kagitani et al. Radiation-sensitizing agent. Publication Number 61167616 A (Japan) Jan. 22, 1985), imidazole derivatives (S. Inayma et al. Imidazole derivative. Publication Number 6203767 A (Japan) Aug. 1, 1985; Publication Number 62030768 A (Japan) Aug. 1, 1985; Publication Number 62030777 A (Japan) Aug. 1, 1985), 4-nitro-1,2,3-triazole (T. Kagitani et al. Radiosensitizer. Publication Number 62039525 A (Japan), Aug. 15, 1985), 3-nitro-1,2,4-triazole (T. Kagitani et al. Radiosensitizer. Publication Number 62138427 A (Japan), Dec. 12, 1985), Carcinostatic action regulator (H. Amagase. Carcinostatic action regulator. Publication Number 63099017 A (Japan), Nov. 21, 1986), 4,5-dinitroimidazole derivative (S. Inayama. 4,5-Dinitroimidazole derivative. Publication Number 63310873 A (Japan) Jun. 9, 1987), nitrotriazole Compound (T. Kagitanil. Nitrotriazole Compound. Publication Number 07149737 A (Japan) Jun. 22, 1993), cisplatin, doxorubicin, misonidazole, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide (I. F. Tannock. Review Article: Treatment of Cancer with Radiation and Drugs. *Journal of Clinical Oncology* 14(12):3156-3174, 1996), camptothecin (Ewend M. G. et al. Local delivery of chemotherapy and concurrent external beam radiotherapy prolongs survival in metastatic brain tumor models. *Cancer Research* 56(22):5217-5223, 1996) and paclitaxel (Tishler R.

B. et al. Taxol: a novel radiation sensitizer. *International Journal of Radiation Oncology and Biological Physics* 22(3): 613-617, 1992).

A number of the above-mentioned cell cycle inhibitors also have a wide variety of analogues and derivatives, including, but not limited to, cisplatin, cyclophosphamide, misonidazole, tiripazamine, nitrosourea, mercaptopurine, methotrexate, fluorouracil, epirubicin, doxorubicin, vindesine and etoposide. Analogues and derivatives include $(CPA)_2Pt$ [DOLYM] and (DACH)Pt[DOLYM] cisplatin (Choi et al., *Arch. Pharmacal Res.* 22(2):151-156, 1999), Cis-[PtCl$_2$(4,7-H-5-methyl-7-oxo]1,2,4[triazolo[1,5-a]pyrimidine)$_2$] (Navarro et al., *J. Med. Chem.* 41(3):332-338, 1998), [Pt(cis-1,4-DACH)(trans-Cl$_2$)(CBDCA)].½MeOH cisplatin (Shamsuddin et al., *Inorg. Chem.* 36(25):5969-5971, 1997), 4-pyridoxate diammine hydroxy platinum (Tokunaga et al., *Pharm. Sci.* 3(7):353-356, 1997), Pt(II) . . . Pt(II) (Pt$_2$ [NHCHN(C(CH$_2$)(CH$_3$))]$_4$) (Navarro et al., *Inorg. Chem.* 35(26):7829-7835, 1996), 254-S cisplatin analogue (Koga et al., *Neurol. Res.* 18(3):244-247, 1996), o-phenylenediamine ligand bearing cisplatin analogues (Koeckerbauer & Bednarski, *J. Inorg. Biochem.* 62(4):281-298, 1996), trans, cis-[Pt(OAc)$_2$I$_2$(en)] (Kratochwil et al., *J. Med. Chem.* 39(13):2499-2507, 1996), estrogenic 1,2-diarylethylenediamine ligand (with sulfur-containing amino acids and glutathione) bearing cisplatin analogues (Bednarski, *J. Inorg. Biochem.* 62(1):75, 1996), cis-1,4-diaminocyclohexane cisplatin analogues (Shamsuddin et al., *J. Inorg. Biochem.* 61(4):291-301, 1996), 5' orientational isomer of cis-[Pt(NH$_3$)(4-aminoTEMP-O){d (GpG)}] (Dunham & Lippard, *J. Am. Chem. Soc.* 117(43) 10702-12, 1995), chelating diamine-bearing cisplatin analogues (Koeckerbauer & Bednarski, *J. Pharm. Sci.* 84(7): 819-23, 1995), 1,2-diarylethyleneamine ligand-bearing cisplatin analogues (Otto et al., *J. Cancer Res. Clin. Oncol.* 121(1):31-8, 1995), (ethylenediamine)platinum(II) complexes (Pasini et al., *J. Chem. Soc., Dalton Trans.* 4:579-85, 1995), CI-973 cisplatin analogue (Yang et al., *Int. J. Oncol.* 5(3):597-602, 1994), cis-diamminedichloroplatinum(II) and its analogues cis-1,1-cyclobutanedicarbosylato(2R)-2-methyl-1,4-butanediam-mineplatinum(II) and cis-diammine (glycolato)platinum (Claycamp & Zimbrick, *J. Inorg. Biochem.* 26(4):257-67, 1986; Fan et al., *Cancer Res.* 48(11): 3135-9, 1988; Heiger-Bernays et al., *Biochemistry* 29(36): 8461-6, 1990; Kikkawa et al., *J. Exp. Clin. Cancer Res.* 12(4):233-40, 1993; Murray et al., *Biochemistry* 31(47):11812-17, 1992; Takahashi et al., *Cancer Chemother. Pharmacol.* 33(1):31-5, 1993), cis-amine-cyclohexylamine-dichloroplatinum(II) (Yoshida et al., *Biochem. Pharmacol.* 48(4):793-9, 1994), gem-diphosphonate cisplatin analogues (FR 2683529), (meso-1,2-bis(2,6-dichloro-4-hydroxyphenyl)ethylenediamine)dichloroplatinum(II) (Bednarski et al., *J. Med. Chem.* 35(23):4479-85, 1992), cisplatin analogues containing a tethered dansyl group (Hartwig et al., *J. Am. Chem. Soc.* 114(21):8292-3, 1992), platinum(II) polyamines (Siegmann et al., *Inorg. Met.-Containing Polym. Mater.*, (*Proc. Am. Chem. Soc. Int. Symp.*), 335-61, 1990), cis-(3H) dichloro(ethylenediamine)platinum(II) (Eastman, *Anal. Biochem.* 197(2):311-15, 1991), trans-diamminedichloroplatinum(II) and cis-(Pt(NH$_3$)$_2$(N$_3$-cytosine)Cl) (Belton & Lippard, *Biophys. Chem.* 35(2-3):179-88, 1990), 3H-cis-1,2-diaminocyclohexanedichloroplatinum(II) and 3H-cis-1,2-diaminocyclohexane-malonatoplatinum (II) (Oswald et al., *Res. Commun. Chem. Pathol. Pharmacol.* 64(1):41-58, 1989), diaminocarboxylatoplatinum (EPA 296321), trans-(D,1)-1,2-diaminocyclohexane carrier ligand-bearing platinum analogues (Wyrick & Chaney, *J. Labelled Compd. Radiopharm.* 25(4):349-57, 1988), aminoalkylaminoanthraquinone-derived cisplatin analogues (Kitov et al., *Eur. J. Med. Chem.* 23(4):381-3, 1988), spiroplatin, carboplatin, iproplatin and JM40 platinum analogues (Schroyen et al., *Eur. J. Cancer Clin. Oncol.* 24(8):1309-12, 1988), bidentate tertiary diamine-containing cisplatinum derivatives (Orbell et al., *Inorg. Chim. Acta* 152(2):125-34, 1988), platinum(II), platinum(IV) (Liu & Wang, *Shandong Yike Daxue Xuebao* 24(1):35-41, 1986), cis-diammine(1,1-cyclobutanedicarboxylato-)platinum(II) (carboplatin, JM8) and ethylenediammine-malonatoplatinum(II) (JM40) (Begg et al., *Radiother. Oncol.* 9(2):157-65, 1987), JM8 and JM9 cisplatin analogues (Harstrick et al., *Int. J. Androl.* 10(1); 139-45, 1987), (NPr4)$_2$((PtCL4).cis-(PtCl2-(NH2Me)$_2$)) (Brammer et al., *J. Chem. Soc., Chem. Commun.* 6:443-5, 1987), aliphatic tricarboxylic acid platinum complexes (EPA 185225), cis-dichloro(amino acid) (tert-butylamine)platinum(II) complexes (Pasini & Bersanetti, *Inorg. Chim. Acta* 107(4):259-67, 1985); 4-hydroperoxycylcophosphamide (Ballard et al., *Cancer Chemother. Pharmacol.* 26(6):397-402, 1990), acyclouridine cyclophosphamide derivatives (Zakerinia et al., *Helv. Chim. Acta* 73(4): 912-15, 1990), 1,3,2-dioxa- and -oxazaphosphorinane cyclophosphamide analogues (Yang et al., *Tetrahedron* 44(20): 6305-14, 1988), C5-substituted cyclophosphamide analogues (Spada, University of Rhode Island Dissertation, 1987), tetrahydrooxazine cyclophosphamide analogues (Valente, University of Rochester Dissertation, 1988), phenyl ketone cyclophosphamide analogues (Hales et al., *Teratology* 39(1):31-7, 1989), phenylketophosphamide cyclophosphamide analogues (Ludeman et al., *J. Med. Chem.* 29(5):716-27, 1986), ASTA Z-7557 cyclophosphamide analogues (Evans et al., *Int. J. Cancer* 34(6):883-90, 1984), 3-(1-oxy-2,2,6,6-tetramethyl-4-piperidinyl)cyclophosphamide (Tsui et al., *J. Med. Chem.* 25(9):1106-10, 1982), 2-oxobis(2-β-chloroethylamino)-4-,6-dimethyl-1,3,2-oxazaphosphorinane cyclophosphamide (Carpenter et al., *Phosphorus Sulfur* 12(3):287-93, 1982), 5-fluoro- and 5-chlorocyclophosphamide (Foster et al., *J. Med. Chem.* 24(12):1399-403, 1981), cis- and trans-4-phenylcyclophosphamide (Boyd et al., *J. Med. Chem.* 23(4):372-5, 1980), 5-bromocyclophosphamide, 3,5-dehydrocyclophosphamide (Ludeman et al., *J. Med. Chem.* 22(2):151-8, 1979), 4-ethoxycarbonyl cyclophosphamide analogues (Foster, *J. Pharm. Sci.* 67(5):709-10, 1978), arylaminotetrahydro-2H-1,3,2-oxazaphosphorine 2-oxide cyclophosphamide analogues (Hamacher, *Arch. Pharm.* (Weinheim, Ger.) 310(5):J, 428-34, 1977), NSC-26271 cyclophosphamide analogues (Montgomery & Struck, *Cancer Treat. Rep.* 60(4):J381-93, 1976), benzo annulated cyclophosphamide analogues (Ludeman & Zon, *J. Med. Chem.* 18(12):J1251-3, 1975), 6-trifluoromethylcyclophosphamide (Farmer & Cox, *J. Med. Chem.* 18(11):J1106-10, 1975), 4-methylcyclophosphamide and 6-methycyclophosphamide analogues (Cox et al., *Biochem. Pharmacol.* 24(5):J599-606, 1975); FCE 23762 doxorubicin derivative (Quaglia et al., *J. Liq. Chromatogr.* 17(18):3911-3923, 1994), annamycin (Zou et al., *J. Pharm. Sci.* 82(11):1151-1154, 1993), ruboxyl (Rapoport et al., *J. Controlled Release* 58(2):153-162, 1999), anthracycline disaccharide doxorubicin analogue (Pratesi et al., *Clin. Cancer Res.* 4(11):2833-2839, 1998), N-(trifluoroacetyl)doxorubicin and 4'-O-acetyl-N-(trifluoroacetyl)doxorubicin (Berube & Lepage, *Synth. Commun.* 28(6):1109-1116, 1998), 2-pyrrolinodoxorubicin (Nagy et al., *Proc. Nat'l Acad. Sci. U.S.A.* 95(4):1794-1799, 1998), disaccharide doxorubicin analogues (Arcamone et al., *J. Nat'l Cancer Inst.* 89(16):1217-1223, 1997), 4-demethoxy-7-O-[2,6-dideoxy-4-O-(2,3,6-trideoxy-3-amino-α-L-lyxo-hexopyranosyl)-α-L-lyxo-hexopyranosyl]adriamicinone doxorubicin disaccharide analogue(Monteagudo et al., *Carbohydr. Res.* 300(1):11-

16, 1997), 2-pyrrolinodoxorubicin (Nagy et al., *Proc. Nat'l Acad. Sci. U.S.A.* 94(2):652-656, 1997), morpholinyl doxorubicin analogues (Duran et al., *Cancer Chemother. Pharmacol.* 38(3):210-216, 1996), enaminomalonyl-β-alanine doxorubicin derivatives (Seitz et al., *Tetrahedron Lett.* 36(9):1413-16, 1995), cephalosporin doxorubicin derivatives (Vrudhula et al., *J. Med. Chem.* 38(8):1380-5, 1995), hydroxyrubicin (Solary et al., *Int. J. Cancer* 58(1):85-94, 1994), methoxymorpholino doxorubicin derivative (Kuhl et al., *Cancer Chemother. Pharmacol.* 33(1):10-16, 1993), (6-maleimidocaproyl)hydrazone doxorubicin derivative (Willner et al., *Bioconjugate Chem.* 4(6):521-7, 1993), N-(5,5-diacetoxypent-1-yl)doxorubicin (Chemf & Farquhar, *J. Med. Chem.* 35(17):3208-14, 1992), FCE 23762 methoxymorpholinyl doxorubicin derivative (Ripamonti et al., *Br. J. Cancer* 65(5):703-7, 1992), N-hydroxysuccinimide ester doxorubicin derivatives (Demant et al., *Biochim. Biophys. Acta* 1118(1):83-90, 1991), polydeoxynucleotide doxorubicin derivatives (Ruggiero et al., *Biochim. Biophys. Acta* 1129(3):294-302, 1991), morpholinyl doxorubicin derivatives (EPA 434960), mitoxantrone doxorubicin analogue (Krapcho et al., *J. Med. Chem.* 34(8):2373-80. 1991), AD198 doxorubicin analogue (Traganos et al., *Cancer Res.* 51(14):3682-9, 1991), 4-demethoxy-3'-N-trifluoroacetyldoxorubicin (Horton et al., *Drug Des. Delivery* 6(2):123-9, 1990), 4'-epidoxorubicin (Drzewoski et al., *Pol. J. Pharmacol. Pharm.* 40(2):159-65, 1988; Weenen et al., *Eur. J. Cancer Clin. Oncol.* 20(7):919-26, 1984), alkylating cyanomorpholino doxorubicin derivative (Scudder et al., *J. Nat'l Cancer Inst.* 80(16):1294-8, 1988), deoxydihydroiodooxorubicin (EPA 275966), adriblastin (Kalishevskaya et al., *Vestn. Mosk. Univ.,* 16(Biol. 1):21-7, 1988), 4'-deoxydoxorubicin (Schoelzel et al., *Leuk. Res.* 10(12):1455-9, 1986), 4-demethoxy-4'-o-methyldoxorubicin (Giuliani et al., *Proc. Int. Congr. Chemother.* 16:285-70-285-77, 1983), 3'-deamino-3'-hydroxydoxorubicin (Horton et al., *J. Antibiot.* 37(8):853-8, 1984), 4-demethyoxy doxorubicin analogues (Barbieri et al., *Drugs Exp. Clin. Res.* 10(2):85-90, 1984), N-L-leucyl doxorubicin derivatives (Trouet et al., Anthracyclines (*Proc. Int. Symp. Tumor Pharmacother.*), 179-81, 1983), 3'-deamino-3'-(4-methoxy-1-piperidinyl)doxorubicin derivatives (U.S. Pat. No. 4,314,054), 3'-deamino-3'-(4-mortholinyl)doxorubicin derivatives (U.S. Pat. No. 4,301,277), 4'-deoxydoxorubicin and 4'-o-methyldoxorubicin (Giuliani et al., *Int. J. Cancer* 27(1):5-13, 1981), aglycone doxorubicin derivatives (Chan & Watson, *J. Pharm. Sci.* 67(12):1748-52, 1978), SM 5887 (*Pharma Japan* 1468:20, 1995), MX-2 (*Pharma Japan* 1420:19, 1994), 4'-deoxy-13(S)-dihydro-4'-iododoxorubicin (EP 275966), morpholinyl doxorubicin derivatives (EPA 434960), 3'-deamino-3'-(4-methoxy-1-piperidinyl)doxorubicin derivatives (U.S. Pat. No. 4,314,054), doxorubicin-14-valerate, morpholinodoxorubicin (U.S. Pat. No. 5,004,606), 3'-deamino-3'-(3"-cyano-4"-morpholinyl doxorubicin; 3'-deamino-3'-(3"-cyano-4"-morpholinyl)-13-dihydroxorubicin; (3'-deamino-3'-(3"-cyano-4"-morpholinyl)daunorubicin; 3'-deamino-3'-(3"-cyano-4"-morpholinyl)-3-dihydrodaunorubicin; and 3'-deamino-3'-(4"-morpholinyl-5-iminodoxorubicin and derivatives (U.S. Pat. No. 4,585,859), 3'-deamino-3'-(4-methoxy-1-piperidinyl)doxorubicin derivatives (U.S. Pat. No. 4,314,054) and 3-deamino-3-(4-morpholinyl)doxorubicin derivatives (U.S. Pat. No. 4,301,277); 4,5-dimethylmisonidazole (Born et al., *Biochem. Pharmacol.* 43(6):1337-44, 1992), azo and azoxy misonidazole derivatives (Gattavecchia & Tonelli, *Int. J. Radiat. Biol. Relat. Stud. Phys., Chem. Med.* 45(5):469-77, 1984); RB90740 (Wardman et al., *Br. J. Cancer,* 74 *Suppl.* (27):S70-S74, 1996); 6-bromo and 6-chloro-2,3-dihydro-1,4-benzothiazines nitrosourea derivatives (Rai et al., *Heterocycl. Commun.* 2(6):587-592, 1996), diamino acid nitrosourea derivatives (Dulude et al., *Bioorg. Med. Chem. Lett.* 4(22):2697-700, 1994; Dulude et al., *Bioorg. Med. Chem.* 3(2):151-60, 1995), amino acid nitrosourea derivatives (Zheleva et al., *Pharmazie* 50(1):25-6, 1995), 3',4'-didemethoxy-3',4'-dioxo-4-deoxypodophyllotoxin nitrosourea derivatives (Miyahara et al., *Heterocycles* 39(1):361-9, 1994), ACNU (Matsunaga et al., *Immunopharmacology* 23(3):199-204, 1992), tertiary phosphine oxide nitrosourea derivatives (Guguva et al., *Pharmazie* 46(8):603, 1991), sulfamerizine and sulfamethizole nitrosourea derivatives (Chiang et al., *Zhonghua Yaozue Zazhi* 43(5):401-6, 1991), thymidine nitrosourea analogues (Zhang et al., *Cancer Commun.* 3(4):119-26, 1991), 1,3-bis(2-chloroethyl)-1-nitrosourea (August et al., *Cancer Res.* 51(6):1586-90, 1991), 2,2,6,6-tetramethyl-1-oxopiperidiunium nitrosourea derivatives (U.S.S.R. 1261253), 2- and 4-deoxy sugar nitrosourea derivatives (U.S. Pat. No. 4,902,791), nitroxyl nitrosourea derivatives (U.S.S.R. 1336489), fotemustine (Boutin et al., *Eur. J. Cancer Clin. Oncol.* 25(9):1311-16, 1989), pyrimidine (II) nitrosourea derivatives (Wei et al., *Chung-hua Yao Hsueh Tsa Chih* 41(1):19-26, 1989), CGP 6809 (Schieweck et al., *Cancer Chemother. Pharmacol.* 23(6):341-7, 1989), B-3839 (Prajda et al., *In Vivo* 2(2):151-4, 1988), 5-halogenocytosine nitrosourea derivatives (Chiang & Tseng, *T'ai-wan Yao Hsueh Tsa Chih* 38(1):37-43, 1986), 1-(2-chloroethyl)-3-isobutyl-3-(β-maltosyl)-1-nitrosourea (Fujimoto & Ogawa, *J. Pharmacobio-Dyn.* 10(7):341-5, 1987), sulfur-containing nitrosoureas (Tang et al., Yaoxue *Xuebao* 21(7):502-9, 1986), sucrose, 6-((((2-chloroethyl)nitrosoamino-)carbonyl) amino)-6-deoxysucrose (NS-1C) and 6'-((((2-chloroethyl)nitrosoamino)carbonyl)amino)-6'-deoxysucrose (NS-1D) nitrosourea derivatives (Tanoh et al., *Chemotherapy* (Tokyo) 33(11):969-77, 1985), CNCC, RFCNU and chlorozotocin (Mena et al., *Chemotherapy* (*Basel*) 32(2):131-7, 1986), CNUA (Edanami et al., *Chemotherapy* (*Tokyo*) 33(5):455-61, 1985), 1-(2-chloroethyl)-3-isobutyl-3-(β-maltosyl)-1-nitrosourea (Fujimoto & Ogawa, *Jpn. J. Cancer Res.* (*Gann*) 76(7):651-6, 1985), choline-like nitrosoalkylureas (Belyaev et al., *Izv. Akad. NAUK SSSR, Ser. Khim.* 3:553-7, 1985), sucrose nitrosourea derivatives (JP 84219300), sulfa drug nitrosourea analogues (Chiang et al., *Proc. Nat'l Sci. Counc., Repub. China, Part A* 8(1):18-22, 1984), DONU (Asanuma et al., *J. Jpn. Soc. Cancer Ther.* 17(8):2035-43, 1982), N,N'-bis (N-(2-chloroethyl)-N-nitrosocarbamoyl)cystamine (CNCC) (Blazsek et al., *Toxicol. Appl. Pharmacol.* 74(2):250-7, 1984), dimethylnitrosourea (Krutova et al., *Izv. Akad. NAUK SSSR, Ser. Biol.* 3:439-45, 1984), GANU (Sava & Giraldi, *Cancer Chemother. Pharmacol.* 10(3):167-9, 1983), CCNU (Capelli et al., *Med., Biol., Environ.* 11(1):111-16, 1983), 5-aminomethyl-2'-deoxyuridine nitrosourea analogues (Shiau, *Shih Ta Hsueh Pao* (Taipei) 27:681-9, 1982), TA-077 (Fujimoto & Ogawa, Cancer Chemother. Pharmacol. 9(3):134-9, 1982), gentianose nitrosourea derivatives (JP 82 80396), CNCC, RFCNU, RPCNU AND chlorozotocin (CZT) (Marzin et al., INSERM Symp., 19(Nitrosoureas Cancer Treat.):165-74, 1981), thiocolchicine nitrosourea analogues (George, *Shih Ta Hsueh Pao* (Taipei) 25:355-62, 1980), 2-chloroethyl-nitrosourea (Zeller & Eisenbrand, *Oncology* 38(1):39-42, 1981), ACNU, (1-(4-amino-2-methyl-5-pyrimidinyl)methyl-3-(2-chloroethyl)-3-nitrosourea hydrochloride) (Shibuya et al., *Gan To Kagaku Ryoho* 7(8):1393-401, 1980), N-deacetylmethyl thiocolchicine nitrosourea analogues (Lin et al., *J. Med. Chem.* 23(12):1440-2, 1980), pyridine and piperidine nitrosourea derivatives (Crider et al., *J. Med. Chem.* 23(8):848-51, 1980), methyl-CCNU (Zimber & Perk, *Refu. Vet.* 35(1):28, 1978), phensuzimide nitrosourea derivatives (Crider et al., *J. Med. Chem.* 23(3):324-6, 1980), ergoline nitrosourea derivatives (Crider et al., *J. Med. Chem.* 22(1):32-5, 1979), glucopyranose nitrosourea derivatives (JP 78 95917), 1-(2-chloroethyl)-3-cyclohexyl-1-nitrosourea (Farmer et al., *J. Med. Chem.* 21(6): 514-20, 1978), 4-(3-(2-chloroethyl)-3-nitrosoureid-o)-cis-cyclohexanecarboxylic acid (Drewinko et al., *Cancer Treat. Rep.* 61(8):J1513-18, 1977), RPCNU (ICIG 1163) (Larnicol et al., *Biomedicine* 26(3):J176-81, 1977), IOB-252 (Sorodoc et al., *Rev. Roum. Med. Virol.* 28(1):J55-61, 1977), 1,3-bis(2-chloroethyl)-1-nitrosourea (BCNU) (Siebert & Eisenbrand, *Mutat. Res.* 42(1):J45-50, 1977), 1-tetrahydroxycyclopentyl-3-nitroso-3-(2-chloroethyl)-urea (U.S. Pat. No. 4,039,578), d-1-1-(β-chloroethyl)-3-(2-oxo-3-hexahydroazepinyl)-1-nitrosourea (U.S. Pat. No. 3,859,277) and gentianose nitrosourea derivatives (JP 57080396); 6-S-aminoacyloxymethyl mercaptopurine derivatives (Harada et al., *Chem. Pharm. Bull.* 43(10):793-6, 1995), 6-mercaptopurine (6-MP) (Kashida et al., *Biol. Pharm. Bull.* 18(11):1492-7, 1995), 7,8-polymethyleneimidazo-1,3,2-diazaphosphorines (Nilov et al., *Mendeleev Commun.* 2:67, 1995), azathioprine (Chifotides et al., *J. Inorg. Biochem.* 56(4):249-64, 1994), methyl-D-glucopyranoside mercaptopurine derivatives (Da Silva et al., *Eur. J. Med. Chem.* 29(2):149-52, 1994) and s-alkynyl mercaptopurine derivatives (Ratsino et al., *Khim.-Farm. Zh.* 15(8):65-7, 1981); indoline ring and a modified ornithine or glutamic acid-bearing methotrexate derivatives (Matsuoka et al., *Chem. Pharm. Bull.* 45(7):1146-1150, 1997), alkyl-substituted benzene ring C bearing methotrexate derivatives (Matsuoka et al., *Chem. Pharm. Bull.* 44(12):2287-2293, 1996), benzoxazine or benzothiazine moiety-bearing methotrexate derivatives (Matsuoka et al., *J. Med. Chem.* 40(1): 105-111, 1997), 10-deazaminopterin analogues (DeGraw et al., *J. Med. Chem.* 40(3):370-376, 1997), 5-deazaminopterin and 5,10-dideazaminopterin methotrexate analogues (Piper et al., *J. Med. Chem.* 40(3):377-384, 1997), indoline moiety-bearing methotrexate derivatives (Matsuoka et al., *Chem. Pharm. Bull.* 44(7):1332-1337, 1996), lipophilic amide methotrexate derivatives (Pignatello et al., World Meet. Pharm., Biopharm. Pharm. Technol., 563-4, 1995), L-threo-(2S,4S)-4-fluoroglutamic acid and DL-3,3-difluoroglutamic acid-containing methotrexate analogues (Hart et al., *J. Med. Chem.* 39(1):56-65, 1996), methotrexate tetrahydroquinazoline analogue (Gangjee, et al., *J. Heterocycl. Chem.* 32(1): 243-8, 1995), N-(α-aminoacyl)methotrexate derivatives (Cheung et al., *Pteridines* 3(1-2):101-2, 1992), biotin methotrexate derivatives (Fan et al., *Pteridines* 3(1-2):131-2, 1992), D-glutamic acid or D-erythrou, threo-4-fluoroglutamic acid methotrexate analogues (McGuire et al., *Biochem. Pharmacol.* 42(12):2400-3, 1991), β,γ-methano methotrexate analogues (Rosowsky et al., *Pteridines* 2(3):133-9, 1991), 10-deazaminopterin (10-EDAM) analogue (Braakhuis et al., *Chem. Biol. Pteridines, Proc. Int. Symp. Pteridines Folic Acid Deriv,* 1027-30, 1989), γ-tetrazole methotrexate analogue (Kalman et al., *Chem. Biol. Pteridines, Proc. Int. Symp. Pteridines Folic Acid Deriv,* 1154-7, 1989), N-(L-α-aminoacyl)methotrexate derivatives (Cheung et al., *Heterocycles* 28(2):751-8, 1989), meta and ortho isomers of aminopterin (Rosowsky et al., *J. Med. Chem.* 32(12):2582, 1989), hydroxymethylmethotrexate (DE 267495), γ-fluoromethotrexate (McGuire et al., *Cancer Res.* 49(16):4517-25, 1989), polyglutamyl methotrexate derivatives (Kumar et al., *Cancer Res.* 46(10):5020-3, 1986), gem-diphosphonate methotrexate analogues (WO 88/06158), α- and γ-substituted methotrexate analogues (Tsushima et al., *Tetrahedron* 44(17):5375-87, 1988), 5-methyl-5-deaza methotrexate analogues (U.S. Pat. No. 4,725,687), Nδ-acyl-Nα-(4-amino-4-deoxypteroyl)-L-ornithine derivatives (Rosowsky et al., *J. Med. Chem.* 31(7):1332-7, 1988), 8-deaza methotrexate analogues (Kuehl et al., *Cancer Res.* 48(6):1481-8, 1988), acivicin methotrexate analogue (Rosowsky et al., *J. Med. Chem.* 30(8):1463-9, 1987), polymeric platinol methotrexate derivative (Carraher et al., *Polym. Sci. Technol.* (Plenum), 35(*Adv. Biomed. Polym.*):311-24, 1987), methotrexate-γ-dimyristoylphophatidylethanolamine (Kinsky et al., *Biochim. Biophys. Acta* 917(2):211-18, 1987), methotrexate polyglutamate analogues (Rosowsky et al., Chem. Biol. Pteridines, Pteridines Folid Acid Deriv., Proc. Int. Symp. Pteridines Folid Acid Deriv.: Chem., Biol. Clin. Aspects: 985-8, 1986), poly-γ-glutamyl methotrexate derivatives (Kisliuk et al., Chem. Biol. Pteridines, Pteridines Folid Acid Deriv., Proc. Int. Symp. Pteridines Folid Acid Deriv.: Chem., Biol. Clin. Aspects: 989-92, 1986), deoxyuridylate methotrexate derivatives (Webber et al., Chem. Biol. Pteridines, Pteridines Folid Acid Deriv., Proc. Int. Symp. Pteridines Folid Acid Deriv.: Chem., Biol. Clin. Aspects: 659-62, 1986), iodoacetyl lysine methotrexate analogue (Delcamp et al., Chem. Biol. Pteridines, Pteridines Folid Acid Deriv., Proc. Int. Symp. Pteridines Folid Acid Deriv.: Chem., Biol. Clin. Aspects: 807-9, 1986), 2, .omega.-diaminoalkanoid acid-containing methotrexate analogues (McGuire et al., *Biochem. Pharmacol.* 35(15):2607-13, 1986), polyglutamate methotrexate derivatives (Kamen & Winick, *Methods Enzymol.* 122 (Vitam. Coenzymes, Pt. G):339-46, 1986), 5-methyl-5-deaza analogues (Piper et al., *J. Med. Chem.* 29(6):1080-7, 1986), quinazoline methotrexate analogue (Mastropaolo et al., *J. Med. Chem.* 29(1):155-8, 1986), pyrazine methotrexate analogue (Lever & Vestal, *J. Heterocycl. Chem.* 22(1):5-6, 1985), cysteic acid and homocysteic acid methotrexate analogues (U.S. Pat. No. 4,490,529), γ-tert-butyl methotrexate esters (Rosowsky et al., *J. Med. Chem.* 28(5):660-7, 1985), fluorinated methotrexate analogues (Tsushima et al., *Heterocycles* 23(1):45-9, 1985), folate methotrexate analogue (Trombe, *J. Bacteriol.* 160(3):849-53, 1984), phosphonoglutamic acid analogues (Sturtz & Guillamot, *Eur. J. Med. Chem.-Chim. Ther.* 19(3):267-73, 1984), poly(L-lysine)methotrexate conjugates (Rosowsky et al., *J. Med. Chem.* 27(7):888-93, 1984), dilysine and trilysine methotrexate derivates (Forsch & Rosowsky, *J. Org. Chem.* 49(7):1305-9, 1984), 7-hydroxymethotrexate (Fabre et al., *Cancer Res.* 43(10):4648-52, 1983), poly-γ-glutamyl methotrexate analogues (Piper & Montgomery, *Adv. Exp. Med. Biol.,* 163(Folyl Antifolyl Polyglutamates):95-100, 1983), 3',5'-dichloromethotrexate (Rosowsky & Yu, *J. Med. Chem.* 26(10):1448-52, 1983), diazoketone and chloromethylketone methotrexate analogues (Gangjee et al., *J. Pharm. Sci.* 71(6):717-19, 1982), 10-propargylaminopterin and alkyl methotrexate homologs (Piper et al., *J. Med. Chem.* 25(7):877-80, 1982), lectin derivatives of methotrexate (Lin et al., *JNCI* 66(3):523-8, 1981), polyglutamate methotrexate derivatives (Galivan, *Mol. Pharmacol.* 17(1):105-10, 1980), halogentated methotrexate derivatives (Fox, *JNCI* 58(4):J955-8, 1977), 8-alkyl-7, 8-dihydro analogues (Chaykovsky et al., *J. Med. Chem.* 20(10):J1323-7, 1977), 7-methyl methotrexate derivatives and dichloromethotrexate (Rosowsky & Chen, *J. Med. Chem.* 17(12):J1308-11, 1974), lipophilic methotrexate derivatives and 3',5'-dichloromethotrexate (Rosowsky, *J. Med. Chem.* 16(10):J1190-3, 1973), deaza amethopterin analogues (Montgomery et al., *Ann. N.Y. Acad. Sci.* 186:J227-34, 1971), MX068 (*Pharma Japan,* 1658:18, 1999) and cysteic acid and homocysteic acid methotrexate analogues (EPA 0142220); N3-alkylated analogues of 5-fluorouracil (Kozai et al., *J. Chem. Soc., Perkin Trans.* 1(19):3145-3146, 1998), 5-fluorouracil derivatives with 1,4-oxaheteroepane moieties (Gomez et al., *Tetrahedron* 54(43):13295-13312, 1998), 5-fluorouracil and nucleoside analogues (Li, *Anticancer Res.* 17(1A):21-27, 1997), cis- and trans-5-fluoro-5,6-dihydro-6-alkoxyuracil (Van der Wilt et al., *Br. J. Cancer* 68(4):702-7, 1993), cyclopentane 5-fluorouracil analogues (Hronowski & Szarek, *Can. J. Chem.* 70(4):1162-9, 1992), A-OT-fluorouracil (Zhang et al., *Zongguo Yiyao Gongye Zazhi* 20(11):513-15, 1989), N4-trimethoxybenzoyl-5'-deoxy-5-fluorocytidine and 5'-deoxy-5-fluorouridine (Miwa et al., *Chem. Pharm. Bull.* 38(4):998-1003, 1990), 1-hexylcarbamoyl-5-fluorouracil (Hoshi et al., *J. Pharmacobio-Dun.* 3(9):478-81, 1980; Maehara et al., *Chemotherapy (Basel)* 34(6):484-9, 1988), B-3839 (Prajda et al., *In Vivo* 2(2):151-4, 1988), uracil-1-(2-tetrahydrofuryl)-5-fluorouracil (Anai et al., *Oncology* 45(3): 144-7, 1988), 1-(2'-deoxy-2'-fluoro-β-D-arabinofuranosyl)-5-fluorouracil (Suzuko et al., *Mol. Pharmacol.* 31(3):301-6, 1987), doxifluridine (Matuura et al., *Oyo Yakuri* 29(5):803-31, 1985), 5'-deoxy-5-fluorouridine (Bollag & Hartmann, *Eur. J. Cancer* 16(4):427-32, 1980), 1-acetyl-3-β-toluoyl-5-fluorouracil (Okada, *Hiroshima J. Med. Sci.* 28(1):49-66, 1979), 5-fluorouracil-m-formylbenzene-sulfonate (JP 55059173), N'-(2-furanidyl)-5-fluorouracil (JP 53149985) and 1-(2-tetrahydrofuryl)-5-fluorouracil (JP 52089680); 4'-epidoxorubicin (Lanius, Adv. Chemother. Gastrointest. Cancer, (Int. Symp.), 159-67, 1984); N-substituted deacetylvinblastine amide (vindesine) sulfates (Conrad et al., *J. Med. Chem.* 22(4):391-400, 1979); and Cu(II)-VP-16 (etoposide) complex (Tawa et al., *Bioorg. Med. Chem.* 6(7):1003-1008, 1998), pyrrolecarboxamidino-bearing etoposide analogues (Ji et al., *Bioorg. Med. Chem. Lett.* 7(5):607-612, 1997), 4J3-amino etoposide analogues (Hu, University of North Carolina Dissertation, 1992), γ-lactone ring-modified arylamino etoposide analogues (Zhou et al., *J. Med. Chem.* 37(2):287-92, 1994), N-glucosyl etoposide analogue (Allevi et al., *Tetrahedron Lett.* 34(45):7313-16, 1993), etoposide A-ring analogues (Kadow et al., *Bioorg. Med. Chem. Lett.* 2(1):17-22, 1992), 4'-deshydroxy-4'-methyl etoposide (Saulnier et al., *Bioorg. Med. Chem. Lett.* 2(10):1213-18, 1992), pendulum ring etoposide analogues (Sinha et al., *Eur. J. Cancer* 26(5):590-3, 1990) and E-ring desoxy etoposide analogues (Saulnier et al., *J. Med. Chem.* 32(7):1418-20, 1989).

Within one preferred embodiment of the invention, the cell cycle inhibitor is paclitaxel, a compound which disrupts mitosis (M-phase) by binding to tubulin to form abnormal mitotic spindles or an analogue or derivative thereof. Briefly, paclitaxel is a highly derivatized diterpenoid (Wani et al., *J. Am. Chem. Soc.* 93:2325, 1971) which has been obtained from the harvested and dried bark of *Taxus brevifolia* (Pacific Yew) and *Taxomyces Andreanae* and *Endophytic Fungus* of the Pacific Yew (Stierle et al., *Science* 60:214-216, 1993). "Paclitaxel" (which should be understood herein to include formulations, prodrugs, analogues and derivatives such as, for example, TAXOL® (Bristol-Myers Squibb Company, New York, N.Y.), TAXOTERE® (Aventis Pharmaceuticals, France), docetaxel, 10-desacetyl analogues of paclitaxel and 3'N-desbenzoyl-3'N-t-butoxy carbonyl analogues of paclitaxel) may be readily prepared utilizing techniques known to those skilled in the art (see, e.g., Schiff et al., *Nature* 277:665-667, 1979; Long and Fairchild, *Cancer Research* 54:4355-4361, 1994; Ringel and Horwitz, *J. Nat'l Cancer Inst.* 83(4):288-291, 1991; Pazdur et al., *Cancer Treat. Rev.* 19(4):351-386, 1993; WO 94/07882; WO 94/07881; WO 94/07880; WO 94/07876; WO 93/23555; WO 93/10076; WO 94/00156; WO 93/24476; EP 590267; WO 94/20089; U.S. Pat. Nos. 5,294, 637; 5,283,253; 5,279,949; 5,274,137; 5,202,448; 5,200,534; 5,229,529; 5,254,580; 5,412,092; 5,395,850; 5,380,751; 5,350,866; 4,857,653; 5,272,171; 5,411,984; 5,248,796; 5,248,796; 5,422,364; 5,300,638; 5,294,637; 5,362,831; 5,440,056; 4,814,470; 5,278,324; 5,352,805; 5,411,984; 5,059,699; 4,942,184; *Tetrahedron Letters* 35(52):9709-9712, 1994; *J. Med. Chem.* 35:4230-4237, 1992; *J. Med. Chem.* 34:992-998, 1991; *J. Natural Prod.* 57(10):1404-1410, 1994; *J. Natural Prod.* 57(11):1580-1583, 1994; *J. Am. Chem. Soc.* 110:6558-6560, 1988), or obtained from a variety of commercial sources, including for example, Sigma Chemical Co., St. Louis, Mo. (T7402—from *Taxus brevifolia*).

Representative examples of paclitaxel derivatives or analogues include 7-deoxy-docetaxol, 7,8-cyclopropataxanes, N-substituted 2-azetidones, 6,7-epoxy paclitaxels, 6,7-modified paclitaxels, 10-desacetoxytaxol, 10-deacetyltaxol (from 10-deacetylbaccatin III), phosphonooxy and carbonate derivatives of taxol, taxol 2',7-di(sodium 1,2-benzenedicarboxylate, 10-desacetoxy-11,12-dihydrotaxol-10,12(18)-diene derivatives, 10-desacetoxytaxol, Protaxol (2'- and/or 7-O-ester derivatives), (2'- and/or 7-O-carbonate derivatives), asymmetric synthesis of taxol side chain, fluoro taxols, 9-deoxotaxane, (13-acetyl-9-deoxobaccatine III, 9-deoxotaxol, 7-deoxy-9-deoxotaxol, 10-desacetoxy-7-deoxy-9-deoxotaxol, Derivatives containing hydrogen or acetyl group and a hydroxy and tert-butoxycarbonylamino, sulfonated 2'-acryloyltaxol and sulfonated 2'-O-acyl acid taxol derivatives, succinyltaxol, 2'-γ-aminobutyryltaxol formate, 2'-acetyl taxol, 7-acetyl taxol, 7-glycine carbamate taxol, 2'-OH-7-PEG(5000) carbamate taxol, 2'-benzoyl and 2',7-dibenzoyl taxol derivatives, other prodrugs (2'-acetyltaxol; 2',7-diacetyltaxol; 2' succinyltaxol; 2'-(beta-alanyl)-taxol); 2' gamma-aminobutyryltaxol formate; ethylene glycol derivatives of 2'-succinyltaxol; 2'-glutaryltaxol; 2'-(N,N-dimethylglycyl)taxol; 2'-(2-(N,N-dimethylamino)propionyl)taxol; 2' orthocarboxybenzoyl taxol; 2' aliphatic carboxylic acid derivatives of taxol, Prodrugs {2'(N,N-diethylaminopropionyl)taxol, 2'(N,N-dimethylglycyl)taxol, 7(N,N-dimethylglycyl)taxol, 2',7-di-(N,N-dimethylglycyl)taxol, 7(N,N-diethylaminopropionyl)taxol, 2',7-di(N,N-diethylaminopropionyl) taxol, 2'-(L-glycyl)taxol, 7-(L-glycyl)taxol, 2',7-di(L-glycyl) taxol, 2'-(L-alanyl)taxol, 7-(L-alanyl)taxol, 2',7-di(L-alanyl) taxol, 2'-(L-leucyl)taxol, 7-(L-leucyl)taxol, 2',7-di(L-leucyl) taxol, 2'-(L-isoleucyl)taxol, 7-(L-isoleucyl)taxol, 2',7-di(L-isoleucyl)taxol, 2'-(L-valyl)taxol, 7-(L-valyl)taxol, 2'7-di(L-valyl)taxol, 2'-(L-phenylalanyl)taxol, 7-(L-phenylalanyl) taxol, 2',7-di(L-phenylalanyl)taxol, 2'-(L-prolyl)taxol, 7-(L-prolyl)taxol, 2',7-di(L-prolyl)taxol, 2'-(L-lysyl)taxol, 7-(L-lysyl)taxol, 2',7-di(L-lysyl)taxol, 2'-(L-glutamyl)taxol, 7-(L-glutamyl)taxol, 2',7-di(L-glutamyl)taxol, 2'-(L-arginyl) taxol, 7-(L-arginyl)taxol, 2',7-di(L-arginyl)taxol}, Taxol analogues with modified phenylisoserine side chains, taxotere, (N-debenzoyl-N-tert-(butoxycaronyl)-10-deacetyltaxol, and taxanes (e.g., baccatin III, cephalomannine, 10-deacetylbaccatin III, brevifoliol, yunantaxusin and taxusin); and other taxane analogues and derivatives, including 14-beta-hydroxy-10 deacetybaccatin III, debenzoyl-2-acyl paclitaxel derivatives, benzoate paclitaxel derivatives, phosphonooxy and carbonate paclitaxel derivatives, sulfonated 2'-acryloyltaxol; sulfonated 2'-O-acyl acid paclitaxel derivatives, 18-site-substituted paclitaxel derivatives, chlorinated paclitaxel analogues, C4 methoxy ether paclitaxel derivatives, sulfenamide taxane derivatives, brominated paclitaxel analogues, Girard taxane derivatives, nitrophenyl paclitaxel, 10-deacetylated substituted paclitaxel derivatives, 14-beta-hydroxy-10 deacetylbaccatin III taxane derivatives, 07 taxane derivatives, 010 taxane derivatives, 2-debenzoyl-2-acyl taxane derivatives, 2-debenzoyl and -2-acyl paclitaxel derivatives, taxane and baccatin III analogues bearing new C2 and C4 functional groups, n-acyl paclitaxel analogues, 10-deacetylbaccatin III and 7-protected-10-deacetylbaccatin III derivatives from 10-deacetyl taxol A, 10-deacetyl taxol B, and 10-deacetyl taxol, benzoate derivatives of taxol, 2-aroyl-4-acyl paclitaxel analogues, orthro-ester paclitaxel analogues, 2-aroyl-4-acyl paclitaxel analogues and 1-deoxy paclitaxel and 1-deoxy paclitaxel analogues.

In one aspect, the Cell Cycle Inhibitor is a taxane having the formula (C1):

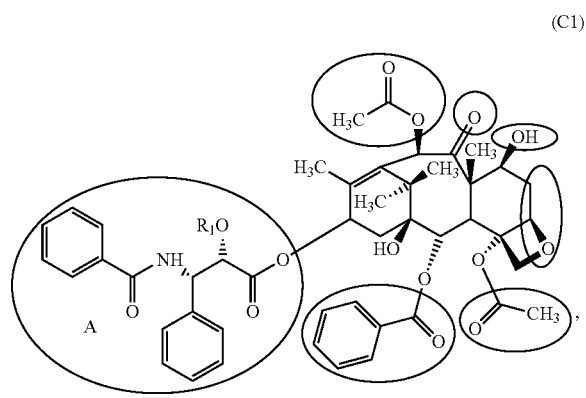

(C1)

where the gray-highlighted portions may be substituted and the non-highlighted portion is the taxane core. A side-chain (labeled "A" in the diagram) is desirably present in order for the compound to have good activity as a Cell Cycle Inhibitor. Examples of compounds having this structure include paclitaxel (Merck Index entry 7117), docetaxol (TAXOTERE, Merck Index entry 3458), and 3'-desphenyl-3'-(4-nitrophenyl)-N-debenzoyl-N-(t-butoxycarbonyl)-10-deacetyltaxol.

In one aspect, suitable taxanes such as paclitaxel and its analogues and derivatives are disclosed in U.S. Pat. No. 5,440,056 as having the structure (C2):

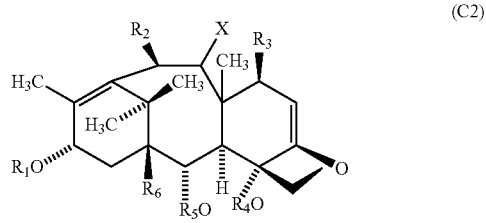

(C2)

wherein X may be oxygen (paclitaxel), hydrogen (9-deoxy derivatives), thioacyl, or dihydroxylprecursors; $R_1$ is selected from paclitaxel or taxotere side chains or alkanoyl of the formula (C3)

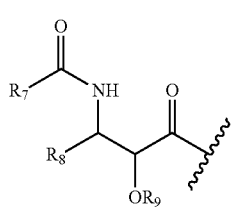

(C3)

wherein $R_7$ is selected from hydrogen, alkyl, phenyl, alkoxy, amino, phenoxy (substituted or unsubstituted); $R_8$ is selected from hydrogen, alkyl, hydroxyalkyl, alkoxyalkyl, aminoalkyl, phenyl (substituted or unsubstituted), alpha or beta-naphthyl; and $R_9$ is selected from hydrogen, alkanoyl, substituted alkanoyl, and aminoalkanoyl; where substitutions refer to hydroxyl, sulfhydryl, allalkoxyl, carboxyl, halogen, thioalkoxyl, N,N-dimethylamino, alkylamino, dialkylamino, nitro, and —OSO$_3$H, and/or may refer to groups containing such substitutions; $R_2$ is selected from hydrogen or oxygen-containing groups, such as hydroxyl, alkoyl, alkanoyloxy, aminoalkanoyloxy, and peptidyalkanoyloxy; $R_3$ is selected from hydrogen or oxygen-containing groups, such as hydroxyl, alkoyl, alkanoyloxy, aminoalkanoyloxy, and peptidyalkanoyloxy, and may further be a silyl containing group or a sulphur containing group; $R_4$ is selected from acyl, alkyl, alkanoyl, aminoalkanoyl, peptidylalkanoyl and aroyl; $R_5$ is selected from acyl, alkyl, alkanoyl, aminoalkanoyl, peptidylalkanoyl and aroyl; $R_6$ is selected from hydrogen or oxygen-containing groups, such as hydroxyl alkoyl, alkanoyloxy, aminoalkanoyloxy, and peptidyalkanoyloxy.

In one aspect, the paclitaxel analogues and derivatives useful as Cell Cycle Inhibitors in the present invention are disclosed in PCT International Patent Application No. WO 93/10076. As disclosed in this publication, the analogue or derivative should have a side chain attached to the taxane nucleus at $C_{13}$, as shown in the structure below (formula C4), in order to confer antitumor activity to the taxane.

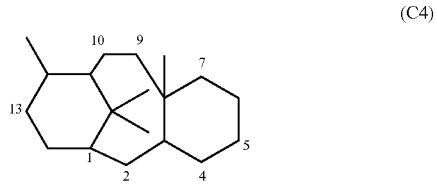

(C4)

WO 93/10076 discloses that the taxane nucleus may be substituted at any position with the exception of the existing methyl groups. The substitutions may include, for example, hydrogen, alkanoyloxy, alkenoyloxy, aryloyloxy. In addition, oxo groups may be attached to carbons labeled 2, 4, 9, 10. As well, an oxetane ring may be attached at carbons 4 and 5. As well, an oxirane ring may be attached to the carbon labeled 4.

In one aspect, the taxane-based Cell Cycle Inhibitor useful in the present invention is disclosed in U.S. Pat. No. 5,440,056, which discloses 9-deoxo taxanes. These are compounds lacking an oxo group at the carbon labeled 9 in the taxane structure shown above (formula C4). The taxane ring may be substituted at the carbons labeled 1, 7 and 10 (independently) with H, OH, O—R, or O—CO—R where R is an alkyl or an aminoalkyl. As well, it may be substituted at carbons labeled 2 and 4 (independently) with aryol, alkanoyl, aminoalkanoyl or alkyl groups. The side chain of formula (C3) may be substituted at $R_7$ and $R_8$ (independently) with phenyl rings, substituted phenyl rings, linear alkanes/alkenes, and groups containing H, O or N. $R_9$ may be substituted with H, or a substituted or unsubstituted alkanoyl group.

Taxanes in general, and paclitaxel is particular, is considered to function as a Cell Cycle Inhibitor by acting as an anti-microtuble agent, and more specifically as a stabilizer. These compounds have been shown useful in the treatment of proliferative disorders, including: non-small cell (NSC) lung; small cell lung; breast; prostate; cervical; endometrial; head and neck cancers.

In another aspect, the Cell Cycle Inhibitor is a Vinca Alkaloid. Vinca alkaloids have the following general structure. They are indole-dihydroindole dimers.

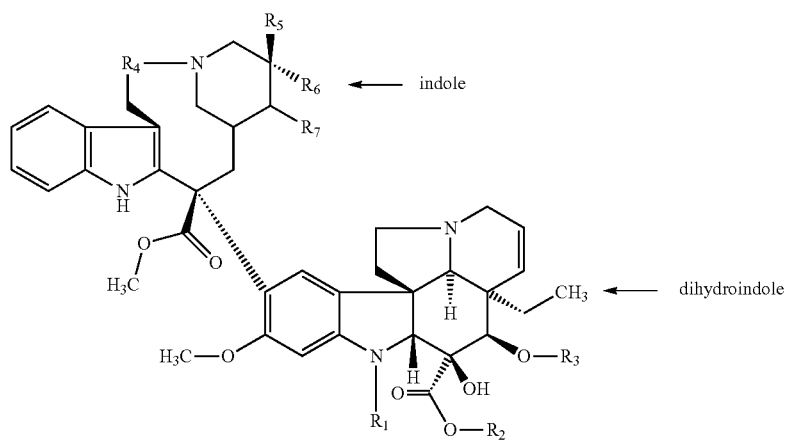

← indole

← dihydroindole

As disclosed in U.S. Pat. Nos. 4,841,045 and 5,030,620, $R_1$ can be a formyl or methyl group or alternately H. $R_1$ could also be an alkyl group or an aldehyde-substituted alkyl (e.g., $CH_2CHO$). $R_2$ is typically a $CH_3$ or $NH_2$ group. However it can be alternately substituted with a lower alkyl ester or the ester linking to the dihydroindole core may be substituted with C(O)—R where R is $NH_2$, an amino acid ester or a peptide ester. $R_3$ is typically $C(O)CH_3$, $CH_3$ or H. Alternately, a protein fragment may be linked by a bifunctional group such as maleoyl amino acid. $R_3$ could also be substituted to form an alkyl ester which may be further substituted. $R_4$ may be —$CH_2$— or a single bond. $R_5$ and $R_6$ may be H, OH or a lower alkyl, typically —$CH_2CH_3$. Alternatively $R_6$ and $R_7$ may together form an oxetane ring. $R_7$ may alternately be H. Further substitutions include molecules wherein methyl groups are substituted with other alkyl groups, and whereby unsaturated rings may be derivatized by the addition of a side group such as an alkane, alkene, alkyne, halogen, ester, amide or amino group.

Exemplary Vinca Alkaloids are vinblastine, vincristine, vincristine sulfate, vindesine, and vinorelbine, having the structures:

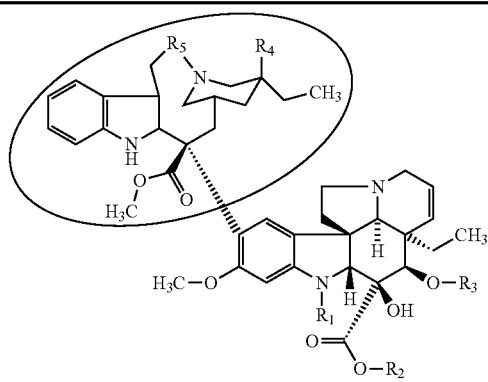

| | $R_1$ | $R_2$ | $R_3$ | $R_4$ | $R_5$ |
|---|---|---|---|---|---|
| Vinblastine: | $CH_3$ | $CH_3$ | $C(O)CH_3$ | OH | $CH_2$ |
| Vincristine: | $CH_2O$ | $CH_3$ | $C(O)CH_3$ | OH | $CH_2$ |
| Vindesine: | $CH_3$ | $NH_2$ | H | OH | $CH_2$ |
| Vinorelbine: | $CH_3$ | $CH_3$ | $CH_3$ | H | single bond |

Analogues typically require the side group (shaded area) in order to have activity. These compounds are thought to act as Cell Cycle Inhibitors by functioning as anti-microtubule agents, and more specifically to inhibit polymerization. These compounds have been shown useful in treating proliferative disorders, including NSC lung; small cell lung; breast; prostate; brain; head and neck; retinoblastoma; bladder; and penile cancers; and soft tissue sarcoma.

In another aspect, the Cell Cycle Inhibitor is Camptothecin, or an analogue or derivative thereof. Camptothecins have the following general structure.

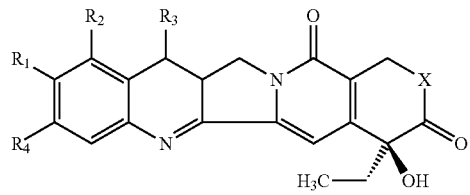

In this structure, X is typically 0, but can be other groups, e.g., NH in the case of 21-lactam derivatives. $R_1$ is typically H or OH, but may be other groups, e.g., a terminally hydroxylated $C_{1-3}$ alkane. $R_2$ is typically H or an amino containing group such as $(CH_3)_2NHCH_2$, but may be other groups e.g., $NO_2$, $NH_2$, halogen (as disclosed in, e.g., U.S. Pat. No. 5,552,156) or a short alkane containing these groups. $R_3$ is typically H or a short alkyl such as $C_2H_5$. $R_4$ is typically H but may be other groups, e.g., a methylenedioxy group with $R_1$ Exemplary camptothecin compounds include topotecan, irinotecan (CPT-11), 9-aminocamptothecin, 21-lactam-20 (S)-camptothecin, 10,11-methylenedioxycamptothecin, SN-38, 9-nitrocamptothecin, 10-hydroxycamptothecin. Exemplary compounds have the structures:

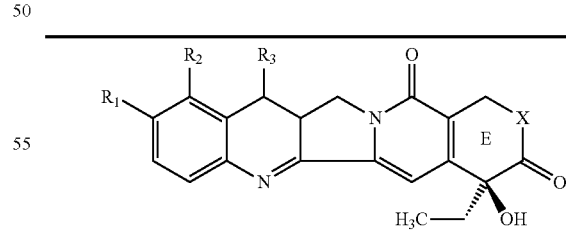

| | $R_1$ | $R_2$ | $R_3$ |
|---|---|---|---|
| Camptothecin: | H | H | H |
| Topotecan: | OH | $(CH_3)_2NHCH_2$ | H |
| SN-38: | OH | H | $C_2H_5$ |

X: O for most analogs, NH for 21-lactam analogs

Camptothecins have the five rings shown here. The ring labeled E must be intact (the lactone rather than carboxylate form) for maximum activity and minimum toxicity. These compounds are useful to as Cell Cycle Inhibitors, where they function as Topoisomerase I Inhibitors and/or DNA cleavage agents. They have been shown useful in the treatment of proliferative disorders, including, for example, NSC lung; small cell lung; and cervical cancers.

In another aspect, the Cell Cycle Inhibitor is a Podophyllotoxin, or a derivative or an analogue thereof. Exemplary compounds of this type are Etoposide or Teniposide, which have the following structures:

| | R |
|---|---|
| Etoposide | $CH_3$ |
| Teniposide | |

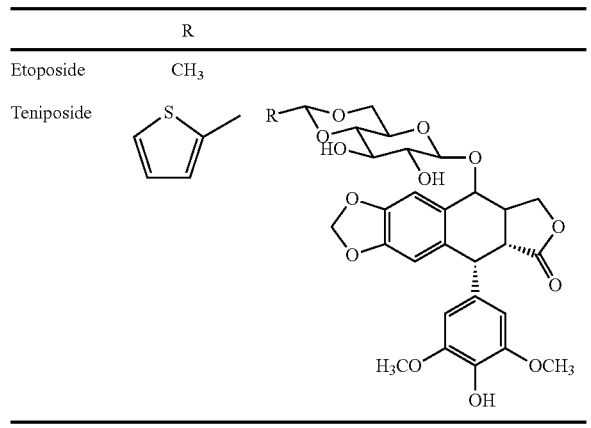

These compounds are thought to function as Cell Cycle Inhibitors by being Topoisomerase II Inhibitors and/or by DNA cleaving agents. They have been shown useful as antiproliferative agents in, e.g., small cell lung, prostate, and brain cancers, and in retinoblastoma.

In another aspect, the Cell Cycle Inhibitor is an Anthracycline. Anthracyclines have the following general structure, where the R groups may be a variety of organic groups:

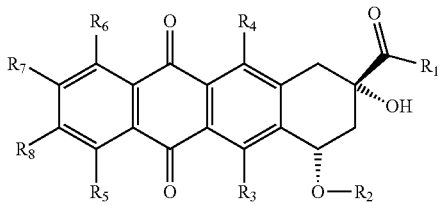

According to U.S. Pat. No. 5,594,158, suitable R groups are: $R_1$ is $CH_3$ or $CH_2OH$; $R_2$ is daunosamine or H; $R_3$ and $R_4$ are independently one of OH, $NO_2$, $NH_2$, F, Cl, Br, I, CN, H or groups derived from these; $R_{5-7}$ are all H or $R_5$ and $R_6$ are H and $R_7$ and $R_8$ are alkyl or halogen, or vice versa: $R_7$ and $R_8$ are H and $R_5$ and $R_6$ are alkyl or halogen.

According to U.S. Pat. No. 5,843,903, $R_2$ may be a conjugated peptide. According to U.S. Pat. Nos. 4,215,062 and 4,296,105, $R_5$ may be OH or an ether linked alkyl group. $R_1$ may also be linked to the anthracycline ring by a group other than C(O), such as an alkyl or branched alkyl group having the C(O) linking moiety at its end, such as $-CH_2CH(CH_2-X)C(O)-R_1$, wherein X is H or an alkyl group (see, e.g., U.S. Pat. No. 4,215,062). $R_2$ may alternately be a group linked by the functional group =N—NHC(O)—Y, where Y is a group such as a phenyl or substituted phenyl ring. Alternately $R_3$ may have the following structure:

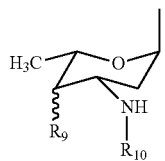

in which $R_9$ is OH either in or out of the plane of the ring, or is a second sugar moiety such as $R_3$. $R_{10}$ may be H or form a secondary amine with a group such as an aromatic group, saturated or partially saturated 5 or 6 membered heterocyclic having at least one ring nitrogen (see U.S. Pat. No. 5,843,903). Alternately, $R_{10}$ may be derived from an amino acid, having the structure $-C(O)CH(NHR_{11})(R_{12})$, in which $R_{11}$ is H, or forms a $C_{3-4}$ membered alkylene with $R_{12}$. $R_{12}$ may be H, alkyl, aminoalkyl, amino, hydroxy, mercapto, phenyl, benzyl or methylthio (see U.S. Pat. No. 4,296,105).

Exemplary Anthracyclines are Doxorubicin, Daunorubicin, Idarubicin, Epirubicin, Pirarubicin, Zorubicin, and Carubicin. Suitable compounds can have the structures:

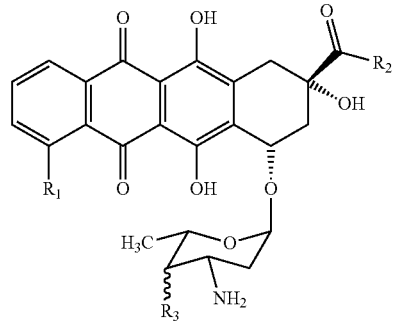

| | $R_1$ | $R_2$ | $R_3$ |
|---|---|---|---|
| Doxorubicin: | $OCH_3$ | $CH_2OH$ | OH out of ring plane |
| Epirubicin: (4' epimer of doxorubicin) | $OCH_3$ | $CH_2OH$ | OH in ring plane |
| Daunorubicin: | $OCH_3$ | $CH_3$ | OH out of ring plane |
| Idarubicin: | H | $CH_3$ | OH out of ring plane |
| Pirarubicin | $OCH_3$ | OH | A |
| Zorubicin | $OCH_3$ | =N—NHC(O)$C_6H_5$ | B |
| Carubicin | OH | $CH_3$ | B |

A: 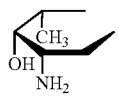 / B:

Other suitable Anthracyclines are Anthramycin, Mitoxantrone, Menogaril, Nogalamycin, Aclacinomycin A, Olivomycin A, Chromomycin $A_3$, and Plicamycin having the structures:

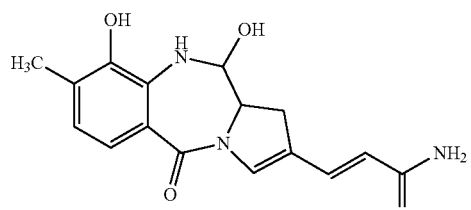

Anthramycin

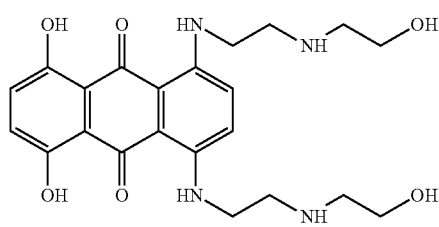

Mitoxantrone

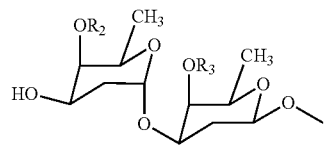

| | $R_1$ | $R_2$ | $R_3$ | $R_4$ |
|---|---|---|---|---|
| Olivomycin A | COCH(CH$_3$)$_2$ | CH$_3$ | COCH$_3$ | H |
| Chromomycin A$_3$ | COCH$_3$ | CH$_3$ | COCH$_3$ | CH$_3$ |
| Plicamycin | H | H | H | CH$_3$ |

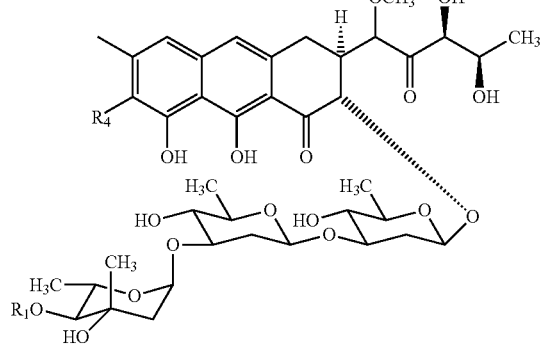

| | $R_1$ | $R_2$ | $R_3$ |
|---|---|---|---|
| Menogaril | H | | OCH$_3$ | H |
| Nogalamycin | O-sugar | | H | COOCH$_3$ |

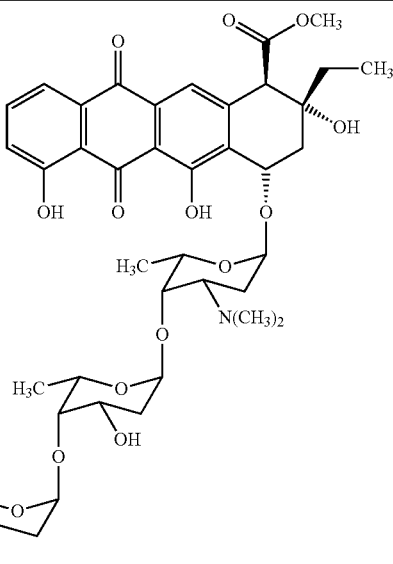

Aclacinomycin A sugar: 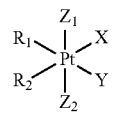

These compounds are thought to function as Cell Cycle Inhibitors by being Topoisomerase Inhibitors and/or by DNA cleaving agents. They have been shown useful in the treatment of proliferative disorders, including small cell lung; breast; endometrial; head and neck; retinoblastoma; liver; bile duct; islet cell; and bladder cancers; and soft tissue sarcoma.

In another aspect, the Cell Cycle Inhibitor is a Platinum compound. In general, suitable platinum complexes may be of Pt(II) or Pt(IV) and have this basic structure:

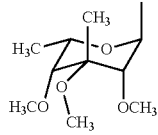

wherein X and Y are anionic leaving groups such as sulfate, phosphate, carboxylate, and halogen; $R_1$ and $R_2$ are alkyl, amine, amino alkyl any may be further substituted, and are basically inert or bridging groups. For Pt(II) complexes $Z_1$ and $Z_2$ are non-existent. For Pt(IV) $Z_1$ and $Z_2$ may be anionic groups such as halogen, hydroxy, carboxylate, ester, sulfate or phosphate. See, e.g., U.S. Pat. Nos. 4,588,831 and 4,250,189.

Suitable platinum complexes may contain multiple Pt atoms. See, e.g., U.S. Pat. Nos. 5,409,915 and 5,380,897. For example bisplatinum and triplatinum complexes of the type:

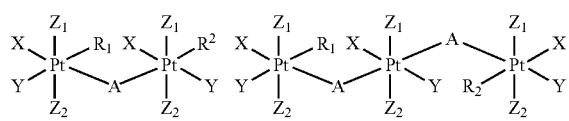

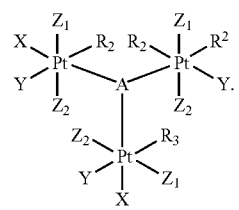

Exemplary Platinum compound are Cisplatin, Carboplatin, Oxaliplatin, and Miboplatin having the structures:

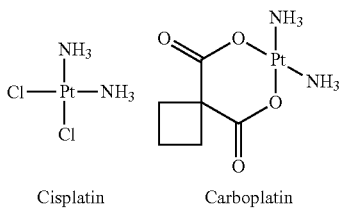

Cisplatin    Carboplatin

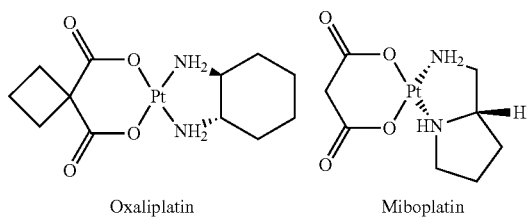

Oxaliplatin    Miboplatin

These compounds are thought to function as Cell Cycle Inhibitors by binding to DNA, i.e., acting as alkylating agents of DNA. These compounds have been shown useful in the treatment of cell proliferative disorders, including, e.g., NSC lung; small cell lung; breast; cervical; brain; head and neck; esophageal; retinoblastom; liver; bile duct; bladder; penile; and vulvar cancers; and soft tissue sarcoma.

In another aspect, the Cell Cycle Inhibitor is a Nitrosourea. Nitrosourease have the following general structure (C5), where typical R groups are shown below.

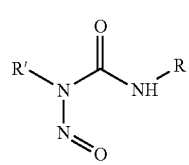

(C5)

R Group:

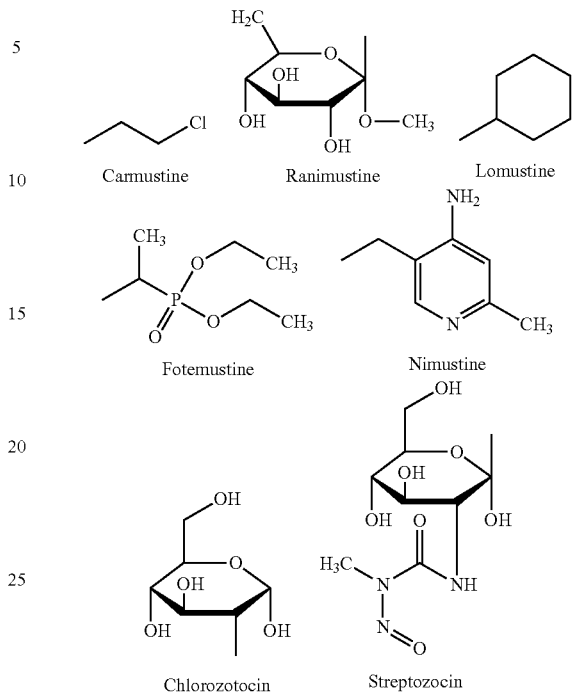

Carmustine    Ranimustine    Lomustine

Fotemustine    Nimustine

Chlorozotocin    Streptozocin

Other suitable R groups include cyclic alkanes, alkanes, halogen substituted groups, sugars, aryl and heteroaryl groups, phosphonyl and sulfonyl groups. As disclosed in U.S. Pat. No. 4,367,239, R may suitably be $CH_2$—$C(X)(Y)(Z)$, wherein X and Y may be the same or different members of the following groups: phenyl, cyclyhexyl, or a phenyl or cyclohexyl group substituted with groups such as halogen, lower alkyl ($C_{1-4}$), trifluore methyl, cyano, phenyl, cyclohexyl, lower alkyloxy ($C_{1-4}$). Z has the following structure: -alkylene-N—$R_1R_2$, where $R_1$ and $R_2$ may be the same or different members of the following group: lower alkyl ($C_{1-4}$) and benzyl, or together $R_1$ and $R_2$ may form a saturated 5 or 6 membered heterocyclic such as pyrrolidine, piperidine, morfoline, thiomorfoline, N-lower alkyl piperazine, where the heterocyclic may be optionally substituted with lower alkyl groups.

As disclosed in U.S. Pat. No. 6,096,923, R and R' of formula (C5) may be the same or different, where each may be a substituted or unsubstituted hydrocarbon having 1-10 carbons. Substitutions may include hydrocarbyl, halo, ester, amide, carboxylic acid, ether, thioether and alcohol groups. As disclosed in U.S. Pat. No. 4,472,379, R of formula (C5) may be an amide bond and a pyranose structure (e.g., Methyl 2'-[N—[N-(2-chloroethyl)-N-nitroso-carbamoyl]-glycyl] amino-2'-deoxy-α-D-glucopyranoside). As disclosed in U.S. Pat. No. 4,150,146, R of formula (C5) may be an alkyl group of 2 to 6 carbons and may be substituted with an ester, sulfonyl, or hydroxyl group. It may also be substituted with a carboxylica acid or $CONH_2$ group.

Exemplary Nitrosoureas are BCNU (Carmustine), Methyl-CCNU (Semustine), CCNU (Lomustine), Ranimustine, Nimustine, Chlorozotocin, Fotemustine, Streptozocin, and Streptozocin, having the structures:

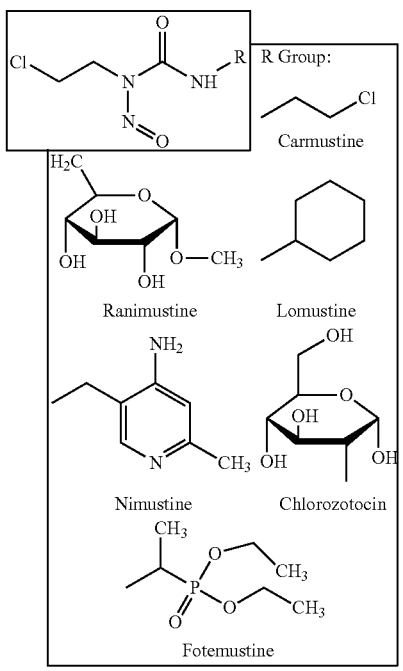

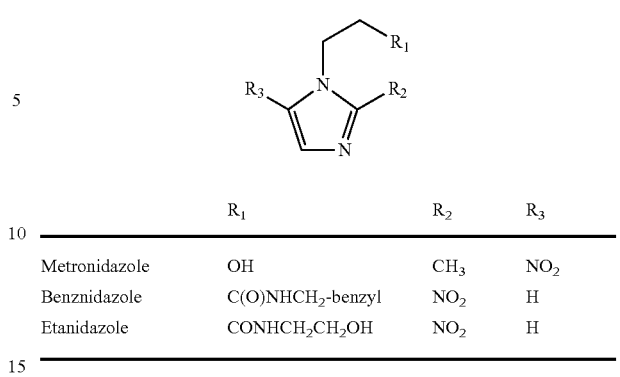

| | $R_1$ | $R_2$ | $R_3$ |
|---|---|---|---|
| Metronidazole | OH | $CH_3$ | $NO_2$ |
| Benznidazole | $C(O)NHCH_2$-benzyl | $NO_2$ | H |
| Etanidazole | $CONHCH_2CH_2OH$ | $NO_2$ | H |

Suitable nitroimidazole compounds are disclosed in, e.g., U.S. Pat. Nos. 4,371,540 and 4,462,992.

In another aspect, the Cell Cycle Inhibitor is a Folic acid antagonist, such as Methotrexate or derivatives or analogues thereof, including Edatrexate, Trimetrexate, Raltitrexed, Piritrexim, Denopterin, Tomudex, and Pteropterin. Methotrexate analogues have the following general structure:

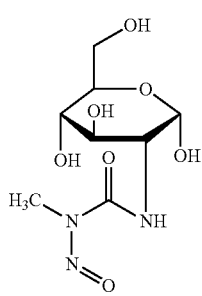

The identity of the R group may be selected from organic groups, particularly those groups set forth in U.S. Pat. Nos. 5,166,149 and 5,382,582. For example, $R_1$ may be N, $R_2$ may be N or $C(CH_3)$, $R_3$ and $R_3'$ may H or alkyl, e.g., $CH_3$, $R_4$ may be a single bond or NR, where R is H or alkyl group. $R_{5,6,8}$ may be H, $OCH_3$, or alternately they can be halogens or hydro groups. $R_7$ is a side chain of the general structure:

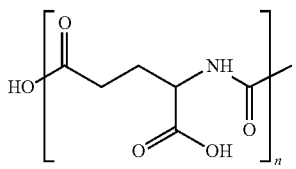

These nitrosourea compounds are thought to function as Cell Cycle Inhibitor by binding to DNA, that is, by functioning as DNA alkylating agents. These Cell Cycle Inhibitors have been shown useful in treating cell proliferative disorders such as, for example, islet cell; small cell lung; melanoma; and brain cancers.

In another aspect, the Cell Cycle Inhibitor is a Nitroimidazole, where exemplary Nitroimidazoles are Metronidazole, Benznidazole, Etanidazole, and Misonidazole, having the structures:

wherein n=1 for methotrexate, n=3 for pteropterin. The carboxyl groups in the side chain may be esterified or form a salt such as a $Zn^{2+}$ salt. $R_9$ and $R_{10}$ can be $NH_2$ or may be alkyl substituted.

Exemplary folic acid antagonist compounds have the structures:

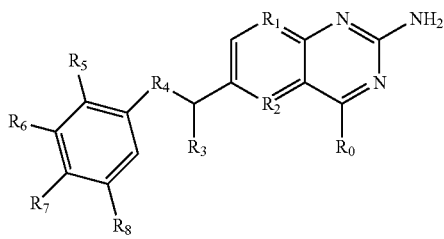

| | $R_0$ | $R_1$ | $R_2$ | $R_3$ | $R_4$ | $R_5$ | $R_6$ | $R_7$ | $R_8$ |
|---|---|---|---|---|---|---|---|---|---|
| Methotrexate | $NH_2$ | N | N | H | $N(CH_3)$ | H | H | A (n = 1) | H |
| Edatrexate | $NH_2$ | N | N | H | $N(CH_2CH_3)$ | H | H | A (n = 1) | H |
| Trimetrexate | $NH_2$ | N | $C(CH_3)$ | H | NH | H | $OCH_3$ | $OCH_3$ | $OCH_3$ |
| Pteropterin | $NH_2$ | N | N | H | $N(CH_3)$ | H | H | A (n = 3) | H |
| Denopterin | OH | N | N | $CH_3$ | $N(CH_3)$ | H | H | A (n = 1) | H |
| Piritrexim | $NH_2$ | N | $C(CH_3)H$ | single bond | $OCH_3$ | H | H | $OCH_3$ | H |

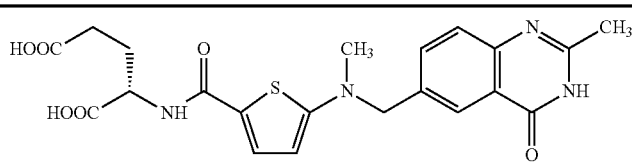

Tomudex

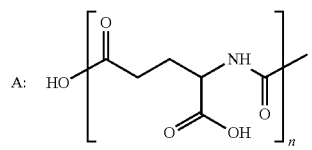

These compounds are thought to function as Cell Cycle Inhibitors by serving as antimetabolites of folic acid. They have been shown useful in the treatment of cell proliferative disorders including, for example, soft tissue sarcoma, small cell lung, breast, brain, head and neck, bladder, and penile cancers.

In another aspect, the Cell Cycle Inhibitor is a Cytidine analogue, such as Cytarabine or derivatives or analogues thereof, including Enocitabine, FMdC ((E(-2'-deoxy-2'-(fluoromethylene)cytidine), Gemcitabine, 5-Azacitidine, Ancitabine, and 6-Azauridine. Exemplary compounds have the structures:

| | $R_1$ | $R_2$ | $R_3$ | $R_4$ |
|---|---|---|---|---|
| Cytarabine | H | OH | H | CH |
| Enocitabine | $C(O)(CH_2)_{20}CH_3$ | OH | H | CH |
| Gemcitabine | H | F | F | CH |
| Azacitidine | H | H | OH | N |
| FMdC | H | $CH_2F$ | H | CH |

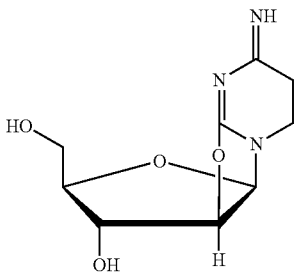

Ancitabine

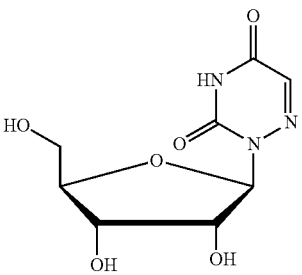

6-Azauridine

These compounds are thought to function as Cell Cycle Inhibitors as acting as antimetabolites of pyrimidine. These compounds have been shown useful in the treatment of cell proliferative disorders including, for example, pancreatic, breast, cervical, NSC lung, and bile duct cancers.

In another aspect, the Cell Cycle Inhibitor is a Pyrimidine analogue. In one aspect, the Pyrimidine analogues have the general structure:

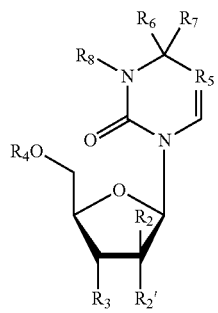

wherein positions 2', 3' and 5' on the sugar ring ($R_2$, $R_3$ and $R_4$, respectively) can be H, hydroxyl, phosphoryl (see, e.g., U.S. Pat. No. 4,086,417) or ester (see, e.g., U.S. Pat. No. 3,894,000). Esters can be of alkyl, cycloalkyl, aryl or heterocyclo/aryl types. The 2' carbon can be hydroxylated at either $R_2$ or $R_2$', the other group is H. Alternately, the 2' carbon can be substituted with halogens e.g., fluoro or difluoro cytidines such as Gemcytabine. Alternately, the sugar can be substituted for another heterocyclic group such as a furyl group or for an alkane, an alkyl ether or an amide linked alkane such as $C(O)NH(CH_2)_5CH_3$. The 2° amine can be substituted with an aliphatic acyl ($R_1$) linked with an amide (see, e.g., U.S. Pat. No. 3,991,045) or urethane (see, e.g., U.S. Pat. No. 3,894,000) bond. It can also be further substituted to form a quaternary ammonium salt. $R_5$ in the pyrimidine ring may be N or CR, where R is H, halogen containing groups, or alkyl (see, e.g., U.S. Pat. No. 4,086,417). $R_6$ and $R_7$ can together can form an oxo group or $R_6$=—NH—$R_1$ and $R_7$=H. $R_8$ is H or $R_7$ and $R_8$ together can form a double bond or $R_8$ can be X, where X is:

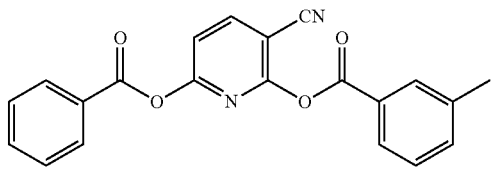 [SMILES: Cc1cccc(C(=O)Oc2nc(OC(=O)c3ccccc3)ccc2C#N)c1]

Specific pyrimidine analogues are disclosed in U.S. Pat. No. 3,894,000 (see, e.g., 2'-O-palmityl-ara-cytidine, 3'-O-benzoyl-ara-cytidine, and more than 10 other examples); U.S. Pat. No. 3,991,045 (see, e.g., N4-acyl-1-β-D-arabinofuranosylcytosine, and numerous acyl groups derivatives as listed therein, such as palmitoyl.

In another aspect, the Cell Cycle Inhibitor is a Fluoropyrimidine Analog, such as 5-Fluorouracil, or an analogue or derivative thereof, including Carmofur, Doxifluridine, Emitefur, Tegafur, and Floxuridine. Exemplary compounds have the structures:

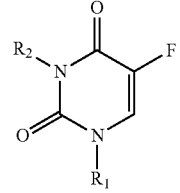

|  | $R_1$ | $R_2$ |
| --- | --- | --- |
| 5-Fluorouracil | H | H |
| Carmofur | $C(O)NH(CH_2)_5CH_3$ | H |
| Doxifluridine | $A_1$ | H |
| Floxuridine | $A_2$ | H |
| Emitefur | $CH_2OCH_2CH_3$ | B |
| Tegafur | C | H |

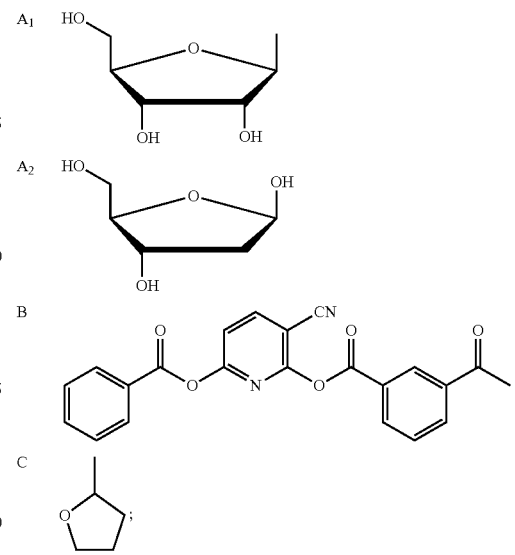

Other suitable Fluoropyrimidine Analogues include 5-FudR (5-fluoro-deoxyuridine), or an analogue or derivative thereof, including 5-iododeoxyuridine (5-IudR), 5-bromodeoxyuridine (5-BudR), Fluorouridine triphosphate (5-FUTP), and Fluorodeoxyuridine monophosphate (5-dFUMP). Exemplary compounds have the structures:

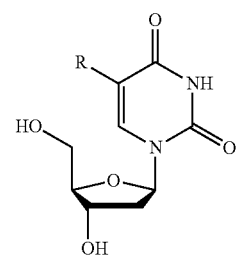

5-Fluoro-2'-deoxyuridine: R = F
5-Bromo-2'-deoxyuridine: R = Br
5-Iodoo-2'-deoxyuridine: R = I These compounds are thought to function as Cell Cycle Inhibitors by serving as antimetabolites of pyrimidine.

In another aspect, the Cell Cycle Inhibitor is a Purine Analogue. Purine analogues have the following general structure:

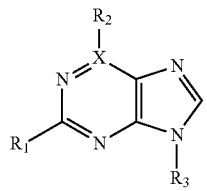

wherein X is typically carbon; $R_1$ is H, halogen, amine or a substituted phenyl; $R_2$ is H, a primary, secondary or tertiary amine, a sulfur containing group, typically —SH, an alkane, a cyclic alkane, a heterocyclic or a sugar; $R_3$ is H, a sugar (typically a furanose or pyranose structure), a substituted sugar or a cyclic or heterocyclic alkane or aryl group. See, e.g., U.S. Pat. No. 5,602,140 for compounds of this type.

In the case of pentostatin, X—R2 is —$CH_2CH(OH)$—. In this case a second carbon atom is inserted in the ring between X and the adjacent nitrogen atom. The X—N double bond becomes a single bond.

U.S. Pat. No. 5,446,139 describes suitable purine analogues of the type shown in the following formula:

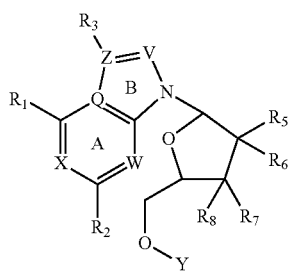

wherein N signifies nitrogen and V, W, X, Z can be either carbon or nitrogen with the following provisos. Ring A may have 0 to 3 nitrogen atoms in its structure. If two nitrogens are present in ring A, one must be in the W position. If only one is present, it must not be in the Q position. V and Q must not be simultaneously nitrogen. Z and Q must not be simultaneously nitrogen. If Z is nitrogen, $R_3$ is not present. Furthermore, $R_{1-3}$ are independently one of H, halogen, $C_{1-7}$ alkyl, $C_{1-7}$ alkenyl, hydroxyl, mercapto, $C_{1-7}$ alkylthio, $C_{1-7}$ alkoxy, $C_{2-7}$ alkenyloxy, aryl oxy, nitro, primary, secondary or tertiary amine containing group. $R_{5-5}$ are H or up to two of the positions may contain independently one of OH, halogen, cyano, azido, substituted amino, $R_5$ and $R_7$ can together form a double bond. Y is H, a $C_{1-7}$ alkylcarbonyl, or a mono- di or tri phosphate.

Exemplary suitable purine analogues include 6-Mercaptopurine, Thiguanosine, Thiamiprine, Cladribine, Fludarabine, Tubercidin, Puromycin, Pentoxyfilline; where these compounds may optionally be phosphorylated. Exemplary compounds have the structures:

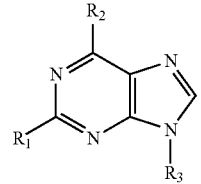

| | $R_1$ | $R_2$ | $R_3$ |
|---|---|---|---|
| 6-Mercaptopurine | H | SH | H |
| Thioguanosine | $NH_2$ | SH | $B_1$ |
| Thiamiprine | $NH_2$ | A | H |
| Cladribine | Cl | $NH_2$ | $B_2$ |
| Fludarabine | F | $NH_2$ | $B_3$ |
| Puromycin | H | $N(CH_3)_2$ | $B_4$ |
| Tubercidin | H | $NH_2$ | $B_1$ |

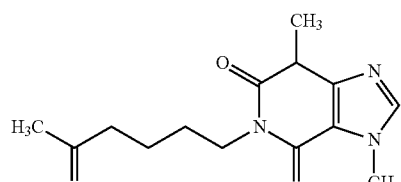

Pentoxyfilline

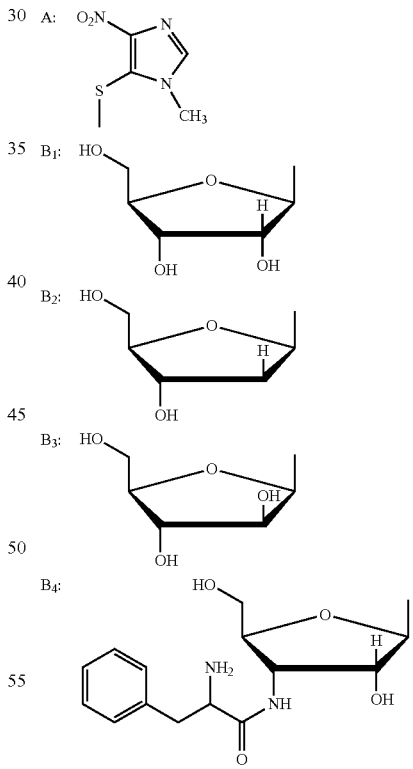

These compounds are thought to function as Cell Cycle Inhibitors by serving as antimetabolites of purine.

In another aspect, the Cell Cycle Inhibitor is a Nitrogen Mustard. Many suitable Nitrogen Mustards are known and are suitably used as a Cell Cycle Inhibitor in the present invention. Suitable Nitrogen Mustards are also known as cyclophosphamides.

A preferred Nitrogen Mustard has the general structure:

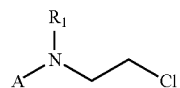

(i)

Where A is:

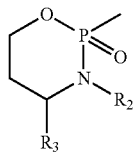

or —CH$_3$ or other alkane, or chloronated alkane, typically CH$_2$CH(CH$_3$)Cl, or a polycyclic group such as B, or a substituted phenyl such as C or a heterocyclic group such as D.

(ii)

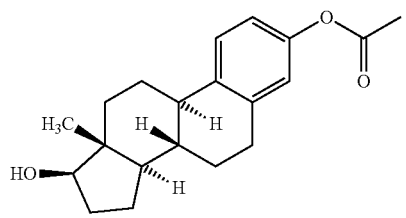

(iii)

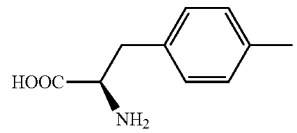

(iv)

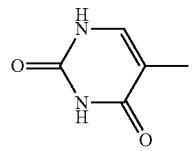

Suitable Nitrogen Mustards are disclosed in U.S. Pat. No. 3,808,297, wherein A is:

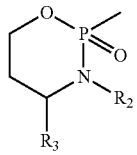

R$_{1-2}$ are H or CH$_2$CH$_2$Cl; R$_3$ is H or oxygen-containing groups such as hydroperoxy; and R$_4$ can be alkyl, aryl, heterocyclic.

The cyclic moiety need not be intact. See, e.g., U.S. Pat. Nos. 5,472,956, 4,908,356, 4,841,085 that describe the following type of structure:

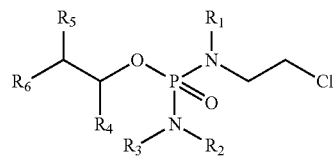

wherein R$_1$ is H or CH$_2$CH$_2$Cl, and R$_{2-6}$ are various substituent groups.

Exemplary Nitrogen Mustards include methylchloroethamine, and analogues or derivatives thereof, including methylchloroethamine oxide hydrohchloride, Novembichin, and Mannomustine (a halogenated sugar). Exemplary compounds have the structures:

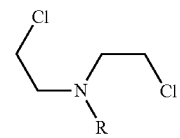

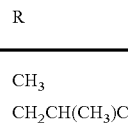

| | R |
|---|---|
| Mechlorethanime | CH$_3$ |
| Novembichin | CH$_2$CH(CH$_3$)Cl |

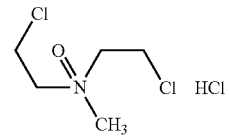

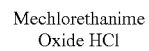

Mechlorethanime Oxide HCl

The Nitrogen Mustard may be Cyclophosphamide, Ifosfamide, Perfosfamide, or Torofosfamide, where these compounds have the structures:

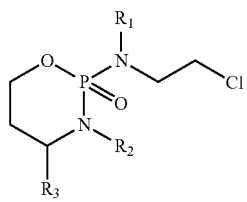

| | R$_1$ | R$_2$ | R$_3$ |
|---|---|---|---|
| Cyclophosphamide | H | CH$_2$CH$_2$Cl | H |
| Ifosfamide | CH$_2$CH$_2$Cl | H | H |
| Perfosfamide | CH$_2$CH$_2$Cl | H | OOH |
| Torofosfamide | CH$_2$CH$_2$Cl | CH$_2$CH$_2$Cl | H |

The Nitrogen Mustard may be Estramustine, or an analogue or derivative thereof, including Phenesterine, Prednimustine, and Estramustine PO$_4$. Thus, suitable Nitrogen Mustard type Cell Cycle Inhibitors of the present invention have the structures:

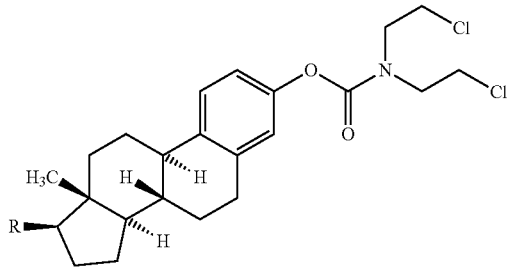

R

| | R |
|---|---|
| Estramustine | OH |
| Phenesterine | C(CH₃)(CH₂)₃CH(CH₃)₂ |

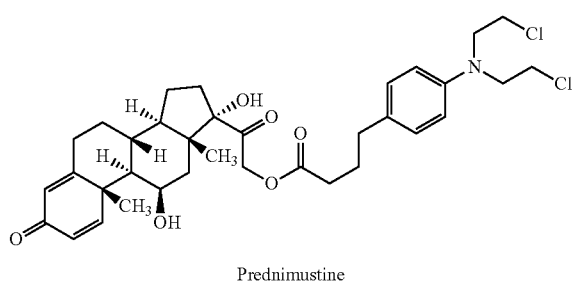

Prednimustine

The Nitrogen Mustard may be Chlorambucil, or an analogue or derivative thereof, including Melphalan and Chlormaphazine. Thus, suitable Nitrogen Mustard type Cell Cycle Inhibitors of the present invention have the structures:

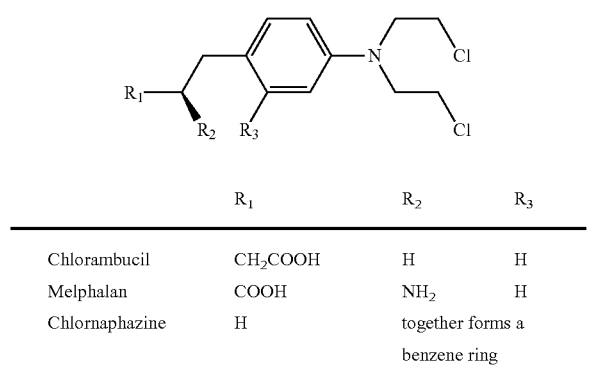

| | $R_1$ | $R_2$ | $R_3$ |
|---|---|---|---|
| Chlorambucil | CH₂COOH | H | H |
| Melphalan | COOH | NH₂ | H |
| Chlornaphazine | H | together forms a benzene ring | |

The Nitrogen Mustard may be uracil mustard, which has the structure:

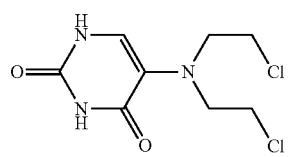 [SMILES: O=c1[nH]cc(N(CCCl)CCCl)c(=O)[nH]1]

The Nitrogen Mustards are thought to function as cell cycle inhibitors by serving as alkylating agents for DNA.

The cell cycle inhibitor of the present invention may be a hydroxyurea. Hydroxyureas have the following general structure:

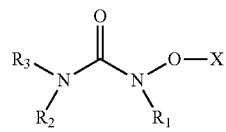

Suitable hydroxyureas are disclosed in, for example, U.S. Pat. No. 6,080,874, wherein $R_1$ is:

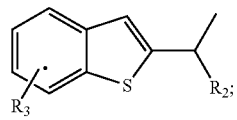

and $R_2$ is an alkyl group having 1-4 carbons and $R_3$ is one of H, acyl, methyl, ethyl, and mixtures thereof, such as a methylether.

Other suitable hydroxyureas are disclosed in, e.g., U.S. Pat. No. 5,665,768, wherein $R_1$ is a cycloalkenyl group, for example N-[3-[5-(4-fluorophenylthio)-furyl]-2-cyclopenten-1-yl]N-hydroxyurea; $R_2$ is H or an alkyl group having 1 to 4 carbons and $R_3$ is H; X is H or a cation.

Other suitable hydroxyureas are disclosed in, e.g., U.S. Pat. No. 4,299,778, wherein $R_1$ is a phenyl group substituted with on or more fluorine atoms; $R_2$ is a cyclopropyl group; and $R_3$ and X is H.

Other suitable hydroxyureas are disclosed in, e.g., U.S. Pat. No. 5,066,658, wherein $R_2$ and $R_3$ together with the adjacent nitrogen form:

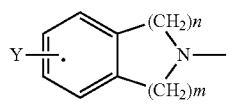

wherein m is 1 or 2, n is 0-2 and Y is an alkyl group.

In one aspect, the hydroxy urea has the structure:

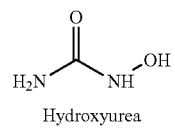

Hydroxyurea

Hydroxyureas are thought to function as Cell Cycle Inhibitors by serving to inhibit DNA synthesis.

In another aspect, the Cell Cycle Inhibitor is a Belomycin, such as Bleomycin A₂, which have the structures:

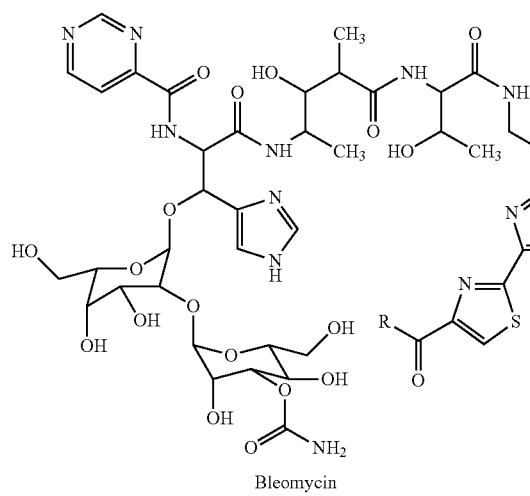

Bleomycin
R = terminal amine

Bleomycin A₂: R=(CH₃)₂S⁺(CH₂)₃NH—

Belomycins are thought to function as Cell Cycle Inhibitors by cleaving DNA. They have been shown useful in the treatment of cell proliferative disorder such as, e.g., penile cancer.

In another aspect, the Cell Cycle Inhibitor is a Mytomicin, such as Mitomycin C, or an analogue or derivative thereof, such as Porphyromycin. Suitable compounds have the structures:

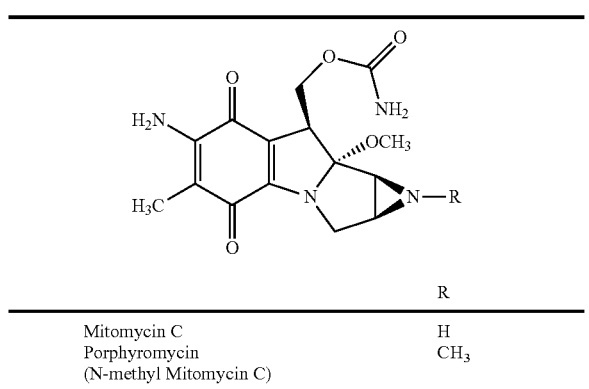

| | R |
|---|---|
| Mitomycin C | H |
| Porphyromycin (N-methyl Mitomycin C) | CH₃ |

These compounds are thought to function as Cell Cycle Inhibitors by serving as DNA alkylating agents.

In another aspect, the Cell Cycle Inhibitor is an Alkyl Sulfonate, such as Busulfan, or an analogue or derivative thereof, such as Treosulfan, Improsulfan, Piposulfan, and Pipobroman. Exemplary compounds have the structures:

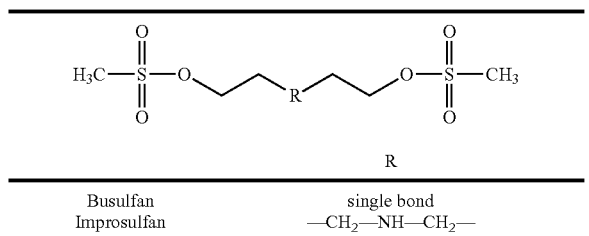

| | R |
|---|---|
| Busulfan | single bond |
| Improsulfan | —CH₂—NH—CH₂— |

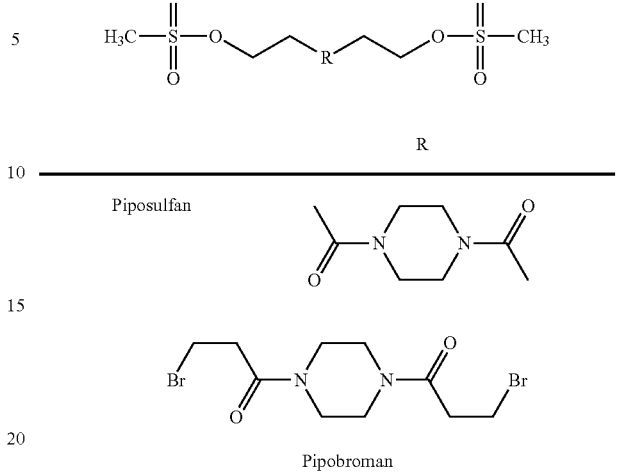

These compounds are thought to function as Cell Cycle Inhibitors by serving as DNA alkylating agents.

In another aspect, the Cell Cycle Inhibitor is a Benzamide. In yet another aspect, the Cell Cycle Inhibitor is a Nicotinamide. These compounds have the basic structure:

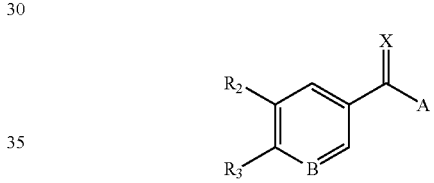

wherein X is either O or S; A is commonly NH₂ or it can be OH or an alkoxy group; B is N or C—R₄, where R₄ is H or an ether-linked hydroxylated alkane such as OCH₂CH₂OH, the alkane may be linear or branched and may contain one or more hydroxyl groups. Alternately, B may be N—R₅ in which case the double bond in the ring involving B is a single bond. R₅ may be H, and alkyl or an aryl group (see, e.g., U.S. Pat. No. 4,258,052); R₂ is H, OR₆, SR₆ or NHR₆, where R₆ is an alkyl group; and R₃ is H, a lower alkyl, an ether linked lower alkyl such as —O-Me or —O-Ethyl (see, e.g., U.S. Pat. No. 5,215,738).

Suitable Benzamide compounds have the structures:

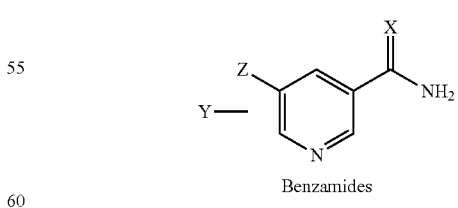

Benzamides
X = O or S
Y = H, OR, CH₃, acetoxy
Z = H, OR, SR, NHR
R = alkyl group where additional compounds are disclosed in U.S. Pat. No. 5,215,738, (listing some 32 compounds).

Suitable Nicotinamide compounds have the structures:

Nicotinamides

X = O or S
Z = H, OR, SR, NHR
R = alkyl group where additional compounds are disclosed in U.S. Pat. No. 5,215,738 (listing some 58 compounds, e.g., 5-OH nicotinamide, 5-aminonicotinamide, 5-(2,3-dihydroxypropoxy)nicotinamide), and compounds having the structures:

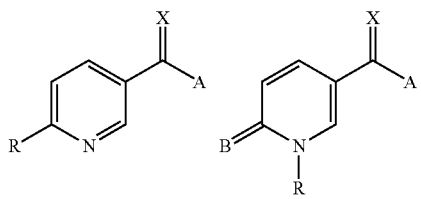

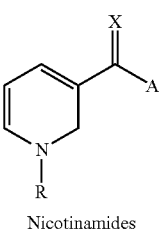

Nicotinamides

X = O or S (only O is described)
A = OH, NH$_2$, alkoxy
B = O
R = alkyl or aryl group and U.S. Pat. No. 4,258,052 (listing some 46 compounds, e.g., 1-methyl-6-keto-1,6-dihydronicotinic acid).

In one aspect, the Cell Cycle Inhibitor is a Tetrazine compound, such as Temozolomide, or an analogue or derivative thereof, including Dacarbazine. Suitable compounds have the structures:

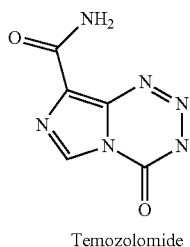 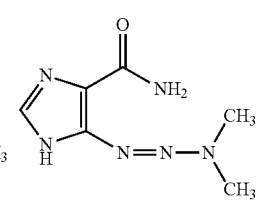

Temozolomide         Dacarbazine

Another suitable Tetrazine Compound is Procarbazine, including HCl and HBr salts, having the structure:

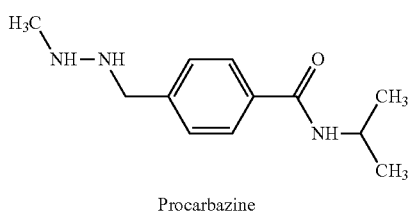 [SMILES: CNNCc1ccc(C(=O)NC(C)C)cc1]

Procarbazine

In another aspect, the Cell Cycle Inhibitor is Actinomycin D, or other members of this family, including Dactinomycin, Actinomycin C$_1$, Actinomycin C$_2$, Actinomycin C$_3$, and Actinomycin F$_1$. Suitable compounds have the structures:

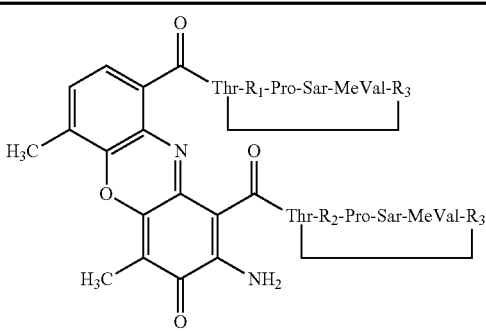

| | R$_1$ | R$_2$ | R$_3$ |
|---|---|---|---|
| Actinomycin D (C$_1$) | D-Val | D-Val | single bond |
| Actinomycin C$_2$ | D-Val | D-Alloisoleucine | O |
| Actinomycin C$_3$ | D-Alloisoleucine | D-Alloisoleucine | O |

In another aspect, the Cell Cycle Inhibitor is an Aziridine compound, such as Benzodepa, or an analogue or derivative thereof, including Meturedepa, Uredepa, and Carboquone. Suitable compounds have the structures:

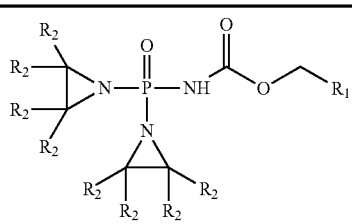

| | R$_1$ | R$_2$ |
|---|---|---|
| Benzodepa | phenyl | H |
| Meturedepa | CH$_3$ | CH$_3$ |
| Uredepa | CH$_3$ | H |

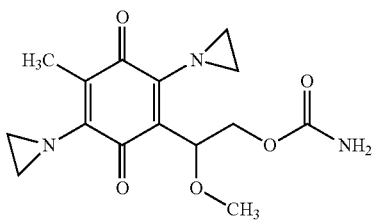

Carboquone

In another aspect, the Cell Cycle Inhibitor is a Halogenated Sugar, such as Mitolactol, or an analogue or derivative thereof, including Mitobronitol and Mannomustine. Suitable compounds have the structures:

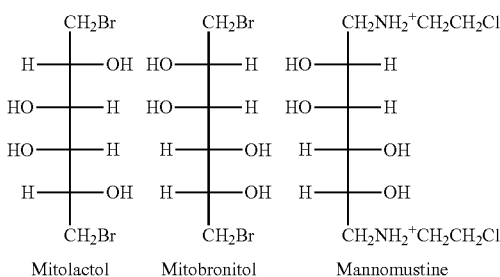

Mitolactol    Mitobronitol    Mannomustine

In another aspect, the Cell Cycle Inhibitor is a Diazo compound, such as Azaserine, or an analogue or derivative thereof, including 6-diazo-5-oxo-L-norleucine and 5-diazouracil (also a pyrimidine analog). Suitable compounds have the structures:

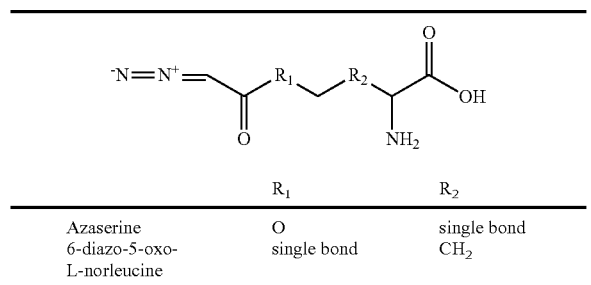

| | $R_1$ | $R_2$ |
|---|---|---|
| Azaserine | O | single bond |
| 6-diazo-5-oxo-L-norleucine | single bond | $CH_2$ |

Other compounds that may serve as Cell Cycle Inhibitors according to the present invention are Pazelliptine; Wortmannin; Metoclopramide; RSU; Buthionine sulfoxime; Tumeric; Curcumin; AG337, a thymidylate synthase inhibitor; Levamisole; Lentinan, a polysaccharide; Razoxane, an EDTA analog; Indomethacin; Chlorpromazine; α and β interferon; MnBOPP; Gadolinium texaphyrin; 4-amino-1,8-naphthalimide; Staurosporine derivative of CGP; and SR-2508.

Thus, in one aspect, the Cell Cycle Inhibitor is a DNA alkylating agent. In another aspect, the Cell Cycle Inhibitor is an anti-microtubule agent. In another aspect, the Cell Cycle Inhibitor is a Topoisomerase inhibitor. In another aspect, the Cell Cycle Inhibitor is a DNA cleaving agent. In another aspect, the Cell Cycle Inhibitor is an antimetabolite. In another aspect, the Cell Cycle Inhibitor functions by inhibiting adenosine deaminase (e.g., as a purine analog). In another aspect, the Cell Cycle Inhibitor functions by inhibiting purine ring synthesis and/or as a nucleotide interconversion inhibitor (e.g., as a purine analogue such as mercaptopurine). In another aspect, the Cell Cycle Inhibitor functions by inhibiting dihydrofolate reduction and/or as a thymidine monophosphate block (e.g., methotrexate). In another aspect, the Cell Cycle Inhibitor functions by causing DNA damage (e.g., Bleomycin). In another aspect, the Cell Cycle Inhibitor functions as a DNA intercalation agent and/or RNA synthesis inhibition (e.g., Doxorubicin). In another aspect, the Cell Cycle Inhibitor functions by inhibiting pyrimidine synthesis (e.g., N-phosphonoacetyl-L-Aspartate). In another aspect, the Cell Cycle Inhibitor functions by inhibiting ribonucleotides (e.g., hydroxyurea). In another aspect, the Cell Cycle Inhibitor functions by inhibiting thymidine monophosphate (e.g., 5-fluorouracil). In another aspect, the Cell Cycle Inhibitor functions by inhibiting DNA synthesis (e.g., Cytarabine).

In another aspect, the Cell Cycle Inhibitor functions by causing DNA adduct formation (e.g., platinum compounds). In another aspect, the Cell Cycle Inhibitor functions by inhibiting protein synthesis (e.g., L-Asparginase). In another aspect, the Cell Cycle Inhibitor functions by inhibiting microtubule function (e.g., taxanes). In another aspect, the Cell Cycle Inhibitors acts at one or more of the steps in the biological pathway shown in FIG. 3.

Additional Cell Cycle Inhibitors useful in the present invention, as well as a discussion of their mechanisms of action, may be found in Hardman J. G., Limbird L. E. Molinoff R. B., Ruddon R. W., Gilman A. G. editors, Chemotherapy of Neoplastic Diseases in Goodman and Gilman's The Pharmacological Basis of Therapeutics Ninth Edition, McGraw-Hill Health Professions Division, New York, 1996, pages 1225-1287. See also U.S. Pat. Nos. 3,387,001; 3,808, 297; 3,894,000; 3,991,045; 4,012,390; 4,057,548; 4,086,417; 4,144,237; 4,150,146; 4,210,584; 4,215,062; 4,250,189; 4,258,052; 4,259,242; 4,296,105; 4,299,778; 4,367,239; 4,374,414; 4,375,432; 4,472,379; 4,588,831; 4,639,456; 4,767,855; 4,828,831; 4,841,045; 4,841,085; 4,908,356; 4,923,876; 5,030,620; 5,034,320; 5,047,528; 5,066,658; 5,166,149; 5,190,929; 5,215,738; 5,292,731; 5,380,897; 5,382,582; 5,409,915; 5,440,056; 5,446,139; 5,472,956; 5,527,905; 5,552,156; 5,594,158; 5,602,140; 5,665,768; 5,843,903; 6,080,874; 6,096,923; and RE030561.

Numerous polypeptides, proteins and peptides, as well as nucleic acids that encode such proteins, can also be used therapeutically as cell cycle inhibitors. This is accomplished by delivery by a suitable vector or gene delivery vehicle which encodes a cell cycle inhibitor (Walther & Stein, Drugs 60(2):249-71, August 2000; Kim et al., Archives of Pharmacal Res. 24(1):1-15, February 2001; and Anwer et al., Critical Reviews in Therapeutic Drug Carrier Systems 17(4): 377-424, 2000. Genes encoding proteins that modulate cell cycle include the INK4 family of genes (U.S. Pat. No. 5,889, 169; U.S. Pat. No. 6,033,847), ARF-p19 (U.S. Pat. No. 5,723, 313), $p21^{WAF1/CIP1}$ and $p27^{KIP1}$ (WO 95/13375; WO 98/35022), $p27^{KIP1}$ (WO 97/38091), $p57^{KIP2}$ (U.S. Pat. No. 6,025,480), ATM/ATR (WO 99/04266), Gadd 45 (U.S. Pat. No. 5,858,679), Myt1 (U.S. Pat. No. 5,744,349), Wee1 (WO 99/49061) smad 3 and smad 4 (U.S. Pat. No. 6,100,032), 14-3-3σ (WO 99/31240), GSK30 (Stambolic, V. and Woodgett, J. R., Biochem Journal 303: 701-704, 1994), HDAC-1 (Furukawa, Y. et al., Cytogenet. Cell Genet. 73: 130-133, 1996; Taunton, J. et al., Science 272: 408-411, 1996), PTEN (WO 99/02704), p53 (U.S. Pat. No. 5,532,220), $p33^{ING1}$ (U.S. Pat. No. 5,986,078), Retinoblastoma (EPO 390530), and NF-1 (WO 92/00387).

A wide variety of gene delivery vehicles may be utilized to deliver and express the proteins described herein, including for example, viral vectors such as retroviral vectors (e.g., U.S. Pat. Nos. 5,591,624, 5,716,832, 5,817,491, 5,856,185, 5,888, 502, 6,013,517, and 6,133,029; as well as subclasses of retroviral vectors such as lentiviral vectors (e.g., PCT Publication Nos. WO 00/66759, WO 00/00600, WO 99/24465, WO 98/51810, WO 99/51754, WO 99/31251, WO 99/30742, and WO 99/15641)), alphavirus based vector systems (e.g., U.S. Pat. Nos. 5,789,245, 5,814,482, 5,843,723, and 6,015,686), adeno-associated virus-based system (e.g., U.S. Pat. Nos. 6,221,646, 6,180,613, 6,165,781, 6,156,303, 6,153,436, 6,093,570, 6,040,183, 5,989,540, 5,856,152, and 5,587,308) and adenovirus-based systems (e.g., U.S. Pat. Nos. 6,210, 939, 6,210,922, 6,203,975, 6,194,191, 6,140,087, 6,113,913, 6,080,569, 6,063,622, 6,040,174, 6,033,908, 6,033,885, 6,020,191, 6,020,172, 5,994,128, and 5,994,106), herpesvirus based or 'amplicon" systems (e.g., U.S. Pat. Nos. 5,928, 913, 5,501,979, 5,830,727, 5,661,033, 4,996,152 and 5,965, 441) and, "naked DNA" based systems (e.g., U.S. Pat. Nos. 5,580,859 and 5,910,488) (all of which are, as noted above, incorporated by reference in their entirety).

Within one aspect of the invention, ribozymes or antisense sequences (as well as gene therapy vehicles which can deliver such sequences) can be utilized as cell cycle inhibitors. One representative example of such inhibitors is disclosed in PCT Publication No. WO 00/32765 (which, as noted above, is incorporated by reference in its entirety).

5. Cyclin Dependent Protein Kinase Inhibitors

In another embodiment, the pharmacologically active compound is a cyclin dependent protein kinase inhibitor (e.g., R-roscovitine, CYC-101, CYC-103, CYC-400, MX-7065, alvocidib (4H-1-Benzopyran-4-one, 2-(2-chlorophenyl)-5,7-dihydroxy-8-(3-hydroxy-1-methyl-4-piperidinyl)-, cis-(–)-[CAS]), SU-9516, AG-12275, PD-0166285, CGP-79807, fascaplysin, GW-8510 (Benzenesulfonamide, 4-[[(Z)-(6,7-dihydro-7-oxo-8H-pyrrolo[2,3-g]benzothiazol-8-ylidene)methyl]amino]-N-(3-hydroxy-2,2-dimethylpropyl)-[CAS]), GW-491619, Indirubin 3' monoxime, GW8510) or an analogue or derivative thereof.

6. EGF (Epidermal Growth Factor) Receptor Kinase Inhibitors

In another embodiment, the pharmacologically active compound is an EGF (epidermal growth factor) kinase inhibitor (e.g., erlotinib (4-Quinazolinamine, N-(3-ethynylphenyl)-6,7-bis(2-methoxyethoxy)-, monohydrochloride [CAS]), VIATRIS (Viatris GMBH & Co., Germany), erbstatin, BIBX-1382, gefitinib (4-Quinazolinamine, N-(3-chloro-4-fluorophenyl)-7-methoxy-6-(3-(4-morpholinyl)propoxy) [CAS])) or an analogue or derivative thereof.

7. Elastase Inhibitors

In another embodiment, the pharmacologically active compound is an elastase inhibitor (e.g., ONO-6818, sivelestat sodium hydrate (Glycine, N-[2-[[[4-(2,2-dimethyl-1-oxopropoxy)phenyl]sulfonyl]amino]benzoyl]-[CAS]), erdosteine (Acetic acid, [[2-oxo-2-[(tetrahydro-2-oxo-3-thienyl)amino]ethyl]thio]-[CAS]), MDL-100948A, MDL-104238 (N-[4-(4-morpholinylcarbonyl)benzoyl]-L-valyl-N'-[3,3,4,4,4-pentafluoro-1-(1-methylethyl)-2-oxobutyl]-L-2-azetamide), MDL-27324 (L-Prolinamide, N-[[5-(dimethylamino)-1-naphthalenyl]sulfonyl]-L-alanyl-L-alanyl-N-[3,3,3-trifluoro-1-(1-methylethyl)-2-oxopropyl]-, (S)-[CAS]), SR-26831 (Thieno[3,2-c]pyridinium, 5-[(2-chlorophenyl)methyl]-2-(2,2-dimethyl-1-oxopropoxy)-4,5,6,7-tetrahydro-5-hydroxy-[CAS]), Win-68794, Win-63110, SSR-69071 (2-(9(2-Piperidinoethoxy)-4-oxo-4H-pyrido[1,2-a]pyrimidin-2-yloxymethyl)-4-(1-methylethyl)-6-methyoxy-1,2-benzisothiazol-3(2H)-one-1,1-dioxide), (N(Alpha)-(1-adamantylsulfonyl)N(epsilon)-succinyl-L-lysyl-L-prolyl-L-valinal), Ro-31-3537 (NAlpha-(1-adamantanesulphonyl)-N-(4-carboxybenzoyl)-L-lysyl-alanyl-L-valinal), R-665, FCE-28204, ((6R,7R)-2-(Benzoyloxy)-7-methoxy-3-methyl-4-pivaloyl-3-cephem 1,1-dioxide), 1,2-Benzisothiazol-3(2H)-one, dinitrophenyl), 1,1-dioxide [CAS], L-658758 (L-Proline, 1-[[3-[(acetyloxy)methyl]-7-methoxy-8-oxo-5-thia-1-azabicyclo[4.2.0]oct-2-en-2-yl]carbonyl]-, S,S-dioxide, (6R-cis)-[CAS]), L-659286 (Pyrrolidine, 1-[[7-methoxy-8-oxo-3-[[(1,2,5,6-tetrahydro-2-methyl-5,6-dioxo-1,2,4-triazin-3-yl)thio]methyl]-5-thia-1-azabicyclo[4.2.0]oct-2-en-2-yl]carbonyl]-, S,S-dioxide, (6R-cis)-[CAS]), L-680833 (Benzeneacetic acid, 4-[[3,3-diethyl-1-[[[1-(4-methylphenyl)butyl]amino]carbonyl]-4-oxo-2-azetidinyl]oxy]-, [S—(R*,S*)]-[CAS])) or an analogue or derivative thereof.

8. Factor Xa Inhibitors

In another embodiment, the pharmacologically active compound is a factor Xa inhibitor (e.g., CY-222, fondaparinux sodium (Alpha-D-Glucopyranoside, methyl O-2-deoxy-6-O-sulfo-2-(sulfoamino)-Alpha-D-glucopyranosyl-(1-4)-O-β-D-glucopyranuronosyl-(1-4)-O-2-deoxy-3,6-di-O-sulfo-2-(sulfoamino)-Alpha-D-glucopyranosyl-(1-4)-O-2-O-sulfo-Alpha-L-idopyranuronosyl-(1-4)-2-deoxy-2-(sulfoamino)-, 6-(hydrogen sulfate) [CAS]), danaparoid sodium) or an analogue or derivative thereof.

9. Farnesyltransferase Inhibitors

In another embodiment, the pharmacologically active compound is a farnesyltransferase inhibitor (e.g., dichlorobenzoprim (2,4-diamino-5-[4-(3,4-dichlorobenzylamino)-3-nitrophenyl]-6-ethylpyrimidine), B-581, B-956 (N-[8(R)-Amino-2(S)-benzyl-5(S)-isopropyl-9-sulfanyl-3(Z),6(E)-nonadienoyl]-L-methionine), OSI-754, perillyl alcohol (1-Cyclohexene-1-methanol, 4-(1-methylethenyl)-[CAS], RPR-114334, lonafarnib (1-Piperidinecarboxamide, 4-[2-[4-[(11R)-3,10-dibromo-8-chloro-6,11-dihydro-5H-benzo[5,6]cyclohepta[1,2-b]pyridin-11-yl]-1-piperidinyl]-2-oxoethyl]-[CAS]), Sch-48755, Sch-226374, (7,8-Dichloro-5H-dibenzo [b,e][1,4]diazepin-11-yl)-pyridin-3-ylmethylamine, J-104126, L-639749, L-731734 (Pentanamide, 2-[[2-[(2-amino-3-mercaptopropyl)amino]-3-methylpentyl]amino]-3-methyl-N-(tetrahydro-2-oxo-3-furanyl)-, [3S-[3R*[2R*[2R*(S*),3S],3R*]]]-[CAS]), L-744832 (Butanoic acid, 2-((2-((2-((2-amino-3-mercaptopropyl)amino)-3-methylpentyl)oxy)-1-oxo-3-phenylpropyl)amino)-4-(methylsulfonyl)-, 1-methylethyl ester, (2S-(1(R*(R*)),2R*(S*),3R*))-[CAS]), L-745631 (1-piperazinepropanethiol, β-amino-2-(2-methoxyethyl)-4-(1-naphthalenylcarbonyl)-, (βR,2S)-[CAS]), N-acetyl-N-naphthylmethyl-2(S)-[(1-(4-cyanobenzyl)-1H-imidazol-5-yl)acetyl]amino-3(S)-methylpentamine, (2Alpha)-2-hydroxy-24,25-dihydroxylanost-8-en-3-one, BMS-316810, UCF-1-C (2,4-Decadienamide, N-(5-hydroxy-5-(7-((2-hydroxy-5-oxo-1-cyclopenten-I-yl)amino-oxo-1,3,5-heptatrienyl)-2-oxo-7-oxabicyclo(4.1.0)hept-3-en-3-yl)-2,4,6-trimethyl-, (1S-(1Alpha,3(2E,4E,6S*),5Alpha,5(1E,3E,5E),6Alpha))-[CAS]), UCF-1,6-B) or an analogue or derivative thereof.

10. Fibrinogen Antagonists

In another embodiment, the pharmacologically active compound is a fibrinogen antagonist (e.g., 2(S)-[(p-Toluenesulfonyl)amino]-3-[[[5,6,7,8,-tetrahydro-4-oxo-5-[2-(piperidin-4-yl)ethyl]-4H-pyrazolo-[1,5-a][1,4]diazepin-2-yl]carbonyl]-amino]propionic acid, streptokinase (Kinase (enzyme-activating), strepto-[CAS]), urokinase (Kinase (enzyme-activating), uro-[CAS]), plasminogen activator, pamiteplase, monteplase, heberkinase, anistreplase, alteplase, pro-urokinase, picotamide (1,3-Benzenedicarboxamide, 4-methoxy-N,N'-bis(3-pyridinylmethyl)-[CAS])) or an analogue or derivative thereof.

11. Guanylate Cyclase Stimulants

In another embodiment, the pharmacologically active compound is a guanylate cyclase stimulant (e.g., isosorbide-5-mononitrate (D-Glucitol, 1,4:3,6-dianhydro-, 5-nitrate [CAS])) or an analogue or derivative thereof.

12. Heat Shock Protein 90 Antagonists

In another embodiment, the pharmacologically active compound is a heat shock protein 90 antagonist (e.g., geldanamycin; NSC-33050 (17-Allylaminogeldanamycin), rifabutin (Rifamycin XIV, 1',4-didehydro-1-deoxy-1,4-dihydro-5'-(2-methylpropyl)-1-oxo-[CAS]), 17AAG), or an analogue or derivative thereof.

13. HMGCoA Reductase Inhibitors

In another embodiment, the pharmacologically active compound is an HMGCoA reductase inhibitor (e.g., BCP-671, BB-476, fluvastatin (6-Heptenoic acid, 7-[3-(4-fluorophenyl)-1-(1-methylethyl)-1H-indol-2-yl]-3,5-dihydroxy-, monosodium salt, [R*,S*-(E)]-(±)-[CAS]), dalvastatin (2H-Pyran-2-one, 6-(2-(2-(2-(4-fluoro-3-methylphenyl)-4,4,6,6-tetramethyl-1-cyclohexen-1-yl)ethenyl)tetrahydro-4-hydroxy-, (4Alpha,6β(E))-(+/−)-[CAS]), glenvastatin (2H-Pyran-2-one, 6-[2-[4-(4-fluorophenyl)-2-(1-methylethyl)-6-phenyl-3-pyridinyl]ethenyl]tetrahydro-4-hydroxy-, [4R-[4Alpha,6β(E)]]-[CAS]), S-2468, N-(1-oxododecyl)-4Alpha,10-dimethyl-8-aza-trans-decal-3β-ol, atorvastatin calcium (1H-Pyrrole-1-heptanoic acid, 2-(4-fluorophenyl)-β,delta-dihydroxy-5-(1-methylethyl)-3-phenyl-4-[(phenylamino)carbonyl]-, calcium salt [R—(R*,R*)]-[CAS]), CP-83101 (6,8-Nonadienoic acid, 3,5-dihydroxy-9,9-diphenyl-, methyl ester, [R*,S*-(E)]-(+/−)-[CAS]), pravastatin (1-Naphthaleneheptanoic acid, 1,2,6,7,8,8a-hexahydro-β,delta,6-trihydroxy-2-methyl-8-(2-methyl-1-oxobutoxy)-, monosodium salt, [1S-[1Alpha(βS*,deltaS*),2Alpha,6Alpha,8β(R*),8aAlpha]]-[CAS]), U-20685, pitavastatin (6-Heptenoic acid, 7-[2-cyclopropyl-4-(4-fluorophenyl)-3-quinolinyl]-3,5-dihydroxy-, calcium salt (2:1), [S—[R*,S*-(E)]]-[CAS]), N-((1-methylpropyl)carbonyl)-8-[2-(tetrahydro-4-hydroxy-6-oxo-2H-pyran-2-yl)ethyl]-perhydro-isoquinoline, dihydromevinolin (Butanoic acid, 2-methyl-, 1,2,3,4,4a,7,8,8a-octahydro-3,7-dimethyl-8-[2-(tetrahydro-4-hydroxy-6-oxo-2H-pyran-2-yl)ethyl]-1-naphthalenylester[1Alpha(R*),3Alpha,4aAlpha, 7β,8β(2S*,4S*),8aβ]]-[CAS]), HBS-107, dihydromevinolin (Butanoic acid, 2-methyl-, 1,2,3,4,4a,7,8,8a-octahydro-3,7-dimethyl-8-[2-(tetrahydro-4-hydroxy-6-oxo-2H-pyran-2-yl)ethyl]-1-naphthalenyl ester[1Alpha(R*),3Alpha,4aAlpha,7β,8β(2S*,4S*),8aβ]]-[CAS]), L-669262 (Butanoic acid, 2,2-dimethyl-, 1,2,6,7,8,8a-hexahydro-3,7-dimethyl-6-oxo-8-[2-(tetrahydro-4-hydroxy-6-oxo-2H-pyran-2-yl)ethyl]-1-naphthalenyl[1S-[1Alpha,7β,8β(2S*,4S*),8aβ]]-[CAS]), simvastatin (Butanoic acid, 2,2-dimethyl-, 1,2,3,7,8,8a-hexahydro-3,7-dimethyl-8-[2-(tetrahydro-4-hydroxy-6-oxo-2H-pyran-2-yl)ethyl]-1-naphthalenyl ester, [1S-[1Alpha,3Alpha,7β,8β(2S*,4S*),8aβ]]-[CAS]), rosuvastatin calcium (6-Heptenoic acid, 7-(4-(4-fluorophenyl)-6-(1-methylethyl)-2-(methyl(methylsulfonyl)amino)-5-pyrimdinyl)-3,5-dihydroxy-calcium salt (2:1) (S—(R*, S*-(E))) [CAS]), meglutol (2-hydroxy-2-methyl-1,3-propandicarboxylic acid), lovastatin (Butanoic acid, 2-methyl-, 1,2,3,7,8,8a-hexahydro-3,7-dimethyl-8-[2-(tetrahydro-4-hydroxy-6-oxo-2H-pyran-2-yl)ethyl]-1-naphthalenyl ester, [1S-[1.alpha.(R*),3Alpha,7β,8β(2S*,4S*),8aβ]]-[CAS])) or an analogue or derivative thereof.

14. Hydroorotate Dehydrogenase Inhibitors

In another embodiment, the pharmacologically active compound is a hydroorotate dehydrogenase inhibitor (e.g., leflunomide (4-Isoxazolecarboxamide, 5-methyl-N-[4-(trifluoromethyl)phenyl]-[CAS]), laflunimus (2-Propenamide, 2-cyano-3-cyclopropyl-3-hydroxy-N-(3-methyl-4(trifluoromethyl)phenyl)-, (Z)-[CAS])) or an analogue or derivative thereof.

15. IKK2 Inhibitors

In another embodiment, the pharmacologically active compound is an IKK2 inhibitor (e.g., MLN-120B, SPC-839) or an analogue or derivative thereof.

16. IL-1, ICE, and IRAK Antagonists

In another embodiment, the pharmacologically active compound is an IL-1, ICE ((aryl)acyloxymethyl ketone) & IRAK antagonist (e.g., VX-765 (Vertex Pharmaceuticals, Cambridge, Mass.), VX-740 (Vertex Pharmaceuticals), E-5090 (2-Propenoic acid, 3-(5-ethyl-4-hydroxy-3-methoxy-1-naphthalenyl)-2-methyl-, (Z)-[CAS]), CH-164, CH-172, CH-490, AMG-719, iguratimod (N-[3-(Formylamino)-4-oxo-6-phenoxy-4H-chromen-7-yl]methanesulfonamide), AV94-88, pralnacasan (6H-Pyridazino(1,2-a)(1,2)diazepine-1-carboxamide, N-((2R,3S)-2-ethoxytetrahydro-5-oxo-3-furanyl)octahydro-9-((1-isoquinolinylcarbonyl)amino)-6,10-dioxo-, (1S,9S)-[CAS]), (2S-cis)-5-[Benzyloxycarbonylamino-1,2,4,5,6,7-hexahydro-4-(oxoazepino[3,2,1-hi]indole-2-carbonyl)-amino]-4-oxobutanoic acid, AVE-9488, ESONARIMOD (Taisho Pharmaceutical Co., Ltd., Japan) (Benzenebutanoic acid, Alpha-[(acetylthio)methyl]-4-methyl-Gamma-oxo-[CAS]), pralnacasan (6H-Pyridazino(1,2-a)(1,2)diazepine-1-carboxamide, N-((2R,3S)-2-ethoxytetrahydro-5-oxo-3-furanyl)octahydro-9-((1-isoquinolinylcarbonyl)amino)-6,10-dioxo-, (1S,9S)-[CAS]), tranexamic acid (Cyclohexanecarboxylic acid, 4-(aminomethyl)-, trans-[CAS]), Win-72052, Tomazarit (Ro-31-3948) (Propanoic acid, 2-[[2-(4-chlorophenyl)-4-methyl-5-oxazolyl]methoxy]-2-methyl-[CAS]), PD-163594, SDZ-224-015 (L-Alaninamide N-((phenylmethoxy)carbonyl)-L-valyl-N-((1S)-3-((2,6-dichlorobenzoyl)oxy)-1-(2-ethoxy-2-oxoethyl)-2-oxopropyl)-[CAS]), L-709049 (L-Alaninamide, N-acetyl-L-tyrosyl-L-valyl-N-(2-carboxy-1-formylethyl)-, (S)-[CAS]), TA-383 (1H-Imidazole, 2-(4-chlorophenyl)-4,5-dihydro-4,5-diphenyl-, monohydrochloride, cis-[CAS]), EI-1507-1 (6a,12a-Epoxybenz[a]anthracen-1,12(2H,7H)-dione, 3,4-dihydro-3,7-dihydroxy-8-methoxy-3-methyl-[CAS]), Ethyl 4-(3,4-dimethoxyphenyl)-6,7-dimethoxy-2-(1,2,4-triazol-1-yl methyl)quinoline-3-carboxylate, EI-1941-1, TJ-114, anakinra (Interleukin 1 receptor antagonist (human isoformxreduced), N2-L-methionyl-[CAS])) or an analogue or derivative thereof.

17. IL-4 Agonists

In another embodiment, the pharmacologically active compound is an IL-4 agonist (e.g., glatiramir acetate (L-Glutamic acid, polymer with L-alanine, L-lysine and L-tyrosine, acetate (salt) [CAS])) or an analogue or derivative thereof.

18. Immunomodulatory Agents

In another embodiment, the pharmacologically active compound is an immunomodulatory agent (e.g. Biolimus, leflunamide, ABT-578, methylsulfamic acid 3-(2-methoxyphenoxy)-2-[[(methylamino)sulfonyl]oxy]propyl ester, sirolimus, CCI-779 (Rapamycin 42-(3-hydroxy-2-(hydroxymethyl)-2-methylpropanoate) [CAS]), LF-15-0195, NPC15669 (L-Leucine, N-[[(2,7-dimethyl-9H-fluoren-9-yl)methoxy]carbonyl]-[CAS]), NPC-15670 (L-Leucine, N-[[(4,5-dimethyl-9H-fluoren-9-yl)methoxy]carbonyl]-[CAS]), NPC-16570 (4-[2-(Fluoren-9-yl)ethyloxy-carbonyl]aminobenzoic acid), sufosfamide (Ethanol, 2-[[3-(2-chloroethyl)

tetrahydro-2H-1,3,2-oxazaphosphorin-2-yl]amino]-, methanesulfonate (ester), P-oxide [CAS]), tresperimus (2-[N-[4-(3-Aminopropylamino)butyl]carbamoyloxy]-N-(6-guanidinohexyl)acetamide), 4-[2-(Fluoren-9-yl) ethoxycarbonylamino]-benzo-hydroxamic acid, laquinimod, PBI-1411, azathioprine (6-[(1-Methyl-4-nitro-1H-imidazol-5-yl)thio]-1H-purine), PB10032, beclometasone, MDL-28842 (9H-Purin-6-amine, 9-(5-deoxy-5-fluoro-β-D-threo-pent-4-enofuranosyl)-, (Z)-[CAS]), FK-788, AVE-1726, ZK-90695, ZK-90695, Ro-54864, didemnin-B, Illinois (Didemnin A, N-[1-(2-hydroxy-1-oxopropyl)-L-prolyl]-, (S)-[CAS]), SDZ-62-826 (Ethanaminium, 2-[[hydroxy[[1-[(octadecyloxy)carbonyl]-3-piperidinyl]methoxy]phosphinyl]oxy]-N,N,N-trimethyl-, inner salt [CAS]), argyrin B ((4S,7S,13R,22R)-β-Ethyl-4-(1H-indol-3-ylmethyl)-7-(4-methoxy-1H-indol-3-ylmethyl)18,22-dimethyl-16-methylene-24-thia-3,6,9,12,15,18,21,26-octaazabicyclo[21.2.1]-hexacosa-1(25),23(26)-diene-2,5,8,11,14,17,20-heptaone [CAS]), everolimus (Rapamycin, 42-O-(2-hydroxyethyl)-[CAS]), SAR-943, L-687795, 6-[(4-Chlorophenyl)sulfinyl]-2,3-dihydro-2-(4-methoxy-phenyl)-5-methyl-3-oxo-4-pyridazinecarbonitrile, 91Y78 (1H-Imidazo[4,5-c]pyridin-4-amine, 1-β-D-ribofuranosyl-[CAS]), auranofin (Gold, (1-thio-β-D-glucopyranose 2,3,4,6-tetraacetato-S)(triethylphosphine)-[CAS]), 27-O-Demethylrapamycin, tipredane (Androsta-1,4-dien-3-one, 17-(ethylthio)-9-fluoro-11-hydroxy-17-(methylthio)-, (11β,17Alpha)-[CAS]), AI-402, LY-178002 (4-Thiazolidinone, 5-[[3,5-bis(1,1-dimethylethyl)-4-hydroxyphenyl]methylene]-[CAS]), SM-8849 (2-Thiazolamine, 4-O-(2-fluoro[1,1'-biphenyl]-4-yl)ethyl]-N-methyl-[CAS]), piceatannol, resveratrol, triamcinolone acetonide (Pregna-1,4-diene-3,20-dione, 9-fluoro-11,21-dihydroxy-16,17-[(1-methylethylidene)bis(oxy)]-, (11β,16Alpha)-[CAS]), ciclosporin (Cyclosporin A-[CAS]), tacrolimus (15,19-Epoxy-3H-pyrido(2,1-c)(1,4)oxaazacyclotricosine-1,7,20,21(4H,23H)-tetrone, 5,6,8,11,12,13,14,15,16,17,18, 19,24,25,26,26a-hexadecahydro-5,19-dihydroxy-3-(2-(4-hydroxy-3-methoxycyclohexyl)-1-methylethenyl)-14,16-dimethoxy-4,10,12,18-tetramethyl-8-(2-propenyl)-, (3S-(3R*(E(1S*,3S*,4S*)),4S*,5R*,8S*,9E,12R*,14R*,15S*, 16R*,18S*,19S*,26aR*))-[CAS]), gusperimus (Heptanamide, 7-[(aminoiminomethyl)amino]-N-[2-[[4-[(3-aminopropyl)amino]butyl]amino]-1-hydroxy-2-oxoethyl]-, (+/−)-[CAS]), tixocortol pivalate (Pregn-4-ene-3,20-dione, 21-[(2,2-dimethyl-1-oxopropyl)thio]-11,17-dihydroxy-, (11β)-[CAS]), alefacept (1-92 LFA-3 (Antigen) (human) fusion protein with immunoglobulin G1 (human hinge-CH2-CH3 Gamma1-chain), dimmer), halobetasol propionate (Pregna-1,4-diene-3,20-dione, 21-chloro-6,9-difluoro-11-hydroxy-16-methyl-17-(1-oxopropoxy)-, (6Alpha,11β,16β)-[CAS]), iloprost trometamol (Pentanoic acid, 5-[hexahydro-5-hydroxy-4-(3-hydroxy-4-methyl-1-octen-6-ynyl)-2(1H)-pentalenylidene]-[CAS]), beraprost (1H-Cyclopenta[b] benzofuran-5-butanoic acid, 2,3,3a,8b-tetrahydro-2-hydroxy-1-(3-hydroxy-4-methyl-1-octen-6-ynyl)-[CAS]), rimexolone (Androsta-1,4-dien-3-one,11-hydroxy-16,17-dimethyl-17-(1-oxopropyl)-, (11β,16Alpha,17β)-[CAS]), dexamethasone (Pregna-1,4-diene-3,20-dione,9-fluoro-11, 17,21-trihydroxy-16-methyl-, (11β,16Alpha)-[CAS]), sulindac (cis-5-fluoro-2-methyl-1-[(p-methylsulfinyl)benzylidene]indene-3-acetic acid), proglumetacin (1H-Indole-3-acetic acid, 1-(4-chlorobenzoyl)-5-methoxy-2-methyl-, 2-(4-(3-((4-(benzoylamino)-5-(dipropylamino)-1,5-dioxopentyl) oxy)propyl)-1-piperazinyl)ethylester, (+/−)-[CAS]), alclometasone dipropionate (Pregna-1,4-diene-3,20-dione, 7-chloro-11-hydroxy-16-methyl-17,21-bis(1-oxopropoxy)-, (7Alpha,11β,16Alpha)-[CAS]), pimecrolimus (15,19-Epoxy-3H-pyrido(2,1-c)(1,4)oxaazacyclotricosine-1,7,20,21 (4H,23H)-tetrone, 3-(2-(4-chloro-3-methoxycyclohexyl)-1-methyletheny)-8-ethyl-5,6,8,11,12,13,14,15,16,17,18,19,24, 25,26,26a-hexadecahydro-5,19-dihydroxy-14,16-dimethoxy-4,10,12,18-tetramethyl-, (3S-(3R*(E(1S*,3S*, 4R*)),4S*,5R*,8S*,9E,12R*,14R*,15S*,16R*,18S*,19S*, 26aR*))-[CAS]), hydrocortisone-17-butyrate (Pregn-4-ene-3,20-dione, 11,21-dihydroxy-17-(1-oxobutoxy)-, (11β)-[CAS]), mitoxantrone (9,10-Anthracenedione, 1,4-dihydroxy-5,8-bis[[2-[(2-hydroxyethyl)amino]ethyl] amino]-[CAS]), mizoribine (1H-Imidazole-4-carboxamide, 5-hydroxy-1-β-D-ribofuranosyl-[CAS]), prednicarbate (Pregna-1,4-diene-3,20-dione, 17-[(ethoxycarbonyl)oxy]-11-hydroxy-21-(1-oxopropoxy)-, (11β)-[CAS]), lobenzarit (Benzoic acid, 2-[(2-carboxyphenyl)amino]-4-chloro-[CAS]), glucametacin (D-Glucose, 2-[[[1-(4-chlorobenzoyl)-5-methoxy-2-methyl-1H-indol-3-yl]acetyl]amino]-2-deoxy-[CAS]), fluocortolone monohydrate ((6Alpha)-fluoro-16Alpha-methylpregna-1,4-dien-11β,21-diol-3,20-dione), fluocortin butyl (Pregna-1,4-dien-21-oic acid, 6-fluoro-11-hydroxy-16-methyl-3,20-dioxo-, butyl ester, (6Alpha,11β, 16Alpha)-[CAS]), difluprednate (Pregna-1,4-diene-3,20-dione, 21-(acetyloxy)-6,9-difluoro-11-hydroxy-17-(1-oxobutoxy)-, (6Alpha,11β)-[CAS]), diflorasone diacetate (Pregna-1,4-diene-3,20-dione, 17,21-bis(acetyloxy)-6,9-difluoro-11-hydroxy-16-methyl-, (6Alpha,11β,16β)-[CAS]), dexamethasone valerate (Pregna-1,4-diene-3,20-dione, 9-fluoro-11,21-dihydroxy-16-methyl-17-[(1-oxopentyl) oxy]-, (11β,16Alpha)-[CAS]), methylprednisolone, deprodone propionate (Pregna-1,4-diene-3,20-dione, 11-hydroxy-17-(1-oxopropoxy)-, (11.beta.)-[CAS]), bucillamine (L-Cysteine, N-(2-mercapto-2-methyl-1-oxopropyl)-[CAS]), amcinonide (Benzeneacetic acid, 2-amino-3-benzoyl-, monosodium salt, monohydrate [CAS]), acemetacin (1H-Indole-3-acetic acid, 1-(4-chlorobenzoyl)-5-methoxy-2-methyl-, carboxymethyl ester [CAS])) or an analogue or derivative thereof. Further, analogues of rapamycin include tacrolimus and derivatives thereof (e.g., EP0184162B1 and U.S. Pat. No. 6,258,823) everolimus and derivatives thereof (e.g., U.S. Pat. No. 5,665,772). Further representative examples of sirolimus analogues and derivatives include ABT-578 and those found in PCT Publication Nos. WO 97/10502, WO 96/41807, WO 96/35423, WO 96/03430, WO 96/00282, WO 95/16691, WO 95/15328, WO 95/07468, WO 95/04738, WO 95/04060, WO 94/25022, WO 94/21644, WO 94/18207, WO 94/10843, WO 94/09010, WO 94/04540, WO 94/02485, WO 94/02137, WO 94/02136, WO 93/25533, WO 93/18043, WO 93/13663, WO 93/11130, WO 93/10122, WO 93/04680, WO 92/14737, and WO 92/05179. Representative U.S. patents include U.S. Pat. Nos. 6,342,507; 5,985,890; 5,604,234; 5,597,715; 5,583,139; 5,563,172; 5,561,228; 5,561,137; 5,541,193; 5,541,189; 5,534,632; 5,527,907; 5,484,799; 5,457,194; 5,457,182; 5,362,735; 5,324,644; 5,318,895; 5,310,903; 5,310,901; 5,258,389; 5,252,732; 5,247,076; 5,225,403; 5,221,625; 5,210,030; 5,208,241;

5,200,411; 5,198,421; 5,147,877; 5,140,018; 5,116,756; 5,109,112; 5,093,338; and 5,091,389.

The structures of sirolimus, everolimus, and tacrolimus are provided below:

| Name | Code Name | Company | Structure |
|---|---|---|---|
| Everolimus | SAR-943 | Novartis | See below |
| Sirolimus Rapamune Rapamycin | AY-22989 NSC-226080 | Wyeth | See below |
| Tacrolimus | FK506 | Fujusawa | See below |

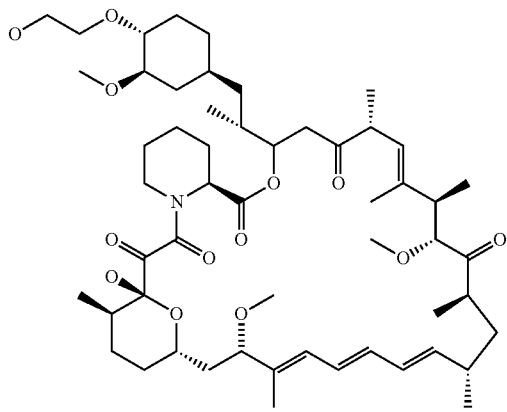 [SMILES: CO[C@H]1C[C@@H]2CC[C@@H](C)[C@@](O)(O2)C(=O)C(=O)N2CCCC[C@H]2C(=O)OC([C@H](C)C[C@@H]2CC[C@@H](OCCO)[C@H](OC)C2)CC(=O)[C@H](C)/C=C(\C)[C@@H](C)[C@@H](OC)C(=O)[C@H](C)C[C@H](C)/C=C/C=C/C=C/1C]

Everolimus

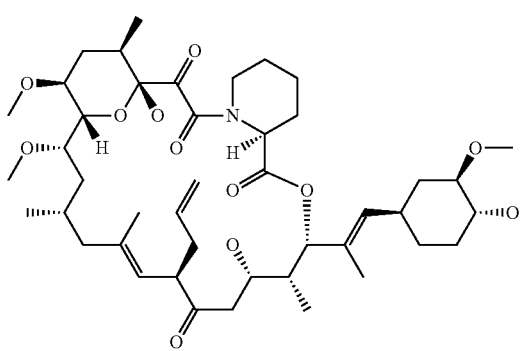

Tacrolimus

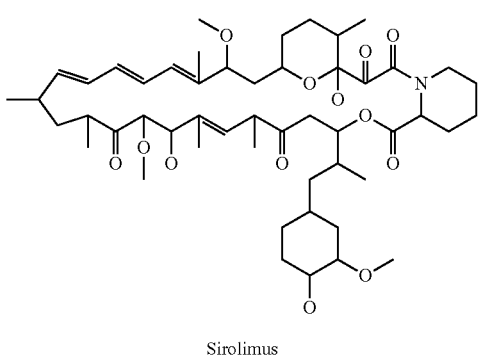

Sirolimus

19. Inosine Monophosphate Dehydrogenase Inhibitors

In another embodiment, the pharmacologically active compound is an inosine monophosphate dehydrogenase inhibitor (e.g., Mycophenolate Mofetil (4-Hexenoic acid, 6-(1,3-dihydro-4-hydroxy-6-methoxy-7-methyl-3-oxo-5-isobenzofuranyl)-4-methyl-, 2-(4-morpholinyl)ethyl ester, (E)-[CAS]), ribavirin (1H-1,2,4-Triazole-3-carboxamide, 1-β-D-ribofuranosyl-[CAS]), tiazofurin (4-Thiazolecarboxamide, 2-β-D-ribofuranosyl-[CAS]), viramidine, aminothiadiazole, thiophenfurin, tiazofurin) or an analogue or derivative thereof. Additional representative examples are included in U.S. Pat. Nos. 5,536,747; 5,807,876; 5,932,600; 6,054,472, 6,128,582; 6,344,465; 6,395,763; 6,399,773; 6,420,403; 6,479,628; 6,498,178; 6,514,979; 6,518,291; 6,541,496; 6,596,747; 6,617,323; and 6,624,184, U.S. Publication Nos. 2002/0040022A1, 2002/0052513A1, 2002/0055483A1, 2002/0068346A1, 2002/0111378A1, 2002/0111495A1, 2002/0123520A1, 2002/0143176A1, 2002/0147160A1, 2002/0161038A1, 2002/0173491 A1, 2002/0183315A1, 2002/0193612A1, 2003/0027845A1, 2003/0068302A1, 2003/0105073A1, 2003/0130254A1, 2003/0143197A1, 2003/0144300A1, 2003/0166201A1, 2003/0181497A1, 2003/0186974A1, 2003/0186989A1, and 2003/0195202A1, and PCT Publication Nos. WO 00/24725A1, WO 00/25780A1, WO 00/26197A1, WO 00/51615A1, WO 0056331A1, WO 00/73288A1, WO 01/00622A1, WO 01/66706A1, WO 01/79246A2, WO 01/81340A2, WO 01/85952A2, WO 02/16382A1, WO 02/18369A2, WO 02/51814A1, WO 02/57287A2, WO 02/57425A2, WO 02/60875A1, WO 02/60896A1, WO 02/60898A1, WO 02/68058A2, WO 03/20298A1, WO 03/37349A1, WO 03/39548A1, WO 03/45901 A2, WO 03/47512A2, WO 03/53958A1, WO 03/55447A2, WO 03/59269A2, WO 03/63573A2, WO 03/87071A1, WO 90/01545A1, WO 97/40028A1, WO 97/41211A1, WO 98/40381A1, and WO 99/55663A1.

20. Leukotriene Inhibitors

In another embodiment, the pharmacologically active compound is a leukotreine inhibitor (e.g., DTI-0026, ONO-4057(Benzenepropanoic acid, 2-(4-carboxybutoxy)-6-[[6-(4-methoxyphenyl)-5-hexenyl]oxy]-, (E)-[CAS]), ONO-LB-448, pirodomast 1,8-Naphthyridin-2(1H)-one, 4-hydroxy-1-phenyl-3-(1-pyrrolidinyl)-[CAS], Sch-40120 (Benzo[b][1,8] naphthyridin-5(7H)-one, 10-(3-chlorophenyl)-6,8,9,10-tetrahydro-[CAS]), L-656224 (4-Benzofuranol, 7-chloro-2-[(4-methoxyphenyl)methyl]-3-methyl-5-propyl-[CAS]), MAFP (methyl arachidonyl fluorophosphonate), ontazolast (2-Benzoxazolamine, N[2-cyclohexyl-1-(2-pyridinyl)ethyl]-5-methyl-, (S)-[CAS]), amelubant (Carbamic acid, ((4-((3-((4-(1-(4-hydroxyphenyl)-1-methylethyl)phenoxy)methyl) phenyl)methoxy)phenyl)iminomethyl)-ethyl ester [CAS]), SB-201993 (Benzoic acid, 3-[[[[6-[(1E)-2-carboxyethenyl]-5-[[8-(4-methoxyphenyl)octyl]oxy]-2-pyridinyl]methyl] thio]methyl]-[CAS]), LY-203647 (Ethanone, 1-[2-hydroxy-3-propyl-4-[4-[2-[4-(1H-tetrazol-5-yl)butyl]-2H-tetrazol-5-yl]butoxy]phenyl]-[CAS]), LY-210073, LY-223982 (Benzenepropanoic acid, 5-(3-carboxybenzoyl)-2-[[6-(4-methoxyphenyl)-5-hexenyl]oxy]-, (E)-[CAS]), LY-293111 (Benzoic acid, 2-[3-[3-[(5-ethyl-4'-fluoro-2-hydroxy[1,1'-biphenyl]-4-yl)oxy]propoxy]-2-propylphenoxy]-[CAS]), SM-9064 (Pyrrolidine, 1-[4,11-dihydroxy-13-(4-methoxyphenyl)-1-oxo-5,7,9-tridecatrienyl]-, (E,E,E)-[CAS]), T-0757 (2,6-Octadienamide, N-(4-hydroxy-3,5-dimethylphenyl)-3,7-dimethyl-, (2E)-[CAS])) or an analogue or derivative thereof.

21. MCP-1 Antagonists

In another embodiment, the pharmacologically active compound is a MCP-1 antagonist (e.g., nitronaproxen (2-Napthaleneacetic acid, 6-methoxy-Alpha-methyl 4-(nitrooxy)butyl ester (AlphaS)-[CAS]), Bindarit (2-(1-benzylindazol-3-ylmethoxy)-2-methylpropanoic acid), 1-alpha-25 dihydroxy vitamin $D_3$) or an analogue or derivative thereof.

22. MMP Inhibitors

In another embodiment, the pharmacologically active compound is a MMP inhibitor (e.g., D-9120, doxycycline (2-Naphthacenecarboxamide, 4-(dimethylamino)-1,4,4a,5,5a,6,11,12a-octahydro-3,5,10,12,12a-pentahydroxy-6-methyl-1,11-dioxo-[4S-(4Alpha,4aAlpha,5Alpha,5aAlpha,6Alpha,12aAlpha)]-[CAS]), BB-2827, BB-1101 (25-allyl-N-1-hydroxy-3R-isobutyl-N4-(1S-methylcarbamoyl-2-phenylethyl)-succinamide), BB-2983, solimastat (N'-[2,2-Dimethyl-1(S)—[N-(2-pyridyl)carbamoyl]propyl]-N4-hydroxy-2(R)-isobutyl-3(S)-methoxysuccinamide), BATIMASTAT (Butanediamide, N4-hydroxy-N-1-[2-(methylamino)-2-oxo-1-(phenylmethyl)ethyl]-2-(2-methylpropyl)-3-[(2-thienylthio)methyl]-, [2R-[1(S*),2R*,3S*]]-[CAS]; British Biotech, UK), CH-138, CH-5902, D-1927, D-5410, EF-13 (Gamma-linolenic acid lithium salt), CMT-3 (2-Naphthacenecarboxamide, 1,4,4a,5,5a,6,11,12a-octahydro-3,10,12,12a-tetrahydroxy-1,1'-dioxo-, (4aS,5aR,12aS)-[CAS]), MARIMASTAT (N-[2,2-Dimethyl-1(S)—(N-methylcarbamoyl)propyl]-N,3(S)-dihydroxy-2(R)-isobutylsuccinamide, British Biotech, UK), TIMP'S,ONO-4817, rebimastat (L-Valinamide, N-((2S)-2-mercapto-1-oxo-4-(3,4,4-trimethyl-2,5-dioxo-1-imidazolidinyl)butyl)-L-leucyl-N,3-dimethyl-[CAS]), PS-508, CH-715, nimesulide (Methanesulfonamide, N-(4-nitro-2-phenoxyphenyl)-[CAS]), hexahydro-2-[2(R)-[1(RS)-(hydroxycarbamoyl)-4-phenylbutyl]nonanoyl]-N-(2,2,6,6-etramethyl-4-piperidinyl)-3(S)-pyridazine carboxamide, Rs-113-080, Ro-1130830, Cipemastat (1-Piperidinebutanamide, β-(cyclopentylmethyl)-N-hydroxy-Gamma-oxo-Alpha-[(3,4,4-trimethyl-2,5-dioxo-1-imidazolidinyl)methyl]-,(AlphaR,βR)-[CAS]), 5-(4'-biphenyl)-5-[N-(4-nitrophenyl)piperazinyl]barbituric acid, 6-methoxy-1,2,3,4-tetrahydronorharman-1-carboxylic acid, Ro-31-4724 (L-Alanine, N-[2-[2-(hydroxyamino)-2-oxoethyl]-4-methyl-1-oxopentyl]-L-leucyl-, ethyl ester[CAS]), prinomastat (3-Thiomorpholinecarboxamide, N-hydroxy-2,2-dimethyl-4-((4-(4-pyridinyloxy)phenyl)sulfonyl)-, (3R)-[CAS]), AG-3433 (1H-Pyrrole-3-propanic acid, 1-(4'-cyano[1,1'-biphenyl]-4-yl)-b-[[[(3S)-tetrahydro-4,4-dimethyl-2-oxo-3-furanyl]amino]carbonyl]-, phenylmethyl ester, (bS)-[CAS]), PNU-142769 (2H-Isoindole-2-butanamide, 1,3-dihydro-N-hydroxy-Alpha-[(3S)-3-(2-methylpropyl)-2-oxo-1-(2-phenylethyl)-3-pyrrolidinyl]-1,3-dioxo-, (AlphaR)-[CAS]), (S)-1-[2-[[[(4,5-Dihydro-5-thioxo-1,3,4-thiadiazol-2-yl)amino]-carbonyl]amino]-1-oxo-3-(pentafluorophenyl)propyl]-4-(2-pyridinyl)piperazine, SU-5402 (1H-Pyrrole-3-propanoic acid, 2-[(1,2-dihydro-2-oxo-3H-indol-3-ylidene)methyl]-4-methyl-[CAS]), SC-77964, PNU-171829, CGS-27023A, N-hydroxy-2(R)-[(4-methoxybenzene-sulfonyl)(4-picolyl)amino]-2-(2-tetrahydrofuranyl)-acetamide, L-758354 ((1,1'-Biphenyl)-4-hexanoic acid, Alpha-butyl-Gamma-(((2,2-dimethyl-1-((methylamino)carbonyl)propyl)amino)carbonyl)-4'-fluoro-, (AlphaS-(AlphaR*,GammaS*(R*)))-[CAS]), GI-155704A, CPA-926 or an analogue or derivative thereof. Additional representative examples are included in U.S. Pat. Nos. 5,665,777; 5,985,911; 6,288,261; 5,952,320; 6,441,189; 6,235,786; 6,294,573; 6,294,539; 6,563,002; 6,071,903; 6,358,980; 5,852,213; 6,124,502; 6,160,132; 6,197,791; 6,172,057; 6,288,086; 6,342,508; 6,228,869; 5,977,408; 5,929,097; 6,498,167; 6,534,491; 6,548,524; 5,962,481; 6,197,795; 6,162,814; 6,441,023; 6,444,704; 6,462,073; 6,162,821; 6,444,639; 6,262,080; 6,486,193; 6,329,550; 6,544,980; 6,352,976; 5,968,795; 5,789,434; 5,932,763; 6,500,847; 5,925,637; 6,225,314; 5,804,581; 5,863,915; 5,859,047; 5,861,428; 5,886,043; 6,288,063; 5,939,583; 6,166,082; 5,874,473; 5,886,022; 5,932,577; 5,854,277; 5,886,024; 6,495,565; 6,495,548; 6,479,502; 5,696,082; 5,700,838; 6,444,639; 6,262,080; 6,486,193; 6,329,550; 6,544,980; 6,352,976; 5,968,795; 5,789,434; 5,932,763; 6,500,847; 5,925,637; 6,225,314; 5,804,581; 5,863,915; 5,859,047; 5,861,428; 5,886,043; 6,288,063; 5,939,583; 6,166,082; 5,874,473; 5,886,022; 5,932,577; 5,854,277; 5,886,024; 6,495,565; 6,642,255; 6,495,548; 6,479,502; 5,696,082; 5,700,838; 5,861,436; 5,691,382; 5,763,621; 5,866,717; 5,902,791; 5,962,529; 6,017,889; 6,022,873; 6,022,898; 6,103,739; 6,127,427; 6,258,851; 6,310,084; 6,358,987; 5,872,152; 5,917,090; 6,124,329; 6,329,373; 6,344,457; 5,698,706; 5,872,146; 5,853,623; 6,624,144; 6,462,042; 5,981,491; 5,955,435; 6,090,840; 6,114,372; 6,566,384; 5,994,293; 6,063,786; 6,469,020; 6,118,001; 6,187,924; 6,310,088; 5,994,312; 6,180,611; 6,110,896; 6,380,253; 5,455,262; 5,470,834; 6,147,114; 6,333,324; 6,489,324; 6,362,183; 6,372,758; 6,448,250; 6,492,367; 6,380,258; 6,583,299; 5,239,078; 5,892,112; 5,773,438; 5,696,147; 6,066,662; 6,600,057; 5,990,158; 5,731,293; 6,277,876; 6,521,606; 6,168,807; 6,506,414; 6,620,813; 5,684,152; 6,451,791; 6,476,027; 6,013,649; 6,503,892; 6,420,427; 6,300,514; 6,403,644; 6,177,466; 6,569,899; 5,594,006; 6,417,229; 5,861,510; 6,156,798; 6,387,931; 6,350,907; 6,090,852; 6,458,822; 6,509,337; 6,147,061; 6,114,568; 6,118,016; 5,804,593; 5,847,153; 5,859,061; 6,194,451; 6,482,827; 6,638,952; 5,677,282; 6,365,630; 6,130,254; 6,455,569; 6,057,369; 6,576,628; 6,110,924; 6,472,396; 6,548,667; 5,618,844; 6,495,578; 6,627,411; 5,514,716; 5,256,657; 5,773,428; 6,037,472; 6,579,890; 5,932,595; 6,013,792; 6,420,415; 5,532,265; 5,691,381; 5,639,746; 5,672,598; 5,830,915; 6,630,516; 5,324,634; 6,277,061; 6,140,099; 6,455,570; 5,595,885; 6,093,398; 6,379,667; 5,641,636; 5,698,404; 6,448,058; 6,008,220; 6,265,432; 6,169,103; 6,133,304; 6,541,521; 6,624,196; 6,307,089; 6,239,288; 5,756,545; 6,020,366; 6,117,869; 6,294,674; 6,037,361; 6,399,612; 6,495,568; 6,624,177; 5,948,780; 6,620,835; 6,284,513; 5,977,141; 6,153,612; 6,297,247; 6,559,142; 6,555,535; 6,350,885; 5,627,206; 5,665,764; 5,958,972; 6,420,408; 6,492,422; 6,340,709; 6,022,948; 6,274,703; 6,294,694; 6,531,499; 6,465,508; 6,437,177; 6,376,665; 5,268,384; 5,183,900; 5,189,178; 6,511,993; 6,617,354; 6,331,563; 5,962,466; 5,861,427; 5,830,869; and 6,087,359.

23. NF Kappa B Inhibitors

In another embodiment, the pharmacologically active compound is a NF kappa B inhibitor (e.g., Celgene (SP100030, SP100207, SP100393), AVE-0545, Oxi-104 (Benzamide, 4-amino-3-chloro-N-(2-(diethylamino)ethyl)-[CAS]), dexlipotam, INDRA, R-flurbiprofen ([1,1'-Biphenyl]-4-acetic acid, 2-fluoro-Alpha-methyl), SP100030 (2-chloro-N-[3,5-di(trifluoromethyl)phenyl]-4-(trifluoromethyl)pyrimidine-5-carboxamide), AVE-0545, VIATRIS, AVE-0547, Bay 11-7082, Bay 11-7085, 15 deoxy-prostaylandin J2, bortezomib (Boronic acid, [(1R)-3-methyl-1-[[(2S)-1-oxo-3-phenyl-2-[(pyrazinylcarbonyl)amino]propyl]amino]butyl]-[CAS]) or an analogue or derivative thereof.

24. NO Agonists

In another embodiment, the pharmacologically active compound is a NO antagonist (e.g., NCX-4016 (Benzoic acid, 2-(acetyloxy)-, 3-((nitrooxy)methyl)phenyl ester [CAS]), NCX-2216, L-arginine or an analogue or derivative thereof.

25. P38 MAP Kinase Inhibitors

In another embodiment, the pharmacologically active compound is a P38 MAP kinase inhibitor (e.g., VX-745 (Vertex Pharmaceuticals, Inc., Cambridge, Mass.), GW-2286, SK86002, CGP-52411, BIRB-798, SB220025, RO-320-1195, RWJ-67657, RWJ-68354, SCIO-469, SCIO-323, AMG-548, CMC-146, SD-31145, CC-8866, Ro-320-1195, Roche (3853, 4507, 6145, 8464, 0945, 6257, 3391, 3470, 1151634, 5274, 5161, 4194, 1195), BIX 983 (Boehringer Ingelheim), PD-98059 (4H-1-Benzopyran-4-one, 2-(2-amino-3-methoxyphenyl)-[CAS]), CGH-2466, doramapimod, SB-203580 (Pyridine, 4-[5-(4-fluorophenyl)-2-[4-(methylsulfinyl)phenyl]-1H-imidazol-4-yl]-[CAS]), SB-220025 ((5-(2-Amino-4-pyrimidinyl)-4-(4-fluorophenyl)-1-(4-piperidinyl)imidazole)), SB-281832, PD169316, SB202190 or an analogue or derivative thereof. Additional representative examples are included in U.S. Pat. Nos. 6,300,347; 6,316,464; 6,316,466; 6,376,527; 6,444,696; 6,479,507; 6,509,361; 6,579,874; and 6,630,485, U.S. Publication Nos. 2001/0044538A1; 2002/0013354A1; 2002/0049220A1; 2002/0103245A1; 2002/0151491A1; 2002/0156114A1; 2003/0018051A1; 2003/0073832A1; 2003/0130257A1; 2003/0130273A1; 2003/0130319A1; 2003/0139388A1; 2003/0139462A1; 2003/0149031A1; 2003/0166647A1; and 2003/0181411A1; and PCT Publication Nos. WO 00/63204A2, WO 01/21591A1, WO 01/35959A1, WO 01/74811A2, WO 02/18379A2, WO 02/064594A2, WO 02/083622A2, WO 02/094842A2, WO 02/096426A1, WO 02/101015A2, WO 02/103000A2, WO 03/008413A1, WO 03/016248A2, WO 03/020715A1, WO 03/024899A2, WO 03/031431A1, WO 03/040103A1, WO 03/053940A1, WO 03/053941A2, WO 03/063799A2, WO 03/079986A2, WO 03/080024A2, WO 03/082287A1, WO 97/44467A1, WO 99/01449A1, and WO 99/58523A1.

26. Phosphodiesterase Inhibitors

In another embodiment, the pharmacologically active compound is a phosphodiesterase inhibitor (e.g., CDP-840 (Pyridine, 4-[(2R)-2-[3-(cyclopentyloxy)-4-methoxyphenyl]-2-phenylethyl]-[CAS]), CH-3697, CT-2820, D-22888 (Imidazo[1,5-a]pyrido[3,2-e]pyrazin-6(5H)-one, 9-ethyl-2-methoxy-7-methyl-5-propyl-[CAS]), D-4418 (8-Methoxyquinoline-5-[N-(2,5-dichloropyridin-3-yl)]carboxamide), 1-(3-cyclopentyloxy-4-methoxyphenyl)-2-(2,6-dichloro-4-pyridyl)ethanone oxime, D-4396, ONO-6126, CDC-998, CDC-801, V-11294A (3-[3-(Cyclopentyloxy)-4-methoxybenzyl]-6-(ethylamino)-8-isopropyl-3H-purine hydrochloride), S,S'-methylene-bis(2-(8-cyclopropyl-3-propyl-6-(4-pyridylmethylamino)-2-thio-3H-purine))tetrahyrochloride, Rolipram (2-Pyrrolidinone, 4-[3-(cyclopentyloxy)-4-methoxyphenyl]-[CAS]), CP-293121, CP-353164 (5-(3-Cyclopentyloxy-4-methoxyphenyl)pyridine-2-carboxamide), oxagrelate (6-Phthalazinecarboxylic acid, 3,4-dihydro-1-(hydroxymethyl)-5,7-dimethyl-4-oxo-, ethyl ester [CAS]), PD-168787, ibudilast (1-Propanone, 2-methyl-1-[2-(1-methylethyl)pyrazolo[1,5-a]pyridin-3-yl]-[CAS]), oxagrelate (6-Phthalazinecarboxylic acid, 3,4-dihydro-1-(hydroxymethyl)-5,7-dimethyl-4-oxo-, ethyl ester [CAS]), griseolic acid (Alpha-L-talo-Oct-4-enofuranuronic acid, 1-(6-amino-9H-purin-9-yl)-3,6-anhydro-6-C-carboxy-1,5-dideoxy-[CAS]), KW-4490, KS-506, T-440, roflumilast (Benzamide, 3-(cyclopropylmethoxy)-N-(3,5-dichloro-4-pyridinyl)-4-(difluoromethoxy)-[CAS]), rolipram, milrinone, triflusinal (Benzoic acid, 2-(acetyloxy)-4-(trifluoromethyl)-[CAS]), anagrelide hydrochloride (Imidazo[2,1-b]quinazolin-2(3H)-one, 6,7-dichloro-1,5-dihydro-, monohydrochloride [CAS]), cilostazol (2(1H)-Quinolinone, 6-[4-(1-cyclohexyl-1H-tetrazol-5-yl)butoxy]-3,4-dihydro-[CAS]), propentofylline (1H-Purine-2,6-dione, 3,7-dihydro-3-methyl-1-(5-oxohexyl)-7-propyl-[CAS]), sildenafil citrate (piperazine, 1-((3-(4,7-dihydro-1-methyl-7-oxo-3-propyl-1H-pyrazolo(4,3-d) pyrimidin-5-yl)-4-ethoxyphenyl)sulfonyl)-4-methyl, 2-hydroxy-1,2,3-propanetricarboxylate-(1:1) [CAS]), tadalafil (Pyrazino(1',':1,6)pyrido(3,4-b)indole-1,4-dione, 6-(1,3-benzodioxol-5-yl)-2,3,6,7,12,12a-hexahydro-2-methyl-, (6R-trans) [CAS]), vardenafil (piperazine, 1-(3-(1,4-dihydro-5-methyl-(4-oxo-7-propylimidazo(5,1-f)(1,2,4)-triazin-2-yl)-4-ethoxyphenyl)sulfonyl)-4-ethyl-[CAS]), milrinone ([3, 4'-Bipyridine]-5-carbonitrile, 1,6-dihydro-2-methyl-6-oxo-[CAS]), enoximone (2H-Imidazol-2-one, 1,3-dihydro-4-methyl-5-[4-(methylthio)benzoyl]-[CAS]), theophylline (1H-Purine-2,6-dione, 3,7-dihydro-1,3-dimethyl-[CAS]), ibudilast (1-Propanone, 2-methyl-1-[2-(1-methylethyl)pyrazolo[1,5-a]pyridin-3-yl]-[CAS]), aminophylline (1H-Purine-2,6-dione, 3,7-dihydro-1,3-dimethyl-, compd. with 1,2-ethanediamine (2:1)-[CAS]), acebrophylline (7H-Purine-7-acetic acid, 1,2,3,6-tetrahydro-1,3-dimethyl-2,6-dioxo-, compd. with trans-4-[[(2-amino-3,5-dibromophenyl)methyl] amino]cyclohexanol (1:1) [CAS]), plafibride (Propanamide, 2-(4-chlorophenoxy)-2-methyl-N-[[(4-morpholinylmethyl) amino]carbonyl]-[CAS]), loprinone hydrochloride (3-Pyridinecarbonitrile, 1,2-dihydro-5-imidazo[1,2-a]pyridin-6-yl-6-methyl-2-oxo-, monohydrochloride-[CAS]), fosfosal (Benzoic acid, 2-(phosphonooxy)-[CAS]), aminone ([3,4'-Bipyridin]-6(1H)-one, 5-amino-[CAS]) or an analogue or derivative thereof.

27. TGF Beta Inhibitors

In another embodiment, the pharmacologically active compound is a TGF beta Inhibitor (e.g., mannose-6-phosphate, LF-984, tamoxifen (Ethanamine, 2-[4-(1,2-diphenyl-1-butenyl)phenoxy]-N,N-dimethyl-, (Z)-[CAS]), tranilast or an analogue or derivative thereof.

28. Thromboxane A2 Antagonists

In another embodiment, the pharmacologically active compound is a thromboxane A2 antagonist (e.g., CGS-22652 (3-Pyridineheptanoic acid, .gamma.-[4-[[(4-chlorophenyl) sulfonyl]amino]butyl]-, (.+-.)-[CAS]), ozagrel (2-Propenoic acid, 3-[4-(1H-imidazol-1-ylmethyl)phenyl]-, (E)-[CAS]), argatroban (2-Piperidinecarboxylic acid, 1-[5-[(aminoiminomethyl)amino]-1-oxo-2-[[(1,2,3,4-tetrahydro-3-methyl-8-quinolinyl)sulfonyl]amino]pentyl]-4-methyl-[CAS]), ramatroban (9H-Carbazole-9-propanoic acid, 3-[[(4-fluorophenyl)sulfonyl]amino]-1,2,3,4-tetrahydro-, (R)-[CAS]), torasemide (3-Pyridinesulfonamide, N-[[(1-methylethyl) amino]carbonyl]-4-[(3-methylphenyl)amino]-[CAS]), gamma linoleic acid ((Z,Z,Z)-6,9,12-Octadecatrienoic acid [CAS]), seratrodast (Benzeneheptanoic acid, zeta-(2,4,5-trimethyl-3,6-dioxo-1,4-cyclohexadien-1-yl)-, (+/-)-[CAS]) or an analogue or derivative thereof.

29. TNFa Antagonists/TACE Inhibitors

In another embodiment, the pharmacologically active compound is a TNFa Antagonist/TACE Inhibitor (e.g., Celgene (CC10037, CC-11049, CC-10004, CC10083), E-5531 (2-Deoxy-6-0-[2-deoxy-3-0-[3(R)-[5(Z)-dodecenoyloxy]-decyl]-6-O-methyl-2-(3-oxotetradecanamido)-4-O-phosphono-β-D-glucopyranosyl]-3-0-[3(R)-hydroxydecyl]-2-(3-oxotetradecanamido)-Alpha-D-glucopyranose-1-O-phosphate), AZD-4717, glycophosphopeptical, UR-12715 (Benzoic acid, 2-hydroxy-5-[[4-[3-[4-(2-methyl-1H-imidazol[4,5-c]pyridin-1-yl]methyl]-1-piperidinyl]-3-oxo-1-phenyl-1-propenyl]phenyl]azo] (Z) [CAS]), PMS-601, AM-87, xyloadenosine (9H-Purin-6-amine, 9-β-D-xylofuranosyl-[CAS]), RDP-58, RDP-59, BB2275, benzydamine, E-3330 (Undecanoic acid, 2-[(4,5-dimethoxy-2-methyl-3,6-dioxo-1, 4-cyclohexadien-1-yl)methylene]-, (E)-[CAS]), N-[D,L-2-(hydroxyaminocarbonyl)methyl-4-methylpentanoyl]-L-3-(2'-naphthyl)alanyl-L-alanine, 2-aminoethyl amide, CP-564959, MLN-608, SPC-839, ENMD-0997, Sch-23863 ((2-[10,11-Dihydro-5-ethoxy-5H-dibenzo[a,d]cyclohepten- 5-yl]-N,N-dimethyl-ethanamine), SH-636, PKF-241-466, PKF-242-484, TNF-484A, cilomilast (Cis-4-cyano-4-[3-(cyclopentyloxy)-4-methoxyphenyl]cyclohexane-1-carboxylic acid), GW-3333, GW-4459, BMS-561392, AM-87, cloricromene (Acetic acid, [[8-chloro-3-[2-(diethylamino)ethyl]-4-methyl-2-oxo-2H-1-benzopyran-7-yl]oxy]-, ethyl ester [CAS]), thalidomide (1H-Isoindole-1,3(2H)-dione, 2-(2,6-dioxo-3-piperidinyl)-[CAS]), vesnarinone (piperazine, dimethoxybenzoyl)-4-(1,2,3,4-tetrahydro-2-oxo-6-quinolinyl)-[CAS]), infliximab, lentinan, etanercept (1-235-Tumor necrosis factor receptor (human) fusion protein with 236-467-immunoglobulin G1 (human gamma1-chain Fc fragment) [CAS]), diacerein (2-Anthracenecarboxylic acid, 4,5-bis(acetyloxy)-9,10-dihydro-9,10-dioxo-[CAS]) or an analogue or derivative thereof.

30. Tyrosine Kinase Inhibitors

In another embodiment, the pharmacologically active compound is a tyrosine kinase inhibitor (e.g., SKI-606, ER-068224, SD-208, N-(6-Benzothiazolyl)-4-(2-(1-piperazinyl)pyrid-5-yl)-2-pyrimidineamine, celastrol (24,25,26-Trinoroleana-1(10),3,5,7-tetraen-29-oic acid, 3-hydroxy-9,13-dimethyl-2-oxo-, (9.beta., 13Alpha,14β,20Alpha)-[CAS]), CP-127374 (Geldanamycin, 17-demethoxy-17-(2-propenylamino)-[CAS]), CP-564959, PD-171026, CGP-52411 (1H-Isoindole-1,3(2H)-dione, 4,5-bis(phenylamino)-[CAS]), CGP-53716 (Benzamide, N-[4-methyl-3-[[4-(3-pyridinyl)-2-pyrimidinyl]amino]phenyl]-[CAS]), imatinib (4-((Methyl-1-piperazinyl)methyl)-N-[4-methyl-3-[[4-(3-pyridinyl)-2-pyrimidinyl]amino]-phenyl]benzamide methanesulfonate), NVP-AAK980-NX, KF-250706 (13-Chloro,5(R),6(S)-epoxy-14,16-dihydroxy-11-(hydroyimino)-3(R)-methyl-3,4,5,6,11,12-hexahydro-1H-2-benzoxacyclotetradecin-1-one), 5-[3-[3-methoxy-4-[2-[(E)-2-phenylethenyl]-4-oxazolylmethoxy]phenyl]propyl]-3-[2-[(E)-2-phenylethenyl]-4-oxazolylmethyl]-2,4-oxazolidinedione, genistein or an analogue or derivative thereof.

31. Vitronectin Inhibitors

In another embodiment, the pharmacologically active compound is a vitronectin inhibitor (e.g., O-[9,10-dimethoxy-1,2,3,4,5,6-hexahydro-4-[(1,4,5,6-tetrahydro-2-pyrimidinyl)hydrazono]-8-benz(e)azulenyl]-N-[(phenylmethoxy)carbonyl]-DL-homoserine 2,3-dihydroxypropyl ester, (2S)-Benzoylcarbonylamino-3-[2-((4S)-(3-(4,5-dihydro-1H-imidazol-2-ylamino)-propyl)-2,5-dioxo-imidazolidin-1-ylyacetylamino]-propionate, Sch-221153, S-836, SC-68448 (1'-[[2-2-[[[3-[(aminoiminomethyl)amino]-phenyl]carbonyl]amino]acetyl]amino]-3,5-dichlorobenzenepropanoic acid), SD-7784, S-247 or an analogue or derivative thereof.

32. Fibroblast Growth Factor Inhibitors

In another embodiment, the pharmacologically active compound is a fibroblast growth factor inhibitor (e.g., CT-052923 ([(2H-benzo[d]1,3-dioxalan-5-methyl)amino][4-(6,7-dimethoxyquinazolin-4-yl)piperazinyl]methane-1-thione) or an analogue or derivative thereof.

33. Protein Kinase Inhibitors

In another embodiment, the pharmacologically active compound is a protein kinase inhibitor (e.g., KP-0201448, NPC15437 (Hexanamide, 2,6-diamino-N-[[1-(1-oxotridecyl)-2-piperidinyl]methyl]-[CAS]), fasudil (1H-1,4-Diazepine, hexahydro-1-(5-isoquinolinylsulfonyl)-[CAS]), midostaurin (Benzamide, N-(2,3,10,11,12,13-hexahydro-10-methoxy-9-methyl-1-oxo-9,13-epoxy-1H,9H-diindolo[1,2,3-gh:3',2',1'-Im]pyrrolo[3,4-j][1,7]benzodiazonin-11-yl)-N-methyl-, (9Alpha,1011,11β,13Alpha)-[CAS]),fasudil (1H-1,4-Diazepine, hexahydro-1-(5-isoquinolinylsulfonyl)-[CAS]) or an analogue or derivative thereof.

34. PDGF Receptor Kinase Inhibitors

In another embodiment, the pharmacologically active compound is a PDGF receptor kinase inhibitor (e.g., RPR-127963E or an analogue or derivative thereof.

35. Endothelial Growth Factor Receptor Kinase Inhibitors

In another embodiment, the pharmacologically active compound is an endothelial growth factor receptor kinase inhibitor (e.g., CEP-7055, SU-0879 ((E)-3-(3,5-di-tert-Butyl-4-hydroxyphenyl)-2-(aminothiocarbonyl)acrylonitrile), BIBF-1000 or an analogue or derivative thereof.

36. Retinoic Acid Receptor Antagonists

In another embodiment, the pharmacologically active compound is a retinoic acid receptor antagonist (e.g., etarotene (Ro-15-1570) (Naphthalene, 6-[2-[4-(ethylsulfonyl)phenyl]-1-methylethenyl]-1,2,3,4-tetrahydro-1,1,4,4-tetramethyl-, (E)-[CAS]), (2E,4E)-3-Methyl-5-(2-((E)-2-(2,6,6-trimethyl-1-cyclohexen-1-yl)ethenyl)-1-cyclohexen-1-yl)-2,4-pentadienoic acid, tocoretinate (Retinoic acid, 3,4-dihydro-2,5,7,8-tetramethyl-2-(4,8,12-trimethyltridecyl)-2H-1-benzopyran-6-yl ester, [2R*(4R*,8R*)]-(±)-[CAS]), aliretinoin (Retinoic acid, cis-9, trans-13-[CAS]), bexarotene (Benzoic acid, 4-(1-(5,6,7,8-tetrahydro-3,5,5,8,8-pentamethyl-2-naphthalenyl)ethenyl)-[CAS]) or an analogue or derivative thereof.

37. Platelet Derived Growth Factor Receptor Kinase Inhibitors

In another embodiment, the pharmacologically active compound is a platelet derived growth factor receptor kinase inhibitor (e.g., leflunomide (4-Isoxazolecarboxamide, 5-methyl-N-[4-(trifluoromethyl)phenyl]-[CAS]) or an analogue or derivative thereof.

38. Fibrinogin Antagonists

In another embodiment, the pharmacologically active compound is a fibrinogin antagonist (e.g., picotamide (1,3-Benzenedicarboxamide, 4-methoxy-N,N'-bis(3-pyridinylmethyl)-[CAS]) or an analogue or derivative thereof.

39. Antimycotic Agents

In another embodiment, the pharmacologically active compound is an antimycotic agent (e.g., miconazole, sulconizole, parthenolide, rosconitine, nystatin, isoconazole, fluconazole, ketoconasole, imidazole, itraconazole, terpinafine, elonazole, bifonazole, clotrimazole, conazole, terconazole (piperazine, 1-[4-[[2-(2,4-dichlorophenyl)-2-(1H-1,2,4-triazol-1-ylmethyl)-1,3-dioxolan-4-yl]methoxy]phenyl]-4-(1-methylethyl)-, cis-[CAS]), isoconazole (1-[2-(2-6-dichlorobenzyloxy)-2-(2-,4-dichlorophenyl)ethyl]), griseofulvin (Spiro[benzofuran-2(3H), 1'-[2]cyclohexane]-3,4'-dione, 7-chloro-2',4,6-trimeth-oxy-6' methyl-, (1'S-trans)-[CAS]), bifonazole (1H-Imidazole, 1-([1,1'-biphenyl]-4-ylphenylmethyl)-[CAS]), econazole nitrate (1-[2-[(4-chlorophenyl)methoxy]-2-(2,4-dichlorophenyl)ethyl]-1H-imidazole nitrate), croconazole (1H-Imidazole, 1-[1-[2-[(3-chlorophenyl)methoxy]phenyl]ethenyl]-[CAS]), sertaconazole (1H-Imidazole, 1-[2-[(7-chlorobenzo[b]thien-3-yl)methoxy]-2-(2,4-dichlorophenyl)ethyl]-[CAS]), omoconazole (1H-Imidazole, 1-[2-[2-(4-chlorophenoxy)ethoxy]-2-(2,4-dichlorophenyl)-1-methylethenyl]-, (Z)-[CAS]), flutrimazole (1H-Imidazole, 1-[(2-fluorophenyl)(4-fluorophenyl)phenylmethyl]-[CAS]), fluconazole (1H-1,2,4-Triazole-1-ethanol, Alpha-(2,4-difluorophenyl)-Alpha-(1H-1,2,4-triazol-1-ylmethyl)-[CAS]), neticonazole (1H-Imidazole, 1-[2-(methylthio)-1-[2-(pentyloxy)phenyl]ethenyl]-, monohydrochloride, (E)-[CAS]), butoconazole (1H-Imidazole, 1-[4-(4-chlorophenyl)-2-[(2,6-dichlorophenyl)thio]butyl]-, (+/−)-[CAS]), clotrimazole (1-[(2-chlorophenyl)diphenylmethyl]-1H-imidazole) or an analogue or derivative thereof.

40. Bisphosphonates

In another embodiment, the pharmacologically active compound is a bisphosphonate (e.g., clodronate, alendronate, pamidronate, zoledronate, etidronate) or an analogue or derivative thereof.

41. Phospholipase A1 Inhibitors

In another embodiment, the pharmacologically active compound is a phospholipase A1 inhibitor (e.g., loteprednol etabonate (Androsta-1,4-diene-17-carboxylic acid, 17-[(ethoxycarbonyl)oxy]-11-hydroxy-3-oxo-, chloromethyl ester, (11β,17Alpha)-[CAS] or an analogue or derivative thereof.

42. Histamine H1/H2/H3 Receptor Antagonists

In another embodiment, the pharmacologically active compound is a histamine H1/H2/H3 receptor antagonist (e.g., ranitidine (1,1-Ethenediamine, N-[2-[[[5-[(dimethylamino) methyl]-2-furanyl]methyl]thio]ethyl]-N'-methyl-2-nitro-[CAS]), niperotidine (N-[2-[[5-[(dimethylamino)methyl] furfuryl]thio]ethyl]-2-nitro-N'-piperonyl-1,1-ethenediamine), famotidine (Propanimidamide, 3-[[[2-[(aminoiminomethyl)amino]-4-thiazolyl]methyl]thio]-N-(aminosulfonyl)-[CAS]), roxitadine acetate HCl (Acetamide, 2-(acetyloxy)-N-[3-[3-(1-piperidinylmethyl)phenoxy]propyl]-, monohydrochloride [CAS]), lafutidine (Acetamide, 2-[(2-furanylmethyl)sulfinyl]-N-[4-[[4-(1-piperidinylmethyl)-2-pyridinyl]oxy]-2-butenyl]-, (Z)-[CAS]), nizatadine (1,1-Ethenediamine, N-[2-[[[2-[(dimethylamino)methyl]-4-thiazolyl]methyl]thio]ethyl]-N'-methyl-2-nitro-[CAS]), ebrotidine (Benzenesulfonamide, N-[[[2-[[[2-[(aminoiminomethyl)amino]-4-thiazoly]methyl]thio]ethyl]amino]methylene]-4-bromo-[CAS]), rupatadine (5H-Benzo[5,6]cyclohepta[1,2-b]pyridine, 8-chloro-6,11-dihydro-11-[1-[(5-methyl-3-pyridinyl)methyl]-4-piperidinylidene]-, trihydrochloride-[CAS]), fexofenadine HCl (Benzeneacetic acid, 4-[1-hydroxy-4-[4(hydroxydiphenylmethyl)-1-piperidinyl]butyl]-Alpha,Alpha-dimethyl-, hydrochloride [CAS]) or an analogue or derivative thereof.

43. Macrolide Antibiotics

In another embodiment, the pharmacologically active compound is a macrolide antibiotic (e.g., dirithromycin (Erythromycin, 9-deoxo-11-deoxy-9,11-[imino[2-(2-methoxyethoxy)ethylidene]oxy]-, [9S(R)]-[CAS]), flurithromycin ethylsuccinate (Erythromycin, 8-fluoro-mono(ethyl butanedioate) (ester)-[CAS]), erythromycin stinoprate (Erythromycin, 2'-propanoate, compd. with N-acetyl-L-cysteine (1:1) [CAS]), clarithromycin (Erythromycin, 6-O-methyl-[CAS]), azithromycin (9-deoxo-9a-aza-9a-methyl-9a-homoerythromycin-A), telithromycin (3-De((2,6-dideoxy-3-C-methyl-3-O-methyl-Alpha-L-ribo-hexopyranosyl)oxy)-11,12-dideoxy-6-O-methyl-3-oxo-12,11-(oxycarbonyl((4-(4-(3-pyridinyl)-1H-imidazol-1-yl)butyl)imino))-[CAS]), roxithromycin (Erythromycin, 9-[0-[(2-methoxyethoxy)methyl]oxime] [CAS]), rokitamycin (Leucomycin V, 4B-butanoate 3B-propanoate [CAS]), RV-11 (erythromycin monopropionate mercaptosuccinate), midecamycin acetate (Leucomycin V, 3B,9-diacetate 3,4B-dipropanoate [CAS]), midecamycin (Leucomycin V, 3,4B-dipropanoate [CAS]), josamycin (Leucomycin V, 3-acetate 4B-(3-methylbutanoate) [CAS]) or an analogue or derivative thereof.

44. GPIIb IIIa Receptor Antagonists

In another embodiment, the pharmacologically active compound is an GPIIb IIIa receptor antagonist (e.g., tirofiban hydrochloride (L-Tyrosine, N-(butylsulfonyl)-0-[4-(4-piperidinyl)butyl]-, monohydrochloride-[CAS]), eptifibatide (L-Cysteinamide, N6-(aminoiminomethyl)-N2-(3-mercapto-1-oxopropyl)-L-lysylglycyl-L-Alpha-aspartyl-L-tryptophyl-L-prolyl-, cyclic(1→6)-disulfide [CAS]) or an analogue or derivative thereof.

45. Endothelin Receptor Antagonists

In another embodiment, the pharmacologically active compound is an endothelin receptor antagonist (e.g., bosentan (Benzenesulfonamide, dimethylethyl)-N-[6-(2-hydroxyethoxy)-5-(2-methoxyphenoxy)[2,2'-bipyrimidin]-4-yl]-[CAS]) or an analogue or derivative thereof.

46. Peroxisome Proliferator-Activated Receptor Agonists

In another embodiment, the pharmacologically active compound is a peroxisome proliferators-activated receptor agonist (e.g., gemfibrozil (Pentanoic acid, 5-(2,5-dimethylphenoxy)-2,2-dimethyl-[CAS]), fenofibrate (Propanoic acid, 2-[4-(4-chlorobenzoyl)phenoxy]-2-methyl-, 1-methylethyl ester [CAS]), ciprofibrate (Propanoic acid, 2-[4-(2,2-dichlorocyclopropyl)phenoxy]-2-methyl-[CAS]), rosiglitazone maleate (2,4-Thiazolidinedione, 5-((4-(2-(methyl-2-pyridinylamino)ethoxy)phenyl)methyl)-, (Z)-2-butenedioate (1:1) [CAS]), pioglitazone hydrochloride (2,4-Thiazolidinedione, 5-[[4-[2-(5-ethyl-2-pyridinyl)ethoxy]phenyl] methyl]-, monohydrochloride (+/−)-[CAS]), etofylline clofibrate (Propanoic acid, 2-(4-chlorophenoxy)-2-methyl-, 2-(1,2,3,6-tetrahydro-1,3-dimethyl-2,6-dioxo-7H-purin-7-yl) ethyl ester [CAS]), etofibrate (3-Pyridinecarboxylic acid, 2-[2-(4-chlorophenoxy)-2-methyl-1-oxopropoxy]ethyl ester [CAS]), clinofibrate (Butanoic acid, 2,2'-[cyclohexylidenebis (4,1-phenyleneoxy)]bis[2-methyl-][CAS]), bezafibrate (Propanoic acid, 2-[4-[2-[(4-chlorobenzoyl)amino]ethyl]phenoxy]-2-methyl-[CAS]), binifibrate (3-Pyridinecarboxylic acid, 2-[2-(4-chlorophenoxy)-2-methyl-1-oxopropoxy]-1,3-propanediyl ester [CAS]) or an analogue or derivative thereof.

47. Estrogen Receptor Agents

In another embodiment, the pharmacologically active compound is an estrogen receptor agent (e.g., estradiol, 17-β-estradiol) or an analogue or derivative thereof.

48. Somatostatin Analogues

In another embodiment, the pharmacologically active compound is somatostatin or a somatostatin analogue (e.g., angiopeptin, lanretide, octreotide) or an analogue or derivative thereof.

49. JNK (Jun Kinase) Inhibitors

In another embodiment, the pharmacologically active compound is a JNK Kinase inhibitor (e.g., Celgene (SP600125, SPC105, SPC23105), AS-602801 (Serono)) or an analogue or derivative thereof.

50. Melanocortin Analogues

In another embodiment, the pharmacologically active compound is a melanocortin analogue (e.g., HP228) or an analogue or derivative thereof.

51. RAF Kinase Inhibitors

In yet another embodiment, the pharmacologically active compound is a raf kinase inhibitor (e.g., BAY-43-9006 (N-(4-chloro-3-(trifluoromethyl)phenyl-N'-(4-(2-(N-methylcarbamoyl)-4-pyridyloxy)phenyl)urea) or analogue or derivative thereof.

52. Lysylhydroxylase Inhibitors

In another embodiment, the pharmacologically active compound is a lysylhydroxylase inhibitor (e.g., minoxidil), or an analogue or derivative thereof.

53. IKK 1/2 Inhibitors

In another embodiment, the pharmacologically active compound is an IKK 1/2 inhibitor (e.g., BMS-345541, SPC839) or an analogue or derivative thereof.

In addition to incorporation of a fibrosis-inhibiting agent into or onto the formulation, another biologically active agent can be incorporated into or onto the formulation, for example an anti-inflammatory (e.g., dexamethazone or asprin), anti-thrombotic agents (e.g., heparin, heparin complexes, hydrophobic heparin derivatives, aspirin or dipyridamole), and/or an antibiotic (e.g., amoxicillin, trimethoprim-sulfamethoxazole, azithromycin, clarithromycin, amoxicillin-clavulanate, cefprozil, cefuroxime, cefpodoxime, or cefdinir).

In one aspect of the invention the pharmacologically active compound is capable of altering cellular and/or non-cellular processes involved in the development and/or maintenance of one or more processes involved in fibrosis or adhesions between tissues or between tissues and a medical device. Fibrosis inducing compositions may be useful, for example, as tissue sealants, for effecting tissue adhesion, and for tissue augmentation and repair. Thus, pharmacological agents within the scope of this invention include but are not limited to those which increase one or a combination of processes such as cell division, cell secretion, cell migration, cell adhesion, extracellular matrix production, cytokine (e.g., TNF alpha, IL-1, or IL-6), or other inflammatory activator (e.g., chemokines (e.g., MCP-1, IL-8)) production and/or release, angiogenesis, and/or free radical formation and/or release.

Suitable fibrosis-inducing agents may be readily determined based upon the in vitro and in vivo (animal) models such as those provided in Examples 34-36.

Numerous therapeutic compounds have been identified that are of utility in the invention.

In one aspect, the fibrosis or adhesion-inducing agent is silk. Silk refers to a fibrous protein, and may be obtained from a number of sources, typically spiders and silkworms. Typical silks contain about 75% of actual fiber, referred to as fibroin, and about 25% sericin, which is a gummy protein that holds the filaments together. Silk filaments are generally very fine and long—as much as 300-900 meters long. There are several species of domesticated silkworm that are used in commercial silk production, however, *Bombyx mori* is the most common, and most silk comes from this source. Other suitable silkworms include *Philosamia cynthia ricini, Antheraea yamamai, Antheraea pernyi*, and *Antheraea mylitta*. Spider silk is relatively more difficult to obtain, however, recombinant techniques hold promise as a means to obtain spider silk at economical prices (see, e.g., U.S. Pat. Nos. 6,268,169; 5,994,099; 5,989,894; and 5,728,810, which are exemplary only). Biotechnology has allowed researchers to develop other sources for silk production, including animals (e.g., goats) and vegetables (e.g., potatoes). Silk from any of these sources may be used in the present invention.

A commercially available silk protein is available from Croda, Inc., of Parsippany, N.J., and is sold under the trade names CROSILK LIQUID (silk amino acids), CROSILK 10,000 (hydrolyzed silk), CROSILK POWDER (powdered silk), and CROSILKQUAT (cocodiammonium hydroxypropyl silk amino acid). Another example of a commercially available silk protein is SERICIN, available from Pentapharm, LTD, a division of Kordia, BV, of the Netherlands. Further details of such silk protein mixtures can be found in U.S. Pat. No. 4,906,460, to Kim, et al., assigned to Sorenco. Silk useful in the present invention includes natural (raw) silk, hydrolyzed silk, and modified silk, i.e., silk that has undergone a chemical, mechanical, or vapor treatment, e.g., acid treatment or acylation (see, e.g., U.S. Pat. No. 5,747,015).

Raw silk is typically twisted into a strand sufficiently strong for weaving or knitting. Four different types of silk thread may be produced by this procedure: organzine, crepe, tram and thrown singles. Organzine is a thread made by giving the raw silk a preliminary twist in one direction and then twisting two of these threads together in the opposite direction. Crepe is similar to organzine but is twisted to a much greater extent. Twisting in only one direction two or more raw silk threads makes tram. Thrown singles are individual raw silk threads that are twisted in only one direction. Any of these types of silk threads may be used in the present invention.

The silk used in the present invention may be in any suitable form that allows the silk to be joined with the medical implant, e.g., the silk may be in thread or powder-based forms. Furthermore, the silk may have any molecular weight, where various molecular weights are typically obtained by the hydrolysis of natural silk, where the extent and harshness of the hydrolysis conditions determines the product molecular weight. For example, the silk may have an average (number or weight) molecular weight of 200 to 5,000. See, e.g., JP-B-59-29199 (examined Japanese patent publication) for a description of conditions that may be used to hydrolyze silk.

A discussion of silk may be found in the following documents, which are exemplary only: Hinman, M. B., et al. "Synthetic spider silk: a modular fibre" *Trends in Biotechnology*, 2000, 18(9) 374-379; Vollrath, F. and Knight, D. P. "Liquid crystalline spinning of spider silk" *Nature*, 2001, 410 (6828) 541-548; and Hayashi, C. Y., et al. "Hypotheses that correlate the sequence, structure, and mechanical properties of spider silk proteins" *Int. J. Biol. Macromolecules*, 1999, 24(2-3), 265-270; and U.S. Pat. No. 6,427,933.

Other representative examples of fibrosis and adhesion-inducing agents include irritants (e.g., talc, talcum powder, copper, metallic beryllium (or its oxides), quartz dust, silica, crystalline silicates), polymers (e.g., polylysine, polyurethanes, poly(ethylene terephthalate), PTFE, poly(alkylcyanoactylates), and poly(ethylene-co-vinylacetate)); vinyl chloride and polymers of vinyl chloride; peptides with high lysine content; bleomycin and analogues and derivatives thereof; growth factors and inflammatory cytokines involved in angiogenesis, fibroblast migration, fibroblast proliferation, ECM synthesis and tissue remodeling, such as Epidermal Growth Factor (EGF) Family, Transforming Growth Factor-α (TGF-α), Transforming Growth Factor-β (TGF-9-1, TGF-9-2, TGF-9-3, Platelet-derived Growth Factor (PDGF), Fibroblast Growth Factor (acidic—aFGF; and basic—bFGF), Fibroblast stimulating factor-1, Activins, Vascular Endothelial Growth Factor (including VEGF-2, VEGF-3, VEGF-A, VEGF-B, VEGF-C, Placental Growth Factor —P1GF), Angiopoietins, Insulin-like Growth Factors (IGF), Hepatocyte Growth Factor (HGF), Connective Tissue Growth Factor (CTGF), Myeloid Colony-stimulating Factors (CSFs), Monocyte chemotactic protein, Granulocyte-Macrophage Colony-stimulating Factors (GM-CSF), Granulocyte Colony-stimulating Factor (G-CSF), Macrophage Colony-stimulating Factor (M-CSF), Erythropoietin, Interleukins (particularly IL-1, IL-8, IL-6), Tumor Necrosis Factor-a (TNF9), Nerve Growth Factor (NGF), Interferon-α, Interferon-β, histamine, endothelin-1, angiotensin II, growth hormone (GH), and synthetic peptides, analogues or derivatives of these factors are also suitable for release from specific implants and devices to be described later. Other examples include CTGF (connective tissue growth factor); inflammatory microcrystals (e.g., crystalline minerals such as crystalline silicates); Monocyte chemotactic protein, fibroblast stimulating factor 1, histamine, endothelin-1, angiotensin II, bovine collagen, bromocriptine, methylsergide, methotrexate, chitosan, N-carboxybutyl chitosan, carbon tetrachloride, Thioacetamide, Fibrosin, ethanol, naturally occurring or synthetic peptides containing the Arg-Gly-Asp (RGD) sequence, generally at one or both termini, described, e.g., in U.S. Pat. No. 5,997,895, and tissue adhesives, such as cyanoacrylate and crosslinked poly(ethylene glycol)-methylated collagen compositions, such as CT3 (Cohesion Technolgies, Palo Alto, Calif.). Other examples of fibrosis-inducing agents include bone morphogenic proteins (e.g., BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16). Of these BMP's, BMP-2, BMP-3, BMP-4, BMP-5, BMP-6, and BMP-7 are of particular utility. Bone morphogenic proteins are described, for example, in U.S. Pat. Nos. 4,877,864; 5,013,649; 5,661,007; 5,688,678; 6,177,406; 6,432,919; and 6,534,268 and Wozney, J. M., et al. (1988) Science: 242(4885); 1528-1534.

Other representative examples of fibrosis-inducing agents include components of extracellular matrix (e.g., fibronectin, fibrin, fibrinogen, collagen, including fibrillar and non-fibrillar collagen, adhesive glycoproteins, proteoglycans (e.g., heparin sulphate, chondroitin sulphate, dermatan sulphate), hyaluronan, Secreted Protein Acidic and Rich in Cysteine (SPARC), Thrombospondins, Tenacin, and Cell Adhesion Molecules (including integrins, vitronectin, fibronectin, laminin, hyaluronic acid, elastin, bitronectin), and proteins found in basement membranes, and fibrosin).

Within various embodiments of the invention, a composition which promotes fibrosis (and/or restenosis) also includes a compound which acts to stimulate cellular proliferation. Representative examples of agents that stimulate cellular proliferation include, e.g., dexamethasone, isotretinoin, 17-β-estradiol, diethylstibesterol, cyclosporin A and all-trans retinoic acid (ATRA) and analogues and derivatives thereof. Other examples of agents that stimulate cellular proliferation include: Sphingosine 1-phosphate receptor agonist (e.g., FTY-720 (1,3-Propanediol, 2-amino-2-(2-(4-octylphenyl) ethyl)-,hydrochloride [CAS]; Immunostimulants, such as Imupedone (Methanone, [5-amino-2-(4-methyl-1-piperidinyl)phenyl](4-chlorophenyl)-[CAS]), DiaPep227; and Nerve Growth Factor Agonist, such as, e.g., NG-012 (5H,9H,13H, 21H,25H,-Dibenzo[k,u][1,5,9,15,19]pentaoxacyclotetracosin-5,9,13,21,25-pentone, 7,8,11,12,15,16,23,24,27,28-decahydro-2,4,18,20-tetrahydroxy-1'-(hydroxymethyl)-7, 15,23,27-tetramethyl-[CAS]), NG-121, SS-701 (2,2':6',2"-Terpyridine, 4'-(4-methylphenyl)-, trihydrochloride [CAS]), AMPAIex (Piperidine, 1-(6-quinoxalinylcarbonyl)-[CAS]), RGH-2716 (8-[4,4-bis(4-fluorophenyl)butyl]-3-(1,1-dim-ethylethyl)-4-methylene-1-oxa-3,8-diaza-spiro[4.5]decan-2-one [CAS]), TDN-345 (1-Oxa-3,8-diazaspiro[4.5]decan-2-one, 8-[4,4-bis(4-fluorophenyl)butyl]-3-(1,1-dimethylethyl)-4-methylene-[CAS]).

Within various embodiments of the invention, a stent graft is coated on one aspect with a composition which promotes fibrosis (and/or restenosis), as well as being coated with a composition or compound which prevents thrombosis on another aspect of the device. Representative examples of agents that inhibit thrombosis include heparin, aspirin, dipyridamole, as well as analogues and derivatives thereof.

In another embodiment of the invention, the drug is a hydrophobic drug. The term "hydrophobic drug" refers to drugs that are insoluble or sparingly or poorly soluble in water. As used herein, such drugs will have a solubility below 10 mg/ml, usually below 1 mg/ml, sometimes below 0.01 mg/ml, and sometimes below 0.001 mg/ml. Exemplary hydrophobic drugs include certain steroids, such as budesonide, testosterone, progesterone, estrogen, flunisolide, triamcinolone, beclomethasone, betamethasone; dexamethasone, fluticasone, methylprednisolone, prednisone, hydrocortisone, and the like; certain peptides, such as cyclosporin cyclic peptide, retinoids, such as all-cis retinoic acid, 13-trans retinoic acid, and other vitamin A and beta carotene derivatives; vitamins D, E, and K and water insoluble precursors and derivatives thereof; prostaglandins and leukotrienes and their activators and inhibitors including prostacyclin (epoprostanol), and prostaglandins; tetrahydrocannabinol; lung surfactant lipids; lipid soluble antioxidants; hydrophobic antibiotics and chemotherapeutic drugs such as amphotericin B and adriamycin and the like. In one aspect, the hydrophobic drug is selected from the following classes of compounds: chemotherapeutic, antibiotic, antimicrotubule, anti-inflammatory, and antiproliferative compounds. In a preferred aspect, the hydrophobic drug is selected from paclitaxel, hydrophobic paclitaxel derivatives and hydrophobic paclitaxel analogs. In another preferred aspect, the hydrophobic drug is paclitaxel.

The hydrophobic drug may be combined directly with Compound$_1$ and/or Compound$_2$. Alternatively, the hydrophobic drug may be combined with a secondary carrier, e.g., a micelle, where the secondary carrier assists in solubilization and/or delivery of the drug. The drug/secondary carrier mixture is then combined directly with Compound$_1$ and/or Compound$_2$, and/or added separately to the mixture of Compound$_1$ and Compound$_2$. The secondary carrier is particularly useful in those instances where the drug is hydrophobic and does not readily dissolve in water. In one embodiment (e.g., in which the drug is hydrophobic), the drug is associated with a secondary carrier. Optionally, this drug/carrier combination is present in an aqueous buffer solution that is combined with Compound$_1$ and/or Compound$_2$ and/or the reaction product thereof. Suitable secondary carriers are described herein. However, a preferred secondary carrier is described in PCT International Publication No. WO 02/072150 and U.S. patent application Ser. No. 10/251,659.

Optional Composition Constituents

In addition to the reactive compounds and the drug, the compositions of the present invention may also contain other compounds, which may be included in one or both of the components of the two-component compositions, or may be separately administered. In one embodiment, these compounds may become covalently incorporated into the matrix itself by becoming crosslinked to one or both of the reactive compounds after they are mixed together. In another embodiment, (e.g., if the compound was unreactive with either of the reactive compounds), the compound may be administered in such a way that it becomes physically or ionically associated with the matrix-forming compounds after mixing, and thus becomes part of the matrix itself.

Additional compounds that may be added into the instant compositions include glycosaminoglycans and proteins. Suitable glycosaminoglycans include, inter alia, hyaluronic acid, chitin, chitosan, chondroitin sulfate A, B, or C, keratin sulfate, keratosulfate and heparin, and derivatives thereof. In another embodiment, proteins can be added for a variety of purposes. For example, collagen may improve biocompatibility of the matrix, including the potential colonization by cells, promotion of wound healing, etc. Collagen and any amino group-containing proteins would also contribute to the structural integrity of the matrix by becoming crosslinked thereto along with the other matrix components. In particular, if PEG-succinimidyl esters are used, the amide bonds formed with collagen will be more stable to hydrolytic degradation than the bonds formed by the reaction of succinimidyl esters and sulfhydryls.

Suitable proteins include, inter alia, collagen, fibronectin, gelatin and albumin, as well as peptide fragments thereof. Particularly preferred is collagen, which may be in the form of afibrillar, microfibrillar or fibrillar collagen. Types I and III collagen isolated from bovine corium or human placenta, or prepared by recombinant DNA methods, are suitable. See PCT WO 90/05755 for a description of suitable collagens and collagen derivatives. It should be understood that when adding collagen to the composition, it is important to adjust the concentration of the other composition components to avoid precipitation.

Additional constituents which may be added to the composition include antibiotics, growth factors, hemostatic proteins (such as thrombin, fibrin, fibrinogen, blood factors, etc.), cells, genes, DNA, etc.

In one aspect, the compositions of the present invention include one or more preservatives or bacteriostatic agents, present in an effective amount to preserve the composition and/or inhibit bacterial growth in the composition, for example, bismuth tribromophenate, methyl hydroxybenzoate, bacitracin, ethyl hydroxybenzoate, propyl hydroxybenzoate, erythromycin, chlorocresol, benzalkonium chlorides, and the like. Examples of the preservative include paraoxybenzoic acid esters, chlorobutanol, benzylalcohol, phenethyl alcohol, dehydroacetic acid, sorbic acid, etc. In one aspect, the compositions of the present invention include one or more bactericidal (also known as bacteriacidal) agents.

In one aspect, the compositions of the present invention include one or more antioxidant, present in an effective amount. Examples of the antioxidant include sulfites and ascorbic acid.

In one aspect, the compositions of the present invention include one or more coloring agents, also referred to as dyestuffs, which will be present in an effective amount to impart observable coloration to the composition, e.g., the gel. Examples of coloring agents include dyes suitable for food such as those known as F. D. & C. dyes and natural coloring agents such as grape skin extract, beet red powder, beta carotene, annato, carmine, turmeric, paprika, and so forth.

Optional Composition Properties and Packaging

In one aspect, the compositions of the present invention are sterile. Many pharmaceuticals are manufactured to be sterile and this criterion is defined by the USP XXII <1211> where the term "USP" refers to U.S. Pharmacopeia (see www.usp.org, Rockville, Md.). Sterilization in this embodiment may be accomplished by a number of means accepted in the industry and listed in the USP XXII <1211>, including gas sterilization, ionizing radiation or, when appropriate, filtration. Sterilization may be maintained by what is termed aseptic processing, defined also in USP XXII <1211>. Acceptable gases used for gas sterilization include ethylene oxide. Acceptable radiation types used for ionizing radiation methods include gamma, for instance from a cobalt 60 source and electron beam. A typical dose of gamma radiation is 2.5 MRad. Filtration may be accomplished using a filter with suitable pore size, for example 0.22 μm and of a suitable material, for instance Teflon.

In another aspect, the compositions of the present invention are contained in a container that allows them to be used for their intended purpose, i.e., as a pharmaceutical composition. Properties of the container that are important are a volume of empty space to allow for the addition of a constitution medium, such as water or other aqueous medium, e.g., saline, acceptable light transmission characteristics in order to prevent light energy from damaging the composition in the container (refer to USP XXII <661>), an acceptable limit of extractables within the container material (refer to USP XXII), an acceptable barrier capacity for moisture (refer to USP XXII <671>) or oxygen. In the case of oxygen penetration, this may be controlled by including in the container, a positive pressure of an inert gas, such as high purity nitrogen, or a noble gas, such as argon.

Typical materials used to make containers for pharmaceuticals include USP Type I through III and Type NP glass (refer to USP XXII <661>), polyethylene, polytetrafluoroethylene (e.g., TEFLON from E.I. DuPont De Nemours and Company, Wilmington, Del.), silicone, and gray-butyl rubber. For parenterals, USP Types I to III glass and polyethylene are preferred.

Incorporation of Biologically Active Agents into the Compositions

Biologically active agents can be incorporated directly into the composition or they can be incorporated into a secondary carrier. Accordingly, a secondary carrier is another optional constituent of the compositions of the present invention. For direct incorporation of the biologically active agent, the agent may or may not contain electrophilic or nucleophilic group or groups that can react with either the activated functional groups of the synthetic polymer of the composition. The biologically active agents can be incorporated into the composition before the components of the composition are brought together to produce the crosslinked composition or after the components of the composition are brought together to form the crosslinked composition. The biologically active agent can be admixed with either of the starting components, admixed with both of the starting components, admixed with the admix of both starting components, admixed with either or both of the starting components at the time of application or incorporated into the composition at a time after the starting components have been mixed or reacted with each other. A combination of these methods may also be used to incorporate the biologically active agent into the composition. The presence of the appropriate electrophilic or nucleophilic groups on the biologically active agent will allow the biologically active agent to be incorporated into the final composition via chemical bonds. The absence of the appropriate electrophilic or nucleophilic groups on the biologically active agent will allow the biologically active agent to be incorporated into the final composition via physical entrapment, electrostatic interactions, hydrogen bonding, hydrophobic interactions, Van Der Waals interactions or a combination of these interactive forces. A single biologically active agent may be directly incorporated into the composition or a combination of biologically active agents may be incorporated into the composition using any of the possible approaches described above.

For the incorporation of the biologically active agent into the composition via the use of a secondary carrier, which is a preferred embodiment when the drug is hydrophobic, the biologically active agent can be incorporated into the secondary carrier by covalent linking to the secondary carrier, physical entrapment, adsorption, electrostatic interactions, hydrophobic interactions, partitioning effects, precipitation in the secondary carrier or a combination of these interactions. This biologically active agent/secondary carrier composition can then be incorporated directly into the composition (either with Compound$_1$ or with Compound$_2$ or with both Compound$_1$ and Compound$_2$) or they can be used as a separate component of the composition.

The secondary carriers that can be used to incorporate these biologically active agents may be in the form of particulates, microparticles, nanoparticles, nanocrystals, microspheres, nanospheres, liposomes, micelles, emulsions, microemulsions, dispersions, inclusion complexes, non-ionic surfactant vesicles (NISV), niosomes, proniosomes, cochleates, immunostimulating complexes (ISCOMs) and association complexes. In one embodiment, the microparticles, nanoparticles or microspheres can be prepared using polymers and copolymers that include one or more of the residue units from the following monomers: D-lactide, L-lactide, D,L-lactide, glycolide, β-caprolactone, trimethylene carbonate, 1,4-dioxane-2-one, or 1,5-dioxepan-2one. In another embodiment, the microparticles, nanoparticles, or microspheres can be prepared using block copolymers of the for A-B, A-B-A or B-A-B where A is a poly(alkylene oxide) (e.g., poly(ethylene glycol), poly(propylene glycol), copolymers of ethylene oxide and propylene oxide, or mono-alkyl ethers thereof) and be is a degradable polyester, for example polymers and copolymers comprising one or more of the residue units of the monomers D-lactide, L-lactide, D,L-lactide, glycolide, ε-caprolactone, trimethylene carbonate, 1,4-dioxane-2-one or 1,5-dioxepan-2-one). Micelles can be prepared using small molecule surfactants (e.g., SDS) or polymeric compositions (e.g., PLURONIC F127 or PLURONIC F68 (both available from BASF Corporation, Mount Olive, N.J.), block copolymers of the form A-B, A-B-A or B-A-B, where A is a poly(alkylene oxide) e.g., poly(ethylene glycol), poly(propylene glycol), copolymers of ethylene oxide and propylene oxide, or mono-alkyl ethers thereof) and B is a degradable polyester, for example polymers and copolymers comprising one or more of the residue units of the monomers D-lactide, L-lactide, D,L-lactide, glycolide, ε-caprolactone, trimethylene carbonate, 1,4-dioxane-2-one or 1,5-dioxepan-2-one). Albumin, alginate, gelatin, starch, collagen, chitosan, poly(anhydrides), poly(orthoesters), poly(phosphazines) can also be used to prepare these secondary carriers. Liposome compositions can include phosphatidyl choline, cholesterol, phosphatidyl ethanolamine as well as any of the commercially available lipids (for example, lipids available from Avanti Polar Lipids). Non-polymeric compounds such as sucrose derivatives (e.g., sucrose acetate isobutyrate, sucrose oleate); sterols such as cholesterol, stigmasterol, β-sitosterol, and estradiol; cholesteryl esters such as cholesteryl stearate; $C_{12}$-$C_{24}$ fatty acids such as lauric acid, myristic acid, palmitic acid, stearic acid, arachidic acid, behenic acid, and lignoceric acid; $C_{18}$-$C_{36}$ mono-, di- and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl dideceneoate, glyceryl tridocosanoate, glyceryl trimyristate, glyceryl tridecenoate, glycerol tristearate and mixtures thereof; sucrose fatty acid esters such as sucrose distearate and sucrose palmitate; sorbitan fatty acid esters such as sorbitan monostearate, sorbitan monopalmitate and sorbitan tristearate; $C_{16}$-$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof; sphingosine and derivatives thereof; spingomyelins such as stearyl, palmitoyl, and tricosanyl spingomyelins; ceramides such as stearyl and palmitoyl ceramides; glycosphingolipids; lanolin and lanolin alcohols, calcium phosphate can also be used as part of the secondary carrier composition.

In one embodiment, one or more additives can be added to the drug component, the PEG components or the secondary carriers in order to modulate the pH or the composition and/or release of the drug from the composition. These additives can include neutral, positively or negatively charged lipids, fatty acids, amino-containing molecules or bile salts. Specific examples of additives that can be used include histidine, spermidine, 1,2 dipalmitoyl-sn-glycero-3-phosphoethanolamine, 3-ethylphosphocholine chloride, palmitic acid or cholic acid.

The biologically active agent/secondary carrier composition can be admixed with either of the starting components, admixed with both of the starting components, admixed with the admix of both starting components, admixed with either or both of the starting components at the time of application or incorporated into the composition at a time after the starting components have been mixed or reacted with each other. A combination of these methods may also be used to incorporate the biologically active agent/secondary carrier into the composition.

The biologically active agent/secondary carrier composition can contain groups that may or may not be able to react with the electrophilic or nucleophilic groups of the starting components. In one embodiment, the secondary carrier does not contain electrophilic or nucleophilic groups that can react with the starting polymer components, in which case the secondary carrier/biologically active agent is retained within the final composition through physical entrapment, hydrophobic, hydrogen bonding, Van der Waals interactions, electrostatic interactions or a combination of these interactive forces.

In another embodiment, the biologically active agent/secondary carrier composition may contain functional groups that can react with either the electrophilic or nucleophilic groups of the starting components. Under these circumstances, the biologically active agent/secondary carrier composition is retained in the final composition via covalent bonds. Other interactions such as physical entrapment, hydrophobic, hydrogen bonding, Van der Waals interactions, electrostatic interactions or a combination of these interactive forces may also contribute to the retention of the biologically active agent/secondary carrier in the final composition.

Compounds containing one or more of the following functional groups: —$NH_2$, —SH, —OH, —$PH_2$, —CO—NH—$NH_2$, —$CO_2N(COCH_2)$, —$CO_2H$, —CHO, —$CHOCH_2$, —N=C=O, —$SO_2CH$=$CH_2$, —$N(COCH_2)_2$, —S—S—($C_5H_4N$), $CH_2$=CH—, $CH_2$=CH—COO—, $CH_2$=CH—CO—NH— etc. are compounds that can be incorporated into the secondary carriers thereby providing the secondary carriers with functional groups that are capable of reacting with the starting components of the crosslinked composition.

Examples of useful amino compounds that can be incorporated into the secondary carriers to provide functional groups on the secondary carrier include phosphatidyl ethanolamine lipids (for example, Avanti Polar Lipids, Inc. Catalogue #850757, 850756, 850759, 850801, 850758, 850802, 850804, 850806, 850697, 850699, 850700, 850702, 850745, 850705, 850402, 850706, 830756C, 830756P, 850715, 850725, 85T725, 850755, 850795, 850800, 850797, 870125, 870122, 870140, 870142, 856705, 856715, 846725), alkyl amines, aryl amines, and cycloalkyl amines.

Examples of useful thiol compounds that can be incorporated into the secondary carriers to provide functional groups on the secondary carrier includes 1,2-Dipalmitoyl-sn-Glycero-3-Phosphothioethanol (Sodium Salt) (Avanti Polar Lipids, Catalogue #870160), alkyl thiols, and aryl thiols.

Other methods of incorporated a drug with $Compound_1$ and $Compound_2$ are illustrated in PCT International Publication No. WO 00/09087.

The cells or genes may be either allogeneic or xenogeneic in origin. For example, the compositions can be used to deliver cells or genes from other species which have been genetically modified. Because the compositions of the invention are not easily degraded in vivo, cells and genes entrapped within the crosslinked polymer compositions will be isolated from the patient's own cells and, as such, will not provoke an immune response in the patient. In order to entrap the cells or genes within a crosslinked polymer matrix, the first polymer and the cells or genes may be pre-mixed, then the second polymer is mixed into the first polymer/cell or gene mixture to form a crosslinked matrix, thereby entrapping the cells or genes within the matrix.

As discussed above for biologically active agents, when used to deliver cells or genes, the synthetic polymers preferably also contain biodegradable groups to aid in controlled release of the cells or genes at the intended site of delivery.

Composition Formulation

The compositions of the present invention comprise two separate parts, or "components", which may be in liquid or solid form. In a preferred embodiment, both components are liquids, such that each can be easily applied separately to the site of administration. Accordingly, one of the components may be in the form of a dry powder that becomes mixed with the second component, which is in liquid form, when each are sprayed separately onto the tissue, or by mixing at the tissue site. It is also possible to have both components delivered to the site as powders, to be mixed with buffer at the site of administration.

In an alternative embodiment, both components can be mixed together in a single aqueous medium in which they are both unreactive, i.e., such as in a low pH buffer. Thereafter, they can be sprayed onto the tissue site along with a high pH buffer, after which they will rapidly react and form a gel.

The concentration of the reactive compounds in each of the composition components necessarily depends on a number of factors. For example, if the composition components are each 4-arm PEGs (i.e., PEG-PEG compositions), a concentration of 20-25% by weight in each of the two components before mixing results in a gel after mixing with an elastic modulus, G', of approximately $10^5$-$10^6$ dynes/cm$^2$, which is adequate for use as a surgical sealant. Using methylated collagen and 4-arm succinimidyl PEG, concentrations of 2-4% and 0.2-0.4%, respectively, result in gels with cohesive strengths that are comparable to PEG-PEG gels by about 10-15%. Using albumin as one of the components, concentrations of 30% or more achieve a similar cohesive strength. The appropriate concentration of the compound, and other optional ingredients, in each component, and thus the relative concentration of the matrix components in the final gel matrix, can easily be optimized to achieve the desired gelation time and gel strength using routine experimentation. Using the preferred four-arm PEGs described above, the synthetic polymer is generally present at a concentration of 2 to 50% (w/v), and more preferably 10-25%.

The liquid components of the compositions of the present invention are each separately prepared by adding the activated synthetic polymer (in dry form or as a concentrated solution) to a liquid medium. Suitable liquid media include aqueous buffer solutions, such as monobasic sodium phosphate/dibasic sodium phosphate, sodium carbonate/sodium bicarbonate, glutamate or acetate, at a concentration of 0.5 to 300 mM. In general, the sulfhydryl-reactive PEG is prepared in water or a dilute buffer, with a pH of between around 2 to 6. Buffers with pHs between about 8 to 10.5 for preparing the sulfhydryl-PEG component are useful to achieve fast gelation time of compositions containing mixtures of sulfhydryl-PEG/SG-PEG. These include carbonate, borate and AMPSO (3-[(1,1-dimethyl-2-hydroxyethyl)amino]2-hydroxy-propane-sulfonic acid). In contrast, using a combination of maleimidyl PEG and sulfhydryl-PEG, a pH of around 5 to 9 is preferred for the liquid medium used to prepare the sulfhydryl PEG. A particularly preferred composition for hemostatic applications to actively bleeding tissue sites comprises a mixture of maleimidyl and succinimidyl PEG as the first component, and sulfhydryl PEG as the second component. Such compositions produce gels with enhanced biodegradability and superior gel times when compared to compositions having only maleimidyl PEG or succinimicyl PEG alone.

The pH of the aqueous buffer solution that is used for each of the two (or more) composition components should be adjusted using routine optimization to achieve a final pH that is conducive to rapid gelation, without causing instantaneous gelation which interferes with the delivery process. For example, both amino PEG and sulfhydryl PEG need a basic pH to enhance nucleophilicity. The effects of pH on gel time are discussed below in the Examples.

Use and Administration

The compositions of the present invention are generally delivered to the site of administration in such a way that the two (or more) individual reactive components of the composition come into contact with one another for the first time at the site of administration, or immediately preceding administration to the tissue. Thus, the compositions of the present invention are preferably delivered to the site of administration using an apparatus that allows the two components to be delivered separately. Such delivery systems usually involve two-compartment single exit or dual exit spray devices. Alternatively, the two reactive components can be delivered separately using any type of controllable extrusion system, or they can be delivered manually in the form of separate pastes, liquids or dry powders, and mixed together manually at the site of administration. Many devices that are adapted for delivery of two-component tissue sealants/hemostatic agents are well known in the art and can also be used in the practice of the present invention. In this regard, see, for example, U.S. Pat. No. 6,328,229.

Yet another way of delivering the compositions of the present invention is to prepare the two reactive components (or the single reactive component in the case of sulfhydryl-containing components that are designed to form disulfide bonds) in inactive form as either a liquid or powder. Such compositions can then be activated after application to the tissue site, or immediately beforehand, by applying an activator. In one embodiment, the activator is a buffer solution having a pH that will activate the composition once mixed therewith. See Example 12 for a description of a sulfhydryl-containing PEG composition that is maintained at a low pH until administration, then mixed with a high pH buffer at the application site to initiate gelation.

The compositions of the present invention can be used in a variety of different pharmaceutical applications. In general, the compositions described herein can be adapted for use in any tissue engineering application where synthetic gel matrices are currently being utilized. For example, the compositions of the present invention are useful as tissue sealants, in tissue augmentation, in tissue repair, as hemostatic agents, in preventing tissue adhesions, in providing surface modifications, and in drug/cell/gene delivery applications. One of skill in the art could easily determine the appropriate administration protocol to use with any composition having a known gel strength and gelation time based on the principles described herein and well known scientific principles. A more detailed description of several specific applications is given below:

Tissue Sealants & Adhesives

In a preferred application, the compositions described herein can be used for medical conditions that require a coating or sealing layer to prevent the leakage of gases, liquid or solids. The method entails applying both components to the damaged tissue or organ to seal 1) vascular and or other tissues or organs to stop or minimize the flow of blood; 2) thoracic tissue to stop or minimize the leakage of air; 3) gastrointestinal tract or pancreatic tissue to stop or minimize the leakage of fecal or tissue contents; 4) bladder or ureters to stop or minimize the leakage of urine; 5) dura to stop or minimize the leakage of CSF; and 6) skin or serosal tissue to stop the leakage of serosal fluid.

These compositions may also be used to adhere tissues together such as small vessels, nerves or dermal tissue. The material can be used 1) by applying it to the surface of one tissue and then a second tissue may be rapidly pressed against the first tissue or 2) by bringing the tissues in close juxtaposition and then applying the material.

Surgical Adhesions

Another application is a method of reducing the formation of adhesions after a surgical procedure in a patient. The method entails applying the material onto the damaged tissue or organ either by spraying both components together or by applying previously admixed components. The components will react together to form a hydrogel on the tissue surface. The medical procedures include gynecological, abdominal, neurosurgical, cardiac, tendon and orthopedic indications.

General Procedure A

Sprague Dawley rats are prepared for surgery by anaesthetic induction with 5% halothane in an enclosed chamber. Animals are transferred to the surgical table, and anaesthesia maintained by nose cone on halothane throughout the procedure and Buprenorphen 0.035 mg/kg is injected intramuscularly. The abdomen is shaved, sterilized, draped and entered via a midline incision. The caecum is lifted from the abdomen and placed on sterile gauze dampened with saline. Dorsal and ventral aspects of the caecum are scraped a total of 45 times over the terminal 1.5 cm using a #10 scalpel blade, held at a 45° angle. Blade angle and pressure are controlled to produce punctuated bleeding, while avoiding severe tissue damage or tearing.

The left side of the abdominal cavity is retracted and everted to expose a section of the peritoneal wall nearest the natural resting caecal location. The exposed superficial layer of muscle (transverses abdominis) is excised over an area of $1.0 \times 1.5$ cm$^2$. Excision includes portions of the underlying internal oblique muscle, leaving behind some intact and some torn fibres from the second layer. Minor local bleeding is tamponaded until controlled.

A test formulation is deployed at the wounded areas, on the abraded sidewall, between the caecum and sidewall. The formulation is deployed using either a syringe spray system or an air-assisted syringe system. The abraded caecum is then positioned over the sidewall wound and sutured at four points immediately beyond the dorsal corners of the wound edge. The large intestine is replaced in a natural orientation continuous with the caecum. The abdominal incision is closed in two layers with 4-0 silk sutures.

Healthy subjects are followed for one week, and then euthanized by lethal injection for post mortem examination to score. Severity of post-surgical adhesions is scored by independently assessing the tenacity and extent of adhesions at the site of caecal-sidewall abrasion, at the edges of the abraded site, and by evaluating the extent of intestinal attachments to the exposed caecum. Adhesions are scored on a scale of 0-4 with increasing severity and tenacity. The extent of adhesion is scored as a percent of the injured area that contained adhesions.

General Procedure B

Female New Zealand white rabbits weighing between 3-4 kg are used for surgeries. The animals are acclimated in the vivarium for a minimum of 5 days prior to study initiation and housed individually. Animals are anesthetized by a single injection of ketamine hydrochloride (35 mg/kg) and xylanzine hydrochloride (5 mg/kg). Once sedated, anesthesia is induced with halothane or isofluorane delivered through a mask until the animal is unconscious, when an endotracheal tube is inserted for delivery of halothane or isofluorane to sustain surgical anesthesia. The abdomen is shaved, swabbed with antiseptic, and sterile-draped for surgery. A midline vertical incision 6-7 cm in length is made with a #10 scalpel blade. The uterine horns are brought through the incision and each horn is abraded 20 times in each direction with a #10 scalpel blade held at a 45° angle. A region of the uterine horn, approximately 2 cm in length is abraded along the circumference of the horn, beginning 1 cm from the ovaric end. This injury results in generalized erythema without areas of active bleeding. Each side of the abdominal cavity is retracted and everted to expose a section of the peritoneal wall nearest the natural resting location of the horn. The sidewall apposed to the abraded uterine horn is injured by removing a $2.0 \times 0.5$ cm$^2$ area of the peritoneum. The abraded uterine horn is then positioned over the sidewall wound and sutured at four points of the wound edge. Following completion of the abrasion, before closure, animals are randomized into treatment and non-treatment groups. Treated animals have approximately 1 ml of the desired formulation applied to each horn at the site of attachment to the sidewall. Healthy subjects are followed for one week, and then euthanized by lethal injection for post mortem examination to score the severity of inflammation and adhesions using established scoring systems. Post-surgical adhesions are scored by independently assessing the extent, severity and tenacity of adhesions of each horn to the peritoneal sidewall. Adhesions are scored on a scale of 0-4 depending involvement of the horn in adhesions and a scale of 0-3 with increasing severity and tenacity.

EXAMPLES

Example 1

Preparation of a Two-Component Tissue Sealant Composition a. First Component

Pentaerythritol poly(ethylene glycol)ether tetra-succinimidyl glutarate ("SG-PEG") (mol. wt. 10,000) is dissolved in 0.5 mM sodium phosphate pH 6.0 at a concentration of 20% w/v. (This solution is not stable in aqueous media due to the susceptibility of the active ester to hydrolysis and should be used within one hour of preparation).

b. Second Component

Pentaerythritol poly(ethylene glycol)ether tetra-sulfhydryl (mol. wt. 10,000) is dissolved in 300 mM sodium phosphate/sodium carbonate buffer ("P/C buffer"), pH 9.6, at a concentration of 20% w/v. P/C buffer is prepared as follows: 300 mM sodium monobasic phosphate is mixed with 300 mM sodium carbonate to achieve pH 9.6. The final molarity is approximately 117 mm phosphate and 183 mM carbonate. This solution is stable in aqueous media, but care should be taken to prevent the exposure of the solution to oxygen to prevent oxidation to disulfide. Although pH is preferred for certain compositions, a pH of 8 to 10.5 is generally believed to be suitable for use in the practice of the present invention.

Example 2

Surgical Sealing of Arteries

The right carotid artery of New Zealand white rabbits is exposed. The rabbits are treated with 200 U/kg of heparin and the vessel is clamped proximally and distally using atraumatic vascular clamps. A puncture hole is made in the carotid artery using a 27G needle. The control rabbits are treated with tamponade until hemostasis is achieved. For the treated rabbits, approximately 0.5 mL of each of the two components of the compositions prepared as described in Example 1 are delivered to the defect site using a two component sprayer (Duo Flow, Hemaedics, Malibu, Calif.). After the material is allowed to set for 30 sec, the clamps are removed and the time to hemostasis and the blood loss are measured. The arteries of the control rabbits also remain clamped for 30 sec for consistency. The results are shown in Table 1.

TABLE 1

Blood Loss and Time to Hemostasis as a Function of Treatment

| Treatment | Blood Loss (g) | Time to Hemostasis (sec) |
|---|---|---|
| Tamponade (n = 18) | 5.7 ± 3.4 | 144 ± 34 |
| Hydrogel (n = 17) | 1.0 ± 2.5 | 31 ± 65 |

The above results illustrate that the composition significantly reduces the amount of blood loss and time to hemostasis from a punctured artery.

Example 3

Surgical Sealing of an ePTFE Graft

The dogs are treated with heparin to achieve an activated clotting time of greater than 480 sec. The left iliac of the dogs is exposed and isolated using atraumatic vascular clamps placed distally and proximally. A 5 cm segment of the artery is excised and replaced with an ePTFE (polythetrafluoroethylene) graft of the same diameter. Prior to the completion of the anastamosis, the graft was de-aired using a 27G needle. Approximately 3.0 mL of each of the two components of the composition prepared according to Example 1 is delivered to the defect site using a two component sprayer (Cohesion Technologies, Inc., Palo Alto, Calif.). After the material is allowed to set for 30 sec, the clamps are removed and the time to hemostasis and the blood loss are measured. The procedure was repeated on the left iliac, with the exception of material application. The right iliac received only tamponade treatment. The results are shown in Table 2.

TABLE 2

Blood Loss and Time to Hemostasis as a Function of Treatment

| Treatment | Blood Loss (g) | Time to Hemostasis (sec) |
|---|---|---|
| Tamponade (n = 2) | 244, 180 | >15, >15 |
| Hydrogel (n = 2) | 18, 7 | 3.3, 2.3 |

The above results illustrate that this composition significantly reduces the amount of blood loss and time to hemostasis from an ePTFE anastamosis.

Example 4

Enhanced Biocompatibility of Thioester-Linked Formulations

Up to six subcutaneous pockets are made on the backs of New Zealand white rabbits. Approximately 1.0 mL of each of the components of the composition described in Example 1 is delivered to the defect site using a two component sprayer (Cohesion Technologies, Inc., Palo Alto, Calif.) for liquid formulations or a spatula for formulations that are gelled ex-vivo. The grading key is shown in Table 3 and the results are shown in Table 4.

TABLE 3

Grading Key for Biocompatibiltiy Experiments

| Score | Gross Observations | Histological Observations |
|---|---|---|
| − | All tissues appeared normal | all tissues appeared normal, no inflammation |
| + | mild foreign body response | mild inflammation |
| ++ | moderate foreign body response | moderate inflammation |
| +++ | marked foreign body response | marked inflammation |
| ++++ | Severe foreign body response | severe inflammation |

TABLE 4

Results for Biocompatibility Experiments

| Test | Description | Gross Observations | Histological Observations |
|---|---|---|---|
| A | Surgical control | − | + |
| B | Fibrillar collagen | − | + |
| C | 20% w/v tetra-SG PEG 10,000<br>20% w/v tetra-amino PEG 10,000 | ++++ | ++++ |
| D | 20% w/v tetra-SG PEG 10,000<br>20% w/v tetra-sulfhydryl PEG 10,000 | ++ | ++ |
| E | 20% w/v tetra-SG PEG 10,000<br>20% w/v tetra-amino PEG 10,000;<br>gelled ex-vivo; treated with mono-SG PEG 5000 | + | ++ |
| F | 20% w/v tetra-SG PEG 10,000<br>20% w/v di-sulfhydryl PEG 3,400;<br>gelled ex-vivo; treated with di-amino PEG 3400 | ++++ | ++++ |

Experiments A and B show a mild gross and histological response of fibrillar collagen (Cohesion Technologies, Palo Alto, Calif.) and the surgical control. Experiment C shows a severe response to hydrogels made with amino-PEG. The response consists of thick encapsulation of the hydrogel and abscess formation. By substitution of sulfhydryl-PEG for amino-PEG, as in Experiment D, the biocompatibility of the hydrogel is significantly improved. Experiment E involves forming an amino hydrogel ex-vivo and incubating the hydrogel in a solution of mono-SG PEG, 5000 mol. wt. During the incubation period, the mono-SG PEG reacts with the free amines present on the hydrogel network, thus reducing the amount of free amines on the polymeric network. This treatment enhances the biocompatibility of the hydrogel. Experiment F involves forming a sulfhydryl hydrogel ex-vivo and incubating the hydrogel in a solution of mono-SG PEG, 5000 mol. wt. During the incubation period, the di-amino PEG reacts with the free SG groups present on the hydrogel network, thus increasing the amount of free amines on the polymeric network. This treatment decreases the biocompatibility of the hydrogel. Thus, these results show the enhanced biocompatibility of sulfhydryl formulations over amino formulations.

Example 5

Effect of Buffer and Reactive Group on Gel Times

A desirable characteristic of the compositions described herein is their ability to rapidly achieve gelation. In this experiment, the effects of buffer strength and composition on gelation kinetics are studied. For all experiments, the tetrafunctional SG PEG described in Example 1 is dissolved in 0.5 mM sodium phosphate, pH 6.0, and the tetra-sulfhydryl PEG described in Example 1, or the equivalent tetra-amino PEG is dissolved in the buffer listed in Table 5.

TABLE 5

Effect of Phosphate vs. Carbonate Buffer on Amino and Sulfhydryl Fomulations

| Test | Formulation | Buffer | Gel Time (sec) |
|---|---|---|---|
| A | 10% w/v tetra-SG PEG 10,000 + 10% w/v tetra-amino PEG 10,000 | 300 mM dibasic sodium phosphate pH 9 | 16 |
| B | 10% w/v tetra-SG PEG 10,000 + 10% w/v tetra-sulfhydryl PEG 10,000 | 300 mM dibasic sodium phosphate pH 9 | 55 |
| C | 10% w/v tetra-SG PEG 10,000 + 10% w/v tetra-amino PEG 10,000 | 300 mM sodium carbonate pH 9 | 14 |
| D | 10% w/v tetra-SG PEG 10,000 + 10% w/v tetra-sulfhydryl PEG 10,000 | 300 mM sodium carbonate pH 9 | 9 |
| E | 10% w/v tetra-SG PEG 10,000 + 10% w/v tetra-sulfhydryl PEG 10,000 | P/C Buffer pH 9.6 | 3 |

Experiments A and B show the difference in gel times in amino formulations and sulfhydryl formulations in phosphate buffer. In this buffer, an increase in gelation rate is observed for sulfhydryl formulations compared to amino formulations. Experiments C and D show the difference in gelation times in amino formulations and sulfhydryl formulations in carbonate buffer. As shown, a decrease in gel time is observed for sulfhydryl formulations in carbonate buffer. In the preferred P/C Buffer, a gel time of 3 seconds is observed.

Example 6

Rheometric Measurements

The first component (tetra-functional Sulfhydryl-PEG, 10,000 mol. wt.) was prepared according to Example 1 and suspended in P/C Buffer. The second component (tetra-functional SG-PEG, 10,000 mol. wt.) was prepared according to Example 1 in 0.5 mM phosphate, pH 6.0. The two components (0.6 ml each) were loaded in a dual-syringe device with joiner and cannula. The cannula contained a mixing element. The solutions were mixed, and the resultant mixture was immediately delivered into a parallel plate cell of a Rheometrics Fluids Spectrometer 8500 (Rheometrics, Inc., Piscataway, N.J.). The upper platen had a diameter of 25 mm, and the gap between upper and lower parallel plates was 1.5 mm.

Figure 4:
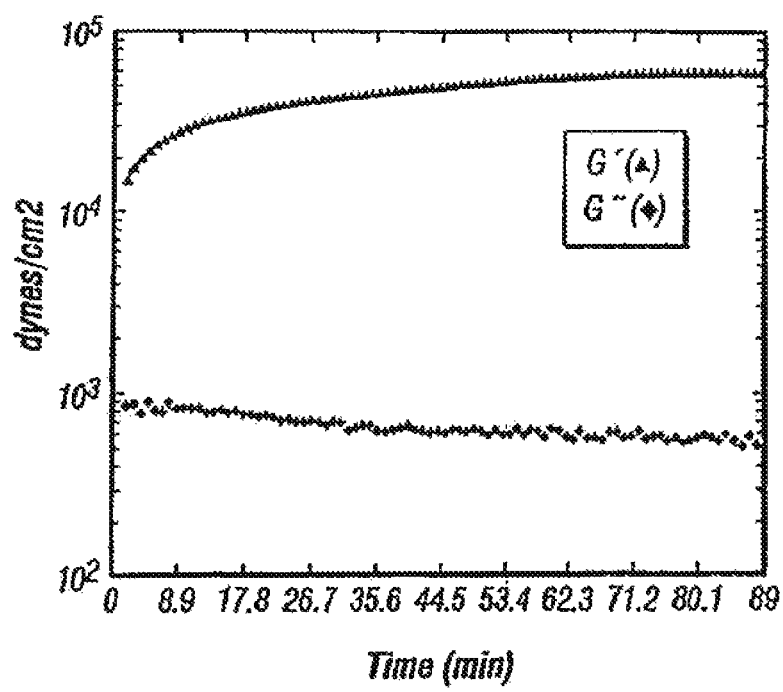
FIG. 4 depicts the rheometric measurements of gelation of a mixture of reactive tetrafunctional polyethylene glycols.

Gelation began immediately upon mixing of the formulation. The instrument was started, and G' and G" (elastic and viscous moduli, respectively) were measured at 1% strain and 1 radian/sec. In less than a minute, G' was near $10^4$ dynes/cm$^2$, which is characteristic of a soft rubbery material. G' began to plateau within 15 min, and continued to rise very gradually for more than an hour afterwards. G" was in the order of $10^2$ dynes/cm$^2$, and declined gradually. These results are consistent with a rapidly gelling material. G' and G" for the unreacted starting materials was about 1-10 dynes/cm$^2$. These results are depicted in FIG. 4.

In this experiment, the rheometer cannot precisely quantitate G' and G" below about 50 dynes/cm$^2$. In addition, the gelation occurred so rapidly that the mixture only filled 30 to 95% of the desired space—there was gelled fluid surrounding the plate, but not between the plates. Even with these limitations, a measurement of the elastic (G') and viscous modulus (G") as a function of time can still be made, and the kinetics of gelation can be followed. As indicated in this experiment, a G' of greater than $10^2$ dynes/cm$^2$ in less than one minute indicates rapid gelation.

Example 7

Effects of Buffers on Gel Time Using Sulfhydryl-Peg and N-Hydroxy-Succinimidyl-PEG (NHS-PEG)

All tests were done with 50 ml of 20% (w/v) 4 arm, 10,000 mol. wt., tetrafunctional SG-PEG mixed with 50 ml of 20% (w/v) 4 arm, 10,000 mol. wt., tetra-functional sulfhydryl-PEG). Different buffers were used, and the times to gel were noted. The SG-PEG was dissolved in 0.5 mM phosphate, pH 6.0 for all tests. The sulfhydryl-PEG was dissolved in the buffers given below at a pH of 9.6 and times to gel are noted.

TABLE 6

Effect Buffers on Gelation Time

| Test | Buffer | Gel Time (Sec) |
|---|---|---|
| A | P/C Buffer | 8 |
| B | 150 mM phosphate | 35 |
| C | 58 mM phosphate 91 mM sodium chloride | 138 |
| D | 58 mM phosphate 91 mM borate | <19 |
| E | 58 mM phosphate 91 mM AMPSO* | 8 |

*(3[1,1-dimethyl-2-hydroxy-ethyl)amino]-2-hydroxypropane-sulfonic acid

As shown, buffers with pKs between 8 and 10.5 (borate, 8.1; carbonate, 10.3; AMPSO, 9.0), and mixtures thereof, are suitable Example 8

Sulfhydryl-Reactive PEGs

The gelation characteristics of several different formulations are described below:

8a: Gelation of Di Functional Maleimidyl-PEG, 3400 mol. wt. (MAL-PEG) with Tetra-Sulfhydryl PEG, 10,000 mol. wt.

A 20% (w/v) solution of MAL-PEG in 0.5 mM sodium phosphate, pH 6.0, was mixed rapidly with an equal volume of 20% (w/v) tetra-sulfhydryl PEG in 150 mM sodium phosphate, pH 5.0. Gelation occurred in 15 sec. The gel became a firm, rubbery solid in a minute or less.

8b: Gelation of Difunctional Iodoacetamide PEG, 3,400 mol. wt. ("IAM-PEG") with Tetra-Sulfhydryl PEG, 10,000 mol. wt.

IAM-PEG was dissolved at 20% (w/v) in 0.5 mM sodium phosphate, pH 6.0, and mixed rapidly with a 20% (w/v) solution of tetra-sulfhydryl PEG in P/C Buffer sodium phosphate-carbonate, pH 9.6. Gelation occurred in less than 40 sec. A firm gel formed within 2 min.

8c: Gelation of Tetra-Sulfhydryl PEG, 10.000 mol. wt., with Dilute Hydrogen Peroxide A 20% (w/v) solution of tetra-sulfhydryl PEG in P/C Buffer, was mixed with an equal volume of 0.1% (w/v) hydrogen peroxide. Gelation occurred in 15 sec. A firm gel formed in less than 2 min.

Example 9

Blood Coagulation Activity of Thrombin Incorporated into PEG Compositions

This experiment demonstrates that hemostatic PEG gels containing active thrombin protein can be formed on tissue.

9a: Thrombin Incorporated into Tetra-Sulfhydryl PEG Gelled with Hydrogen Peroxide 20 mg of tetra-sulfhydryl PEG, 10,000 mol. wt., were dissolved in 80 µl of PC Buffer, and 11 µl of bovine thrombin at 8850 NH units/ml in 0.72 M sodium chloride (Thrombin topical, USP, Gentrac, Inc., Middleton, Wis.) were added. This solution of tetra-sulfhydryl PEG and thrombin was then mixed with 100 µl of 0.1% (w/v) hydrogen peroxide in water, by stirring rapidly in a 1.5 ml plastic tube. The mixture gelled in less than 40 sec, due to oxidation of the sulfhydryl groups to disulfide bonds. After 1.5 min, the gel was a firm, rubbery solid. On top of this gel was layered 200 µl of rabbit blood plasma. The plasma had been separated from citrated blood and contained approximately 11 mM citrate. Just prior to addition, this citrated blood plasma was re-calcified by addition of 8 µl of 0.5 M calcium chloride, to achieve a concentration of about 20 mM calcium. This re-calcified blood plasma was observed to form a fibrin clot 1.5 minutes after layering onto the PEG gel. The clotting reaction was taken as evidence for the presence of active thrombin in the PEG gel.

When control studies are performed, a second oxidized sulfhydryl-PEG gel without thrombin does not clot rabbit plasma until 20 minutes have elapsed. As a further control, re-calcified rabbit plasma is held in an identical plastic tube; and it clots spontaneously after 13 minutes. Therefore, the sulfhydryl-PEG gel without thrombin clots blood no faster than control re-calcified plasma.

When the analogous experiment was attempted with tetra-sulfhydryl PEG and tetra-SG-PEG, plus thrombin, no enhanced clotting time of plasma was observed. Clotting of plasma was delayed beyond 25 minutes. This result is interpreted to indicate that SG-PEG inactivated thrombin, presumably by binding PEG to lysine side chains of thrombin and interfering with its enzymatic activity.

9b: Thrombin Incorporated into LAM-PEG/Sulfhydryl-PEG Gel 20 mg of tetra-sulfhydryl PEG, 10,000 mol. wt. are dissolved in 80 µl of PC Buffer along with 11 µl of thrombin, as in 9a. above. 20 mg of LAM-PEG are dissolved in 80 µl of 0.5 mM sodium phosphate, pH 6.0. The two solutions are rapidly mixed in a 1.5 ml plastic tube. The mixture has a gel time less than 30 sec and is a rubbery gel by 1.5 minutes. Re-calcified rabbit plasma (200 µl) is layered on top of the gel, and a fibrin clot forms in this plasma in less than two minutes after layering onto the gel. A control reaction without thrombin forms a fibrin clot more than 18 minutes after layering onto the PEG gel. The rapid formation of a fibrin clot in the sample containing thrombin is taken as evidence for the presence of active thrombin in the PEG gel.

9c: Thrombin Incorporated into NEM-PEG/Sulfhydryl PEG Gel 20 mg of tetra-sulfhydryl PEG, 10,000 mol wt., is dissolved in 80 µl of 150 mM sodium phosphate, pH 5.0, along with 11 µl of thrombin, as in 9a above. 20 mg of NEM-PEG are dissolved in 0.5 mM sodium phosphate, pH 6.0. The two solutions are rapidly mixed in a plastic tube. Gelation occurs in 15 sec. 15 ml of P/C Buffer, are layered onto the top of the PEG gel to adjust the pH to 7-9. Then, 200 µl of re-calcified rabbit plasma are added. A fibrin clot formed in 1.5 min. after addition of the plasma. Control gels with no thrombin form a fibrin clot after 30 min. Again, the rapid formation of a fibrin clot in the PEG gel with thrombin is taken as evidence for the presence of active thrombin.

9d: Gelation of Layered Gels with Thrombin

In order to provide a gel formulation from SG-PEG and sulfhydryl-PEG to which thrombin can be added and remain active, a "gel layering" technique can be used. First, the tetra-sulfhydryl-PEG and tetra-Se-PEG gel at 20% solids, prepared according to Example 1 are sprayed onto sheets as described in Example 2. The sheets are coarse fibered collagen hydrated by saline, which simulates a tissue surface. The total volume is approximately 0.5 ml. This formula gels in 18-15 sec. At 16 seconds, a second gel mixture of tetra-sulfhydryl PEG, di-maleimidyl PEG, both at 20% solids, and thrombin (700 NIH units/ml) of total gel mixture, total volume approx. 0.5 ml, are sprayed on top of the first gel. This second gel layer gels at about 2 minutes. At 3 min after the first gel is sprayed, 0.4 ml of re-calcified rabbit blood plasma, prepared as described above are layered on top of the PEG gel. This plasma clots 1.5 minutes after it is layered onto the PEG gel. The formation of a fibrin clot at this early time, compared to a non-thrombin control, is taken as evidence for active thrombin in the PEG gel.

Example 10

Gelation Using Powdered Formulations 10 mg of powdered tetra-SG PEG, 10,000 mol. wt., is spread on the surface of a piece of weighing paper. 10 mg of tetra-sulfhydryl PEG, 10,000 mol. wt., is dissolved in 80 µl of P/C buffer. The sulfhydryl-PEG solution is loaded into a 1 cc syringe with a Haemedics (Malibu, Calif.) spray head and sprayed onto the SG-PEG on the weighing paper. The sprayed fluid is not stirred or mixed. It begins to gel in 27 seconds and forms a firm, rubbery layer by 2 min. This test shows that components in powdered form are also suitable for use in the present invention.

Example 11

Collagen-Containing Compositions

Methylated collagen is prepared by the following process: bovine corium collagen is solubilized using pepsin and purified as described in U.S. Pat. No. 4,233,360. This purified, solubilized collagen is precipitated by neutralization into 0.2M sodium phosphate, pH 7.2. The precipitate is isolated by centrifugation to a final concentration of 70 mg/ml. The material is dried for two days, and then pulverized. Dry methanol containing HCl (to 0.1 N) is added (40 ml) and stirred for four days. Collagen is separated from the acidic methanol, vacuum dried and sterilized by irradiation. The final product is dissolved in water at a pH of 3-4.

For delivery as a sealant, 10 mg of the methylated collagen, 100 mg of tetra-functional sulfhydryl-PEG, 10,000 mol. wt., and 100 mg of tetra-functional SG PEG, 10,000 mol. wt., are dissolved in water at pH 3-4 to a final volume of 1 ml (first component). The second component is 1 ml of P/C Buffer. Each component is placed in a syringe and mixed and sprayed on the desired test site using a dual-syringe delivery system as described in Example 1. The applied mixture gels in less than 3 seconds.

The adhesive and cohesive properties of the gel are examined in a burst test. This test is conducted on a pressure gauge apparatus (PSI-Tronix, Model PG5000, Tulare, Calif.) connected by a pressure line to a circular sample plate with a 2 mm diameter central orifice. Sealant formulations are sprayed onto the plate to seal the orifice. To simulate bonding of the formulations to tissue, the sample plate has a circular sheet of coarse-fibered collagen fastened to it, with a 2 mm hole pierced into it and displaced 2-3 mm from the sample plate orifice. Burst strength is measured as a function of the pressure it takes to force saline at a flow rate of 5 ml/min through the sealant gel.

The results are given below in Table 7.

TABLE 7

Burst Strength Measurements of Collagen-Containing Compositions

| Material | Burst Strength, mmHg |
|---|---|
| Sulfhydryl-PEG/SG-PEG | 100-180 |
| Sulfhydryl-PEG/SG-PEG/Methylated Collagen | 122-205 |

Both formulations have gel times less than 3 seconds. As shown above, the addition of collagen to the formulation enhances burst strength.

Example 12

Synthesis of "12-Arm" PEG Compounds

Figure 5A:
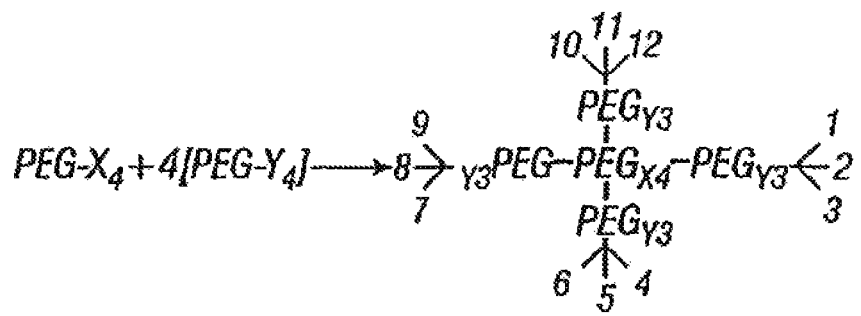
FIGS. 5a and 5b depict the formation of two "12-arm' PEG compounds from "4-arm" intermediates.
Figure 5B:
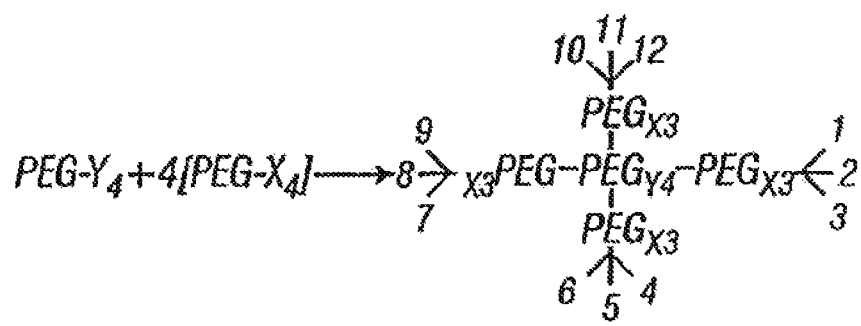

A 12-arm electrophilic PEG compound is formed from 1 mole of 4-arm sulfhydryl PEG, 10,000 mol. wt., and 4 moles of 4-arm SG-PEG, 10,000 mol. wt. The resulting compound is depicted in FIG. 5a. As shown, the compound core is pentaerythritol PEG ether tetra-sulfhydryl and the end functional group is succinimide. As long as the functional groups are reactive with one another to form chemical bonds, the sulfhydryl group, X, can be replaced with other nucleophilic groups, such as $NH_2$, etc., and the succinimidyl group, Y, can be replaced with other electrophilic groups, such as maleimide, carbonyl imidazole, or isocyanate. This method is also used to prepare the 12-arm nucleophilic PEG compound depicted in FIG. 5b by reacting 4 moles of 4-arm sulfhydryl PEG with 1 mole of 4-arm SG-PEG. It should be understood that such reactions produce a heterogeneous population of activated PEG product, some having less than 12 arms, and some having more than 12 arms. As used herein, a "12-arm" PEG also refers to such heterogeneous reaction products that have an average of about 12 arms on each molecule.

12a: 12 Arm Sulfhydryl PEG

Eight grams of pentaerythritol (polyethylene glycol)ether tetra sulfhydryl was dissolved in a mixture of 100 mL of methylene chloride and 100 mL of triethylamine. Two grams of pentaerythritol (polyethylene glycol)ether tetra succinimidyl glutarate in 40 mL of methylene chloride was slowly added with stirring at room temperature under argon overnight. The solvent was removed and the product was isolated by recrystallilzation in ethanol and dried.

12b: 12 Arm Succinimidyl PEG

Two grams of pentaerythritol (polyethylene glycol)ether tetra succinimidyl glutarate was dissolved in 50 mL of methylene chloride. 0.5 grams of pentaerythritol (polyethylene glycol)ether tetra amine in 10 mL of methylene chloride was slowly added with stirring at room temperature under argon overnight. The solvent was removed and the product was isolated by recrystallization in ethanol and dried.

When the two compounds were tested for burst strength as described in Example 12, they demonstrated a burst strength of greater than 150 mm Hg and a gel time of less than 2 seconds.

Example 13

Preparation of Microspheres with and without Paclitaxel

A) PVA Solution Preparation

1. In a 1000 ml beaker, 1000 ml of distilled water and 100 g of PVA (Aldrich 13-23K, 98% hydrolyzed) are weighed. A two-inch stirrer bar is placed into the beaker. The suspension is heated up to 75-80° C. during stirring. The PVA is dissolved completely (should form a clear solution).

2. The 10% PVA solution (w/v) is cooled down to room temperature and filtered through a syringe in-line filter. Stored at 2-8° C. for use.

B) PLGA Solution Preparation with or without Paclitaxel

1. Appropriate amount of paclitaxel and PLGA (for a total of 1.0 g) are weighed and transferred into the 20 ml scintillation vial.

2. 10 mL of HPLC grade dichloromethane (DCM) is added into the vial to dissolve the PLGA with or without paclitaxel.

3. The polymer with or without paclitaxel is dissolved in DCM by placing the vial on an orbital shaker. The orbital shaker is set at 4.

Preparation of the Microspheres with Diameter Less than 25 mm 1. 100 ml of 10% PVA solution is transferred into a 400 ml beaker. The beaker is secured by a double side adhesive tape onto the fume-hood. A peddler with 3 blades is placed into the beaker with 0.5 cm above the bottom. The motor is turned on to 2.5 (Dyna-Mix from Fisher Scientific) at first. The 10 ml PLGA/paclitaxel solution is poured into the PVA solution during agitation. Gradually turn up the agitation rate to 5.0. The stirring is maintained for 2.5 to 3.0 hours.

2. The obtained microspheres are filtered through a set of sieves with 53 mm (top) and 25 mm (bottom) into a 100 ml beaker. The microspheres are washed using distilled water while filtering. The filtered microspheres are centrifuged (1000 rpm, 10 min.) and re-suspended/washed with 100 ml distilled water three times to clean the PVA.

3. The washed microspheres are transferred into the freeze-dried beaker using a small amount of distilled water (20-30 ml). The beaker is then sealed and placed into a −20° C. freezer over night.

4. The frozen microspheres are then freeze-dried using a freeze-drier for about 3 days. The dried microspheres are transferred into 20 ml scintillation vial and stored at −20° C.

In a similar manner described above, other biologically active agents, as described above, can be incorporated into a microsphere formulation.

Example 14

Mycophenolic Acid Incorporation into Microspheres

Mycophenolic acid was incorporated into microspheres in a similar manner as described in Example 13.

Example 15

Incorporation of Paclitaxel-Loaded Microspheres

Method 1

Various amounts of the microspheres prepared in Example 13 are weighed out and mixed with the pentaerythritol poly(ethylene glycol)ether tetra-succinimidyl glutarate. The formulation is then prepared in the same manner as that described in Example 1. Microspheres loaded with other agents, for example mycophenolic acid, are incorporated into the composition in a similar manner.

Example 16

Incorporation of Paclitaxel-Loaded Microspheres

Method 2

Various amounts of the microspheres prepared in Example 13 are weighed out and mixed with 0.5 mM sodium phosphate pH 6.0 buffer. The microsphere containing buffer is then used to prepare the formulation in the same manner as that described in example 1. Microspheres loaded with other agents, for example mycophenolic acid, are incorporated into the composition in a similar manner.

Example 17

Preparation of Chlorpromazine Microspheres

Various amounts of chlorpromazine are dissolved in 1 mL 5% PVA solution. This solution is then added to 10 mL dichloromethane (DCM) that is in a 25 mL beaker. The solution is homogenized (setting 5) for 2 minutes using a tissue homogenizer. The resultant solution is then poured into 50 mL 5% PVA solution. The solution is then homogenized (setting 5) for 2 minutes. The sample is then placed on the rotavap and the solvent is gradually removed using a shallow increasing vacuum gradient. Once the majority of the DCM is removed, the sample is frozen and freeze dried.

Example 18

Efficacy of Drug Loaded Formulations

Adhesion Prevention

The compositions prepared in Examples 1, 15, 16 and 17 are tested in the rat cecal side wall model (see General Method A) and the rabbit uterine horn model (see General Method B). The compositions as prepared in Examples 1, 15 and 16 were applied to the site of injury as a spray using an air assisted spray device (available from Cohesion Technologies or Micromedics) that mixed the 2 component solutions.

Example 19

Direct Incorporation of Drugs into Rapid Gelling Formulation

Mycophenolic Acid (MPA)-Premix

Reagents:
  Syringe 1: A 1 mL syringe equipped with a BBraun luer-lock mixing connector (FDC1000/415080) containing PEG-SG4 (tetra functional poly(ethylene glycol) succinimidyl glutarate) 50 mg, PEG-SH4 (tetra functional poly(ethylene glycol)thiol 50 mg and MPA (mycophenolic acid) 5 to 45 mg. The mycophenolic acid was less than 100 um in particles size. This was obtained by using a 100 um sieve.
  Syringe 2: A 1 mL capped syringe with 0.25 mL 6.3 mM HCl solution.
  Syringe 3: A 1 mL capped syringe with 0.25 mL 0.12 M monobasic sodium phosphate and 0.2 M sodium carbonate (pH 9.7).
Applicator: Micromedics Y-shaped blending connector with a spray-tip (SA-3674), or similar.
Procedure:
  Syringe 1 containing the solids and syringe 2 containing the acidic solution was mixed through the green mixing connector by repeatedly transferring from one syringe to the other by pushing the plungers back and forth. After complete mixing, all of the formulation was pushed into one of the syringes which was attached to one inlet of the Y-shaped applicator equipped with the spray tip. Syringe 3 containing the pH 9.7 solution was attached onto the other inlet of the Y-shaped applicator. A connector clip was attached to the plungers of the two syringes. The formulation was applied by quickly and evenly depressing the connected syringe plungers.
  For mycophenolic acid amounts in the 50 to 100 mg range, a 1 mL capped syringe with 0.25 mL 0.24 M monobasic sodium phosphate adjusted to pH 10 with sodium carbonate was used as syringe 3.

Example 20

Direct Incorporation of Drugs into Rapid Gelling Formulation

CELLCEPT-Premix

CELLCEPT (Syntex Laboratories, Inc., Palo Alto, Calif.) was incorporated into the composition in a similar manner to that described in Example 19. 5 mg CELLCEPT was added to the 2 PEG components in syringe 1. The composition was prepared and applied as described in Example 19. mycophenolic acid was included in these compositions.

Example 21

Direct Incorporation of Drugs into Rapid Gelling Formulation

Chlorpromazine (CPZ)-Premix

In a similar manner to that described in Example 19, Chlorpromazine was incorporated into the composition. Compositions containing between 5 and 20 mg Chlorpromazine were prepared in a similar manner as to that described in Example 19. No mycophenolic acid was included in these compositions.

Example 22

Direct Incorporation of Drugs into Rapid Gelling Formulation

Mycophenolic Acid—Separate Drug Component

Components:
Syringe 1: A 1 mL syringe equipped with a BBraun luer-lock mixing connector (FDC1000/415080) containing 50 mg PEG-SG4 (tetra functional poly(ethylene glycol) succinimidyl glutarate) and 50 mg PEG-SH4 (tetra functional poly(ethylene glycol)thiol).
Syringe 2: 1 mL syringe equipped with a BBraun luer-lock mixing connector (FDC1000/415080) containing between 5 and 45 mg MPA (mycophenolic acid) [sieved to a particle size less than 100 micron].
Syringe 3: A 1 mL capped syringe with 0.25 mL 6.3 mM HCl solution.
Syringe 4: A 1 mL capped syringe with 0.25 mL 0.12 M monobasic sodium phosphate and 0.2 M sodium carbonate (pH 9.7).
Applicator: Micromedics Y-shaped blending connector with a spray-tip(SA-3674), or similar.
Procedure:
Syringe 1 containing the solids was connected to syringe 3 containing the acidic solution through the green mixing connector. The contents were mixed by using the plungers to transfer the onetnes of one syringe into the other. This process was repeated at least 20 times. After complete mixing, all of the formulation was pushed into one of the syringes which was attached to one inlet of the Y-shaped applicator equipped with the spray tip. Syringe 4 and 2 (containing the drug) were similarly mixed and attached onto the other inlet of the Y-shaped applicator. A connector clip was attached to the plungers of the two syringes The formulation was applied by quickly and evenly depressing the connected syringe plungers.

For mycophenolic acid amounts in the 50 to 100 mg range, a 1 mL capped syringe with 0.25 mL 0.24 M monobasic sodium phosphate adjusted to pH 10 with sodium carbonate was used as syringe 4.

Example 23-A

Direct Incorporation of Drugs into Rapid Gelling Formulation

CELLCEPT-premix

CELLCEPT was incorporated into the composition in a similar manner to that described in Example 22. 5 mg CELLCEPT was contained in syringe 2. The composition was prepared and applied as described in Example 22. Mycophenolic acid was included in these compositions.

Example 23-B

Mycophenolic Acid-Containing Microspheres Prepared by Spray Drying

Poly(L-lactic acid) (Mw 2000), was dissolved in methylene chloride to result in a 0.2% solution. MPA was added in at different weight ratios relative to the carrier polymer. These ranged from 10 to 50%. The resulting solution was spray dried using a Buchi Research Spray Drier and the following conditions: Inlet temperature 50° C., outlet temperature<39° C., aspirator 100%, flow rate 700 L/hr. The collected microspheres were further dried under vacuum. MPA-containing microspheres were made in a similar manner to that described above except that poly(caprolactone) (Mw 9,000), PLGA (Mw 54K), PLURONIC-F127 or methoxy poly(ethylene glycol 5000)-block-poly (DL-lactide) (65:35 or 60:40 PEG:PDLLA weight ratio) were used instead of the poly(L-lactic acid).

Example 23

Chlorpromazine-Containing Microspheres Prepared by Spray Drying

Methoxy poly(ethylene glycol 5000)-block-poly (DL-lactide) (65:35 PEG:PDLLA weight ratio) or PLURONIC-F127 was dissolved in methylene chloride to result in a 0.2% solution. Chlorpromazine was added in 10% weight ratio relative to the carrier polymer. The resulting solution was spray dried using a Buchi Research Spray Drier and the following conditions: Inlet temperature 50° C., outlet temperature<39° C., aspirator 100%, flow rate 700 L/hr. The collected microspheres were further dried under vacuum.

Example 24

Paclitaxel-Containing Microspheres Prepared by Spray Drying

Methoxy poly(ethylene glycol 5000)-block-poly (DL-lactide) (65:35 or 60:40 PEG:PDLLA weight ratio) was dissolved in methylene chloride to result in a 0.2% solution. Paclitaxel was added in 10% weight ratio relative to the carrier polymer and the resulting solution was spray dried using a Buchi Research Spray Drier and the following conditions: Inlet temperature 50° C., outlet temperature<39° C., aspirator 100%, flow rate 700 L/hr. The collected microspheres were further dried under vacuum.

Example 25

Mycophenolic Acid-Containing Microspheres (<10 Microns) Prepared by Emulsion Method Into a 600 mL beaker was added 100 mL of freshly prepared 10% polyvinyl alcohol (PVA) solution and 10 mL of pH 3 acetic acid solution saturated with MPA. This acidified PVA solution was stirred at 2000 rpm for 30 minutes. Meanwhile, solution containing between 80-400 mg MPA and 800 mg PLGA in 20 mL dichloromethane were prepared. Each of these dichloromethane solutions were individually added drop wise to a PVA solution while stirring at 2000 rpm with a Fisher Dyna-Mix. After addition was complete, the solution was allowed to stir for 45 minutes. The microsphere solution was transferred to falcon tubes, washed with a pH 3 acetic acid solution saturated with MPA, and centrifuged at 2600 rpm for 10 minutes. The aqueous layer was decanted and the washing, centrifuging and decanting was repeated 3 times. The washed microspheres from each batch were freeze-dried.

Example 26

Mycophenolic Acid-Containing Microspheres (50-130 Microns) Prepared by Emulsion Method Into a 600 mL beaker was added 100 mL of freshly prepared 1% polyvinyl alcohol solution and 10 mL of pH 3 acetic acid solution saturated with MPA. This acidified PVA solution was stirred at 500 rpm for 30 minutes. Meanwhile, a solution of 80-400 mg MPA and 800 mg PLGA in 20 mL dichloromethane was prepared. This dichloromethane solution was added drop wise to the PVA solution while stirring at 500 rpm with a Fisher Dyna-Mix. After addition was complete, the solution was allowed to stir for 45 minutes. The microsphere solution was transferred to falcon tubes, washed with a pH 3 acetic acid solution saturated with MPA, and centrifuged at 2600 rpm for 10 minutes. The aqueous layer was decanted and the washing, centrifuging and decanting was repeated 3 times. The combined, washed microspheres were freeze-dried to remove any excess water. The product was sieved to isolate microspheres of 53-125 μm size.

Example 27

Incorporation of Drug-Loaded Carriers into the PEG Compositions

Drug-loaded microspheres, 5 to 100 mg, were incorporated into compositions as a mixture in a similar manner as to that described in Example 19 or as a separate component in a manner similar to that described in Example 22.

Example 28

Incorporation of Additives into MPA-Loaded Microspheres

Methoxy poly(ethylene glycol 5000)-block-poly (DL-lactide) (65:35 or 60:40 PEG:PDLLA weight ratio) was dissolved in the appropriate solvent (see below) to result in a 0.2% solution. MPA was added in 10% weight ratio relative to the carrier polymer. Different additives were then individually added to the drug/polymer solution. The nature of the additive and the amounts used are described below:

| Additives: | Concentration: | Solvent: |
| --- | --- | --- |
| Histidine | 1-3 molar ratio to MPA | Methylene Chloride |
| Spermidine | 1⅓ molar ratio to MPA | Methylene Chloride |
| 1,2 dipalmitoyl-sn-glycero-3-phosphoethanolamine | 1-15% (w/w) to carrier | Chloroform |
| 1,2, dimyristoyl-sn-glycero-3-ethylphosphocholine chloride | 1-15% (w/w) to carrier) | Chloroform |
| Palmitic Acid | 1-15% (w/w) to carrier) | Methylene Chloride |
| Cholic Acid | 1-15% (w/w) to carrier) | Methylene Chloride |

The resulting solution was spray dried using a Buchi Research Spray Drier and the following conditions: Inlet temperature 50° C., outlet temperature<39° C., aspirator 100%, flow rate 700 L/hr. The collected microspheres were further dried under vacuum. The drug-loaded microspheres were used in direct combination with the PEG reagents, as described in Example 19 or as a separate component as described in Example 22.

Example 29

Rat Surgical Adhesions Model to Assess Fibrosis Inhibiting Agents

Sprague Dawley rats are prepared for surgery by anaesthetic induction with 5% halothane in an enclosed chamber. Anaesthesia is maintained by nose cone on halothane throughout the procedure and Buprenorphen 0.035 mg/kg is injected intramuscularly. The abdomen is shaved, sterilized, draped and entered via a midline incision. The caecum is lifted from the abdomen and placed on sterile gauze dampened with saline. Dorsal and ventral aspects of the caecum are scraped a total of 45 times over the terminal 1.5 cm using a #10 scalpel blade, held at a 45° angle. Blade angle and pressure are controlled to produce punctuated bleeding, while avoiding severe tissue damage or tearing.

The left side of the abdominal cavity is retracted and everted to expose a section of the peritoneal wall nearest the natural resting caecal location. The exposed superficial layer of muscle (transverses abdominis) is excised over an area of $1.0 \times 1.5$ cm$^2$. Excision includes portions of the underlying internal oblique muscle, leaving behind some intact and some torn fibres from the second layer. Minor local bleeding is tamponaded until controlled.

A test formulation is deployed at the wounded areas, on the abraded sidewall, between the caecum and sidewall. The formulation is deployed using either a syringe spray system or an air-assisted syringe system. The abraded caecum is then positioned over the sidewall wound and sutured at four points immediately beyond the dorsal corners of the wound edge. The large intestine is replaced in a natural orientation continuous with the caecum. The abdominal incision is closed in two layers with 4-0 silk sutures.

Rats are followed for one week, and then euthanized by lethal injection for post mortem examination to score. Severity of post-surgical adhesions is scored by independently assessing the tenacity and extent of adhesions at the site of caecal-sidewall abrasion, at the edges of the abraded site, and by evaluating the extent of intestinal attachments to the exposed caecum. Adhesions are scored on a scale of 0-4 with increasing severity and tenacity. The extent of adhesion is scored as a percent of the injured area that contained adhesions.

Example 30

Screening Assay for Assessing the Effect of Mitoxantrone on Cell Proliferation Fibroblasts at 70-90% confluency are trypsinized, replated at 600 cells/well in media in 96-well plates and allowed to attachment overnight. Mitoxantrone is prepared in DMSO at a concentration of $10^{-2}$ M and diluted 10-fold to give a range of stock concentrations ($10^{-8}$ M to $10^{-2}$ M). Drug dilutions are diluted 1/1000 in media and added to cells to give a total volume of 200 μL/well. Each drug concentration is tested in triplicate wells. Plates containing fibroblasts and mitoxantrone are incubated at 37° C. for 72 hours (In vitro toxicol. (1990) 3: 219; Biotech. Histochem. (1993) 68: 29; Anal. Biochem. (1993) 213: 426).

Figure 6:
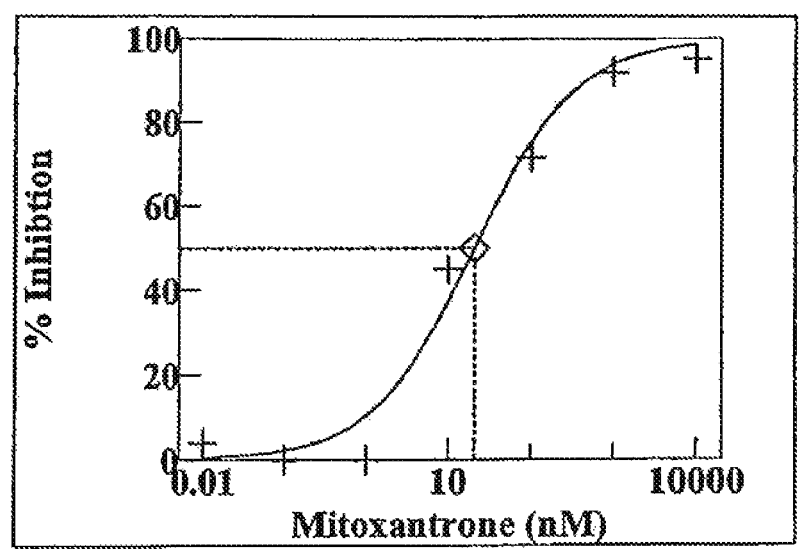
FIG. 6 is a graph showing % inhibition of human fibroblast cell proliferation as a function of Mitoxantrone concentration.

To terminate the assay, the media is removed by gentle aspiration. A 1/400 dilution of CYQUANT 400×GR dye indicator (Molecular Probes; Eugene, Oreg.) is added to 1× Cell Lysis buffer, and 200 μL of the mixture is added to the wells of the plate. Plates are incubated at room temperature, protected from light for 3-5 minutes. Fluorescence is read in a fluorescence microplate reader at ~480 nm excitation wavelength and ~520 nm emission maxima. Inhibitory concentration of 50% ($IC_{50}$) is determined by taking the average of triplicate wells and comparing average relative fluorescence units to the DMSO control. An average of n=4 replicate experiments is used to determine $IC_{50}$ values. The results of the assay are shown in FIG. 6 ($IC_{50}$=20 nM for proliferation of human fibroblasts).

Example 31

Screening Assay for Assessing the Effect of Mitoxantrone on Nitric Oxide Production by Macrophages The murine macrophage cell line RAW 264.7 is trypsinized to remove cells from flasks and plated in individual wells of a 6-well plate. Approximately $2 \times 10^6$ cells are plated in 2 mL of media containing 5% heat-inactivated fetal bovine serum (FBS). RAW 264.7 cells are incubated at 37° C. for 1.5 hours to allow adherence to plastic. Mitoxantrone is prepared in DMSO at a concentration of $10^{-2}$ M and serially diluted 10-fold to give a range of stock concentrations ($10^{-8}$ M to $10^{-2}$ M). Media is then removed and cells are incubated in 1 ng/mL of recombinant murine IFNγ and 5 ng/mL of LPS with or without mitoxantrone in fresh media containing 5% FBS. Mitoxantrone is added to cells by directly adding mitoxantrone DMSO stock solutions, prepared earlier, at a 1/1000 dilution, to each well. Plates containing IFNγ, LPS plus or minus mitoxantrone are incubated at 37° C. for 24 hours (Chem. Ber. (1879) 12: 426; J. AOAC (1977) 60-594; Ann. Rev. Biochem. (1994) 63: 175).

Figure 7:
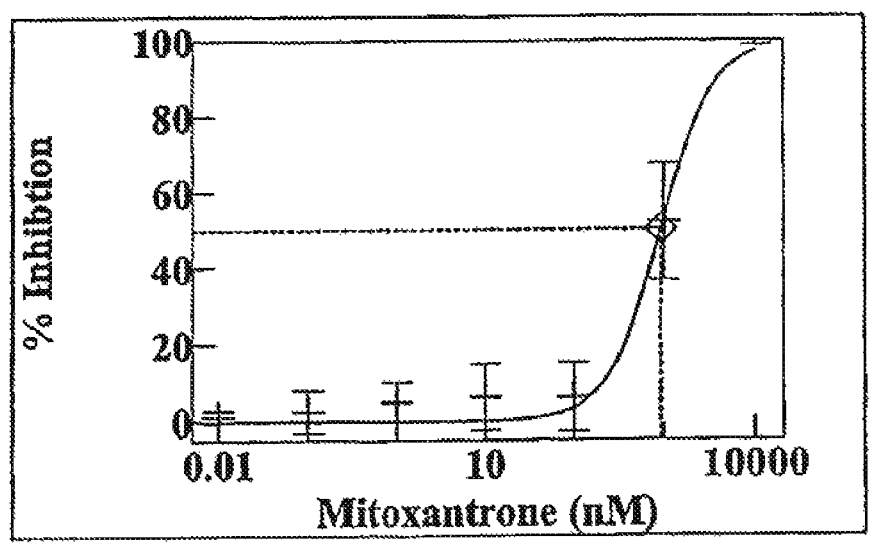
FIG. 7 is a graph showing % inhibition of nitric oxide production in RAW 264.7 cells. as a function of Mitoxantrone concentration.

At the end of the 24 hour period, supernatants are collected from the cells and assayed for the production of nitrites. Each sample is tested in triplicate by aliquoting 50 μL of supernatant in a 96-well plate and adding 50 μL of Greiss Reagent A (0.5 g sulfanilamide, 1.5 mL $H_3PO_4$, 48.5 mL dd$H_2O$) and 50 μL of Greiss Reagent B (0.05 g N-(1-Naphthyl)-ethylenediamine, 1.5 mL $H_3PO_4$, 48.5 mL dd$H_2O$). Optical density is read immediately on microplate spectrophotometer at 562 nm absorbance. Absorbance over triplicate wells is averaged after subtracting background and concentration values are obtained from the nitrite standard curve (1 μM to 2 mM). Inhibitory concentration of 50% ($IC_{50}$) is determined by comparing average nitrite concentration to the positive control (cell stimulated with IFNγ and LPS). An average of n=4 replicate experiments is used to determine $IC_{50}$ values for mitoxantrone. The results of the assay are shown in FIG. 7 (Mitoxantrone $IC_{50}$=927 nM for Greiss assay in RAW 264.7 cells).

Example 32

Screening Assay for Assessing the Effect of Bay 11-70820N TNF-Alpha Production by Macrophages The human macrophage cell line, THP-1 is plated in a 12 well plate such that each well contains $1 \times 10^6$ cells in 2 mL of media containing 10% FCS. Opsonized zymosan is prepared by resuspending 20 mg of zymosan A in 2 mL of dd$H_2O$ and homogenizing until a uniform suspension is obtained. Homogenized zymosan is pelleted at 250 g and resuspended in 4 mL of human serum for a final concentration of 5 mg/mL. and incubated in a 37° C. water bath for 20 minutes to enable opsonization. Bay 11-7082 is prepared in DMSO at a concentration of $10^{-2}$ M and serially diluted 10-fold to give a range of stock concentrations ($10^{-8}$ M to $10^{-2}$ M) (J. Immunol. (2000) 165: 411-418; J. Immunol. (2000) 164: 4804-4811; J. Immunol. Meth. (2000) 235 (1-2): 33-40).

THP-1 cells are stimulated to produce TNFα by the addition of 1 mg/mL opsonized zymosan. Bay 11-7082 is added to THP-1 cells by directly adding DMSO stock solutions, prepared earlier, at a 1/1000 dilution, to each well. Each drug concentration is tested in triplicate wells. Plates are incubated at 37° C. for 24 hours.

Figure 8:
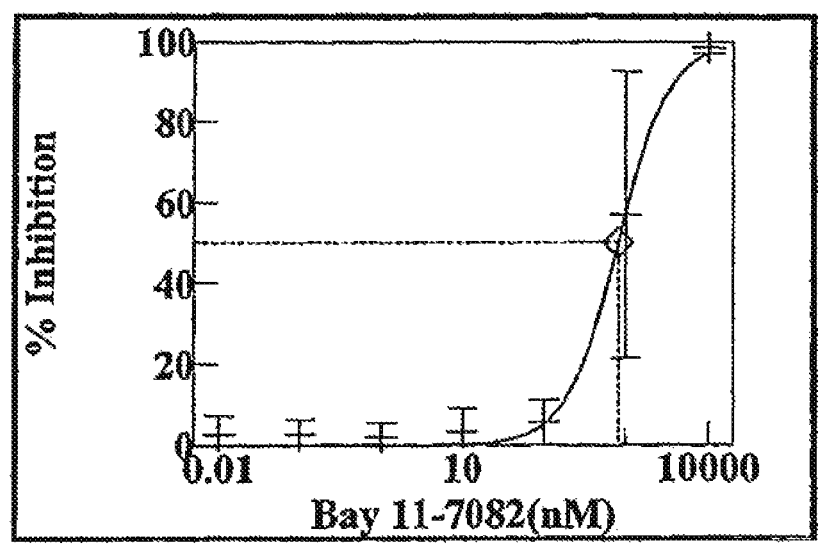
FIG. 8 is a graph showing % inhibition of TNFα production by THP-1 cells as a function of Bay 11-7082 concentration.

After a 24 hour stimulation, supernatants are collected to quantify TNFα production. TNFα concentrations in the supernatants are determined by ELISA using recombinant human TNFα to obtain a standard curve. A 96-well MaxiSorb plate is coated with 100 μL of anti-human TNFα Capture Antibody diluted in Coating Buffer (0.1 M Sodium carbonate pH 9.5) overnight at 4° C. The dilution of Capture Antibody used is lot-specific and is determined empirically. Capture antibody is then aspirated and the plate washed 3 times with Wash Buffer (PBS, 0.05% Tween-20). Plates are blocked for 1 hour at room temperature with 200 μL/well of Assay Diluent (PBS, 10% FCS pH 7.0). After blocking, plates are washed 3 times with Wash Buffer. Standards and sample dilutions are prepared as follows: (a) sample supernatants are diluted 1/8 and 1/16; (b) recombinant human TNFα is prepared at 500 pg/mL and serially diluted to yield as standard curve of 7.8 pg/mL to 500 pg/mL. Sample supernatants and standards are assayed in triplicate and are incubated at room temperature for 2 hours after addition to the plate coated with Capture Antibody. The plates are washed 5 times and incubated with 100 μL of Working Detector (biotinylated anti-human TNFα detection antibody+avidin-HRP) for 1 hour at room temperature. Following this incubation, the plates are washed 7 times and 100 μL of Substrate Solution (Tetramethylbenzidine, $H_2O_2$) is added to plates and incubated for 30 minutes at room temperature. Stop Solution (2 $NH_2SO_4$) is then added to the wells and a yellow colour reaction is read at 450 nm with λ correction at 570 nm. Mean absorbance is determined from triplicate data readings and the mean background is subtracted. TNFα concentration values are obtained from the standard curve. Inhibitory concentration of 50% ($IC_{50}$) is determined by comparing average TNFα concentration to the positive control (THP-1 cells stimulated with opsonized zymosan). An average of n=4 replicate experiments is used to determine $IC_{50}$ values for Bay 11-7082. The results of the assay are shown in FIG. 8 (Bay 11-7082 $IC_{50}$=810 nM TNFα production by THP-1 cells).

Example 33

Rabbit Surgical Adhesions Model to Assess Fibrosis Inhibiting Agents

The rabbit uterine horn model is used to assess the antifibrotic capacity of formulations in vivo. Mature New Zealand White (NZW) female rabbits are placed under general anesthetic. Using aseptic precautions, the abdomen is opened in two layers at the midline to expose the uterus. Both uterine horns are lifted out of the abdominal cavity and assessed for size on the French Scale of catheters. Horns between #8 and #14 on the French Scale (2.5-4.5 mm diameter) are deemed suitable for this model. Both uterine horns and the opposing peritoneal wall are abraded with a #10 scalpel blade at a 45° angle over an area 2.5 cm in length and 0.4 cm in width until punctuate bleeding is observed. Abraded surfaces are tamponaded until bleeding stops. The individual horns are then opposed to the peritoneal wall and secured by two sutures placed 2 mm beyond the edges of the abraded area. The formulation is applied and the abdomen is closed in three layers. After 14 days, animals are evaluated post mortem with the extent and severity of adhesions being scored both quantitatively and qualitatively.

Example 34

Screening Procedure for Assessment of Perigraft Reaction

Large domestic rabbits are placed under general anesthetic. Using aseptic precautions, the infrarenal abdominal aorta is exposed and clamped at its superior and inferior aspects. A longitudinal arterial wall arteriotomy is performed and a 2 millimeter diameter, 1 centimeter long segment of PTFE graft is inserted within the aorta and the proximal and distal aspect of the graft is sewn so that the entire aortic blood flow is through the graft which is contained in the abdominal aorta in the manner of open surgical abdominal aortic repair in humans (except that no aneurysm is present in this model). The aortotomy is then surgically closed and the abdominal wound closed and the animal recovered.

The animals are randomized to receive standard PTFE grafts or grafts of which the middle 1 cm is coated alone circumferentially with nothing, or with an agent that induces a vessel wall reaction or adhesion between a stent graft and vessel wall alone or contained in a slow release, polymer.

The animals are sacrificed between 1 and 6 weeks post surgery, the aorta is removed en bloc and the area in relation to the graft is grossly examined for adhesive reaction. Any difference in morphology or histology of the vessel wall from portions of the artery which contain no graft, portion which contain graft without coating, and portion which contained graft with coating is noted.

Example 35

Animal Abdominal Aortic Aneurysm Model

Pigs or sheep are placed under general anesthetic. Using aseptic precautions the abdominal aorta is exposed. The animal is heparinized and the aorta is cross clamped below the renal arteries and above the bifurcation. Collaterals are temporarily controlled with vessel loops or clips that are removed upon completion of the procedure. A longitudinal aortotomy is created in the arterial aspect of the aorta, and an elliptical shaped patch of rectus sheath from the same animal is sutured into the aortotomy to create an aneurysm. The aortic clamps from the lumbar arteries and collaterals are removed and the abdomen closed. After 30 days, the animal is reanesthesized and the abdominal wall again opened. A cutdown is performed on the iliac artery and through this, a stent graft is positioned across the infrarenal abdominal aorta aneurysm extending from normal infrarenal abdominal aorta above to normal infrarenal abdominal aorta below the surgically created aneurysm and the device is released in a conventional way.

Animals are randomized into groups of 5 receiving uncoated stent grafts, stent graft containing slow release polymer alone, and stent graft containing a biologically active or irritative substance as determined by the previously mentioned screening exam. After closure of the arteriotomy and of the abdominal wound, the animal is allowed to recover. At 6 weeks and 3 months post stent graft insertion, the animal is sacrificed and the aorta removed en bloc. The infrarenal abdominal aorta is examined for evidence of histologic reaction and perigraft leaking.

Example 36

Screening Procedure for Assessment of Perigraft Reaction

Large domestic rabbits are placed under general anesthetic. Using aseptic precautions, the infrarenal abdominal aorta is exposed and clamped at its superior and inferior aspects. A longitudinal arterial wall arteriotomy is performed and a 2 millimeter diameter, 1 centimeter long segment of PTFE graft is inserted within the aorta and the proximal and distal aspect of the graft is sewn so that the entire aortic blood flow is through the graft which is contained in the abdominal aorta in the manner of open surgical abdominal aortic repair in humans (except that no aneurysm is present in this model). The aortotomy is then surgically closed and the abdominal wound closed and the animal recovered.

The animals are randomized to receive standard PTFE grafts, silk stent grafts, or silk stent grafts coated with other agents as described above.

The animals are sacrificed between 1 and 6 weeks post surgery, the aorta is removed en bloc and the area in relation to the graft is grossly examined for adhesive reaction. Any difference in morphology or histology of the vessel wall from portions of the artery that contain no graft, portion which contain graft without coating, and portion which contained graft with coating is noted.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A drug-delivery system comprising:
a first container comprising a first component consisting of a sulfhydryl group-containing compound of formula: Compound$_1$-(SH)$_m$ wherein m≥3, the first container further comprising a hydrophobic drug in a micelle, where the micelle is formed from a sulfhydryl group-containing thiol compound and an A-B block copolymer where A is a poly(alkylene oxide) and B is a degradable polyester; and
a second container comprising a second component consisting of a sulfhydryl reactive group-containing compound of formula: Compound$_2$-Y$_n$, wherein Y is a sulfhydryl reactive acrylate group and wherein n≥3;
wherein each of Compound$_1$ and Compound$_2$ is a multi-arm polymer comprising polyalkylene oxide;
wherein a biocompatible gel forms in less than one minute after contact between the contents of the first container and the contents of the second container, the gel comprising covalent bonds formed between the sulfhydryl reactive groups of the second component and the sulfhydryl groups of each of the first component and the thiol compound; and wherein the hydrophobic drug is admixed in the biocompatible gel.

2. The drug-delivery system of claim 1, wherein m and n are each 4 or 12.

3. The drug-delivery system of claim 1, wherein the polyalkylene oxide is polyethylene glycol.

4. The drug-delivery system of claim 1 wherein the first component is in a liquid medium having an alkaline pH and the second component is in powder form or a liquid medium having a neutral or acidic pH.

5. The drug-delivery system of claim 1 wherein the hydrophobic drug is a cell cycle inhibitor.

6. A method for forming a drug-loaded biocompatible gel in situ, comprising:
   providing a first container comprising a first component consisting of a sulfhydryl group-containing compound of formula: $Compound_1\text{-}(SH)_m$ in a liquid medium having an alkaline pH, wherein $m \geq 3$, where the first container further comprises a hydrophobic drug in a micelle, where the micelle is formed from a sulfhydryl group-containing thiol compound and an A-B block copolymer where A is a poly(alkylene oxide) and B is a degradable polyester;
   providing a second container comprising a second component consisting of a sulfhydryl reactive acrylate group-containing compound of formula: $Compound_2\text{-}Y_n$ in powder form or a liquid medium having a neutral or acidic pH, wherein Y is a sulfhydryl reactive acrylate group and wherein $n \geq 3$;
   wherein each of Compound1 and Compound2 is a multi-arm polymer comprising polyalkylene oxide; and
   combining the contents of the first container and the second container to form a gel incorporating the hydrophobic drug, wherein the sulfhydryl groups of each of the first component and the thiol compound react with the sulfhydryl reactive acrylate groups of the second component to form covalent bonds there between.

7. The method of claim 6, wherein m and n are each 4 or 12.

8. The method of claim 6 wherein the hydrophobic drug is a cell cycle inhibitor.

9. A method for forming a drug-loaded biocompatible gel in situ, comprising:
   providing a powdered mixture of a sulfhydryl group-containing compound of formula: $Compound_1\text{-}(SH)_m$, wherein $m \geq 3$, a sulfhydryl reactive group-containing compound of formula: $Compound_2\text{-}Y_n$, wherein Y is a sulfhydryl reactive acrylate group and wherein $n \geq 3$, and wherein each of Compound1 and Compound2 is a multi-arm polymer comprising polyalkylene oxide;
   and a hydrophobic drug in a micelle;
   providing a first buffer having an acidic pH;
   providing a second buffer having an alkaline pH;
   combining the powdered mixture with the first buffer to obtain a solution;
   combining the solution of the powdered mixture with the second buffer to form a gel incorporating the hydrophobic drug in a micelle, where the micelle is formed from a sulfhydryl group-containing thiol compound and an A-B block copolymer where A is a poly(alkylene oxide) and B is a degradable polyester, and wherein the sulfhydryl groups react with the sulfhydryl reactive groups to form covalent bonds there between.

10. The method of claim 9, wherein m and n are each 4 or 12.

11. The method of claim 9, wherein the hydrophobic drug is a cell cycle inhibitor.

\* \* \* \* \*